United States Patent
Johnson et al.

(10) Patent No.: US 8,119,692 B2
(45) Date of Patent: Feb. 21, 2012

(54) HYDROXAMIC ACID DERIVATIVES OF 4-PHENYL 4-HYDROXY, 4-PHENYL 4-ALKOXY AND 4-PHENYL 4-ARYLALKOXY BUTYRIC ACID USEFUL AS THERAPEUTIC AGENTS FOR TREATING ANTHRAX POISONING

(75) Inventors: Alan T. Johnson, Kaneohe, HI (US); Seongjin Kim, Honolulu, HI (US)

(73) Assignee: PanThera Biopharma LLC, Aiea, HI (US)

( * ) Notice: Subject to any disclaimer, the term of this patent is extended or adjusted under 35 U.S.C. 154(b) by 960 days.

(21) Appl. No.: 12/079,722

(22) Filed: Mar. 28, 2008

(65) Prior Publication Data

US 2010/0286125 A1    Nov. 11, 2010

Related U.S. Application Data

(60) Provisional application No. 60/921,583, filed on Apr. 2, 2007.

(51) Int. Cl.
*A61K 31/19* (2006.01)
*C07C 259/04* (2006.01)

(52) U.S. Cl. ............... 514/575; 562/623; 562/621

(58) Field of Classification Search .................. 514/575; 562/623, 621
See application file for complete search history.

(56) References Cited

U.S. PATENT DOCUMENTS

| 4,731,382 A * | 3/1988 | Zusi et al. .................. 514/575 |
| 2005/0113366 A1 | 5/2005 | Bourguignon |

FOREIGN PATENT DOCUMENTS

| WO | WO 03/101382 | 12/2003 |
| WO | WO 2005/027856 A2 | 3/2005 |

OTHER PUBLICATIONS

Alberts, et al. Receptor Flexibility in de Novo Ligand Design and Docking, J. Med. Chem. 2005, 48, 6585-6596.
Naruchi, et al. Photo-induced rearrangement of poly(B-nitrostyrene). Makromol. Chem., Rapid Commun. 1986, 7, 607-611.
Bourguignon, et al. Derivatives of 4-hydroxybutanoic acid ". . . ". PCT Int. Applc. (2002), 81 pp. CODEN: PIXXD2 WO 2002042250 A1 20020530 CAN 136:401535 AN 2002:408626.

* cited by examiner

*Primary Examiner* — Shengjun Wang
(74) *Attorney, Agent, or Firm* — Knobbe, Martens, Olson & Bear LLP

(57) ABSTRACT

Compounds having the formula wherein the symbols have the meaning described in the specification are hydroxamic acid derivatives of 4-phenyl-4-hydroxy-butyric acid and capable of inhibiting the lethal effects of infection by anthrax bacteria and are useful in the treatment of poisoning by anthrax.

17 Claims, No Drawings

US 8,119,692 B2

HYDROXAMIC ACID DERIVATIVES OF 4-PHENYL 4-HYDROXY, 4-PHENYL 4-ALKOXY AND 4-PHENYL 4-ARYLALKOXY BUTYRIC ACID USEFUL AS THERAPEUTIC AGENTS FOR TREATING ANTHRAX POISONING

CLAIM OF PRIORITY

The present application claims the priority of U.S. provisional application Ser. No. 60/921,583 filed on Apr. 2, 2007.

STATEMENT REGARDING FEDERALLY SPONSORED RESEARCH OR DEVELOPMENT

This invention was made with government support under Grant no. R44AI052587 awarded by the National Institutes of Health. The US government has certain rights in the invention.

BACKGROUND OF THE INVENTION

1. Field of the Invention

The present invention is directed to compounds useful for treatment of poisoning by *bacillus anthracis* (anthrax infection or poisoning). More particularly, the invention is directed to compounds capable of inhibiting the lethal effects of infection by anthrax bacteria and are useful in the treatment of poisoning by anthrax. The compounds of the invention are hydroxamic acid derivatives of 4-phenyl 4-hydroxy, 4-phenyl 4-alkoxy and 4-phenyl 4-arylalkoxy butyric acid.

2. Background Art

Anthrax is a disease caused by infection of mammals, including humans, by *bacillus anthracis*. Spores of these bacteria can enter the mammalian, including human body, through skin abrasions, the digestive system or inhalation. Whereas anthrax poisoning in humans through skin abrasion or the digestive system can often be treated with antibiotics, anthrax poisoning in humans by ingestion of aerosol usually results in death of the infected individual.

Relatively recently, devices have been made which incorporate *bacillus anthracis* or its spores and are capable of releasing the bacteria or its spores in aerosol form. This "weaponized" form of anthrax can serve as a "weapon of mass destruction" in biological warfare and is feared in the Western World for its potential use by terrorists against civilian populations.

For all these reasons a serious effort has been made in the fields of medical and related biological research to elucidate the mode and agent of poisoning by *bacillus anthracis* and efforts have been made to synthesize compounds which act as inhibitors of the lethal toxins and therefore can treat the infection.

The following scientific publications describe or relate to the manner of infection by the bacteria and to elucidation of the toxic factors and their mode of action in the mammalian, including human body: Dixon et al. (1999) N. England J. Med. 341. 815-26; Mock et al. Annu. Rev. Microbiol. 55. 647-71; Vitalae et al. (1998) Biochem. Biopphys. Res. Commun. 248, 706-11; Vitalae et al. (2000) Biochem J. 352 Pt 3, 739-45; Duesbery et al. (1998) Science 280. 734-7; Duesbery et al. International Publication No. WO 99/50439; Hammond et al. (1998) Infect. Immun. 66, 2374-8. A summary of these findings is that the toxin, called "lethal factor", released by *bacillus anthracis* is an enzyme that splits an essential peptide needed by mammalian organisms for signal transmission. Thus, inhibitors of this bacterial enzyme are candidates for drugs for treatment of anthrax poisoning.

Published US Patent Application No. 2005/0148629 (Jul. 7, 2005) describes hydroxamic acid compounds which have the general formula shown below where the $R^1$ is aryl, or heteroaryl, or heterocyclic and where R represents a large number of potential substituents, including alkyl, and which can be used in the treatment of anthrax poisoning.

Published International Application WO 2005/027856 (Mar. 31, 2005) describe numerous compounds said to be inhibitors of anthrax lethal factor.

Published International Application WO 97/24117 discloses compounds of the general formula including some examples where the variable p=1, q=0 and m=1. Said compounds are said to be inhibitors of cyclic AMP phosphodiesterase.

The present invention represents a further advance in the field by providing hydroxamic acid derivatives of 4-phenyl 4-hydroxy, 4-phenyl 4-alkoxy and 4-phenyl 4-arylalkoxy butyric acid which are useful to treat anthrax poisoning.

SUMMARY OF THE INVENTION

The present invention relates to compounds of Formula 1

Formula 1 where
X is O, S;
$R^1$ is F, Cl, Br, I, alkyl of 1-3 carbons, alkoxy of 1-3 carbons, thioalkoxy of 1-3 carbons, phenyl, CN, $CF_3$, $OCF_3$, OH, $NH_2$, $NH(C_{1-6}alkyl)$, $N(C_{1-6}alkyl)_2$;
m is an integer having the value of 0 to 3;
$R^2$ is H, alkyl of 1 to 3 carbons, $C_1$-$C_6$-alkylphenyl where the phenyl may be substituted with 0 to 3 $R^1$ groups, $C(O)C_1$-$C_6$-alkyl;
$R^3$ is H, alkyl of 1 to 8 carbons, alkenyl of 2 to 6 carbons and one double bond; alkylcycloalkyl where the alkyl group has 1 to 3 carbons and the cycloalkyl has 3 to 6 carbons, $C_1$-$C_6$-alkylphenyl where the phenyl is substituted with 0 to 3 $R^1$ groups, $C_1$-$C_6$-alkenylphenyl where the alkenyl group has one double bond and the phenyl is substituted with 0 to 3

R[1] groups, $C_1$-$C_6$-alkenyl(phenyl)$_2$ where the alkenyl group has one double bond and the phenyl is substituted with 0 to 3 R[1] groups, $(CH_2)_nOR^4$, $(CH_2)_nNHR^5$, $(CH_2)_nNR^5R^6$, $(CH_2)_nCF_3$;

n is an integer having the value of 1 to 6;

R[4] is H, alkyl of 1 to 6 carbons, alkylphenyl where the alkylgroup has 1 to 6 carbons and the phenyl is substituted with 0-3 R[1] groups;

R[5] is H, alkyl of 1 to 6 carbons, phenyl and the phenyl is substituted with 0-3 R[1] groups, C(O)alkyl of 1 to 4 carbons, C(O)alkylphenyl where the alkylgroup has 1 to 4 carbons and the phenyl is substituted with 0-3 R[1] groups or with a 5 to 6 membered heteroayl group having 1 to 2 heteroatoms selected from O, S, and N, said heteroaryl group itself substituted with 0-3 R[1] groups, or R[5] is alkenylphenyl where the alkenyl group has 2 to 6 carbons and one double bond, $C(O)(CH_2)_pCOOH$, $C(O)(CH_2)_pCOOR^6$, $(CH_2)_p$phenyl where the phenyl is substituted with 0-3 R[1] groups, $C(O)CH(Ph)_2$, $C(O)CH_2$-(3PhO—)Ph, or R[5] is $(CH_2)_pOH$, $CH_2)_pO$-phenyl phenyl-[$(R_1)_m$phenyl], $(CH_2)$-phenyl-[$(R_1)_m$phenyl], or R[5] is $(CH_2)_p$—$N(C_{1-3}alkyl)$, phenyl, $(CH_2)_p$—$N(C_{1-3}alkyl)$, $(CH_2)_p$phenyl or R[5] is a 5 to 6 membered saturated or unsaturated heterocyclic group having 1 to 2 heteroatoms selected from O, S, and N, said heterocyclic group itself substituted with 0-2 R[1] groups, or R[5] is $SO_2$-alkyl of 1 to 6 carbons, $SO_2$-Ph where the phenyl is substituted with 0-3 R[1] groups or with $NH_2$, $NO_2$ or with $COOR^6$ group;

p is an integer having the values 1 to 4;

or $NR^5R^6$ is represented by the heterocyclic rings (i) through (iv) shown below where the dotted line represents the bond connecting the ring to the $(CH_2)_n$ group

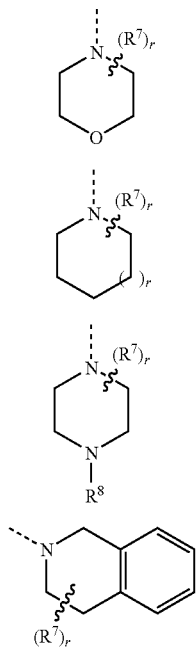

r is an integer having the values 0 to 3;

R$_6$ is H, alkyl of 1 to 6 carbons or phenyl substituted with 0-3 R[1] groups or with an OPh group, $(CH_2)_p$phenyl where the phenyl is substituted with 0-3 R[1] groups;

R[7] is F, Cl, Br, I, $(CH_2)_pOH$, phenyl where the phenyl is substituted with 0-3 R[1] groups, $(CH_2)_p$phenyl where the phenyl is substituted with 0-3 R[1] groups, $(CH_2)_p$piperidyl, alkyl of 1 to 6 carbons, COOH, $COOC_{1-6}$alkyl, $CONH_2$, $CONH(C_{1-6}alkyl)$, or $CON(C_{1-6}alkyl)_2$, one or two R[7] groups can be attached to the same ring carbon, R[8] is H, alkyl of 1 to 6 carbons, phenyl substituted with 0 to 3 R$_1$ groups, $(CH_2)_p$phenyl where the phenyl is substituted with 0 to 3 R$_1$ groups, $(CH_2)_p$cycloalkyl where the cycloalkyl group has 3 to 7 carbons, or R[8] is C(O)O-tert-Bu, The asterisk indicates a carbon which is asymmetric or maybe asymmetric, the wavy line represents a bond which can be of either R or S configuration, and a pharmaceutically acceptable salt of said compound.

The present invention also relates to pharmaceutical compositions suitable for administration to mammals, including humans, which include one or more compounds of the invention and are used for treatment of anthrax poisoning.

Biological Activity, Modes of Administration

Determining Biological Activity

As briefly noted above in the introductory section of this application for patent, the most serious, often lethal results of anthrax poisoning are caused by a toxin that is released by *bacillus anthracis* within the host. The toxin includes three proteins, one of which is a zinc-dependent metalloprotease enzyme (lethal factor) that cleaves near the N termini of several MAP kinase enzymes (MKKS) of the host. It is this disruption of key signaling pathways mediated by the host MKK enzymes that result in the severe and often lethal results of infection by the bacteria.

An assay for identifying and measuring the effectiveness of potential drugs to treat anthrax poisoning is based on measuring the inhibitory effect of the candidate compound on the lethal factor enzyme. The procedure used in the present invention to measure the potential efficiency of the compounds of the present invention is based, in a somewhat modified form, on the assay described by Cummings et al., A peptide-based fluorescence resonance energy transfer assay for *Bacillus anthracis* lethal factor protease, PNAS, May 14, 2002, Vol 99, No. 10 6603-6606, expressly incorporated herein by reference. The gist of this assay that a fluorogenic peptide substrate is incubated with the lethal factor enzyme in the presence of the inhibitor and the inhibition of the lethal factor is measured by measuring the fluorescence intensity of the cleaved substrate. A description of the actual assay conditions used for evaluating the compounds of the present invention is provided below.

Assay Procedure

Inhibitors were solubilized in 100% DMSO at 10 mM, then diluted to the final desired concentration and 10% final DMSO in the assay. Lethal factor protease (20 nM) and inhibitor were briefly incubated at room temperature in the assay buffer (20 mM Hepes, 0.05% Tween 20, 0.02% $NaN_3$, pH 7.4), and the reaction started by the addition of 12.5 μM final of the fluorogenic peptide substrate, MAPKKide™ (List Biological Laboratories, Inc, Campbell, Calif.). The final volume was 50 μL, in half area black microtiter plates (Costar). Fluorescence intensity (Ex: 320 nm, Em: 420 nm) was monitored for 15 minutes at room temperature (Gemini XS, Molecular Devices), and the $K_i^{app}$ values were calculated using the program BatchKi (BioKin Ltd., Pullman, Wash.). Generally speaking a compound is considered active in this assay if the calculated $K_i^{app}$ value is less than 300 (<300) μM.

Modes of Administration

The compounds of the invention are useful for treating anthrax poisoning. The compounds of this invention may be administered systemically through oral, intravenous or other modes of systemic administration, depending on such considerations as the severity of the anthrax infection treated, quantity of drug to be administered, and numerous other considerations. For oral administration the drug may be confected as a powder, pill, tablet or the like or as a syrup or elixir suitable for oral administration. For intravenous or intraperitoneal administration, the compound will be prepared as a solution or suspension capable of being administered by injection. In certain cases, it may be useful to formulate the compounds of the invention in suppository form or as extended release formulation for deposit under the skin or intramuscular injection. For each type of administration appropriate pharmaceutical excipients are likely to be added to the drug. The nature of such excipients for each type of systemic administration is well known in the art and need not be described here further.

A useful therapeutic or prophylactic concentration will vary from with the precise identity of the drug, with the severity of the anthrax infection being treated and the patient's susceptibility to treatment. Accordingly, no single concentration will be uniformly useful, but will require modification depending on the particularities of each situation. However, it is anticipated that an amount between 0.1 and 10 mg per kg of body weight per day will effect a therapeutic result.

Results of the Assay Measuring Lethal Factor Inhibitory Activity

Specific examples of compounds within the scope of the present invention are shown by their respective structural formulas in Tables 1 through 9, and their activity in the above-described assay is also indicated.

TABLE 1

| Compound # | R* | LF (FRET) $K_i^{app}$ (μM) |
|---|---|---|
| 167564 | 2-F—Ph | 52.4 |
| 167540 | 2-Me—Ph | 152 |
| 167456 | 3-F—Ph | 51.6 |
| 167491 | 3-Me—Ph | 176.5 |
| 167461 | 3-Cl—Ph | 87.4 |
| 167492 | 3-CF$_3$—Ph | >300 |
| 167458 | 3-MeO—Ph | 276 |
| 167157 | 4-F—Ph | 11.7 |
| 167460 | 4-Cl—Ph | 52.3 |
| 167511 | 4-CF$_3$—Ph | 240 |
| 167457 | 4-MeO—Ph | 192.5 |
| 167506 | 4-Ph—Ph | 85.1 |
| 167495 | 2,3-diMe—Ph | 269 |
| 167541 | 2,4-diMe—Ph | 134 |
| 167232 | 3-Me-4-F—Ph | 8.9 |
| 167463 | 3-F-4-Me—Ph | 65.6 |

TABLE 2

| Compound # | Configuration C2 | Configuration C4 | R³ | LF (FRET) $K_i^{app}$ (μM) |
|---|---|---|---|---|
| 167204 | — | R | H | 7.9 |
| 167205 | — | S | H | 225 |
| 167288 | R,S | R,S | Me[b] | 3.1 |
| 167297 | S | R | Me | 2.3 |
| 167432 | S | R | n-Pr | 1.57 |
| 167434 | S | R | —CH$_2$CH=CH$_2$ | 1.16 |
| 167433 | S | R | —CH2—cC3 | 1.4 |
| 167287 | R,S | R,S | n-Bu[d] | 9.7 |
| 167336 | S | R | n-Bu | 1.9 |
| 167353 | R | R | n-Bu | 5.8 |
| 167389 | R | S | n-Bu | 75.6 |
| 167390 | S | S | n-Bu | 224 |
| 167286 | R,S | R,S | —CH$_2$Ph[b] | 168 |
| 167285 | R,S | R,S | —CH$_2$Ph[c] | >300 |
| 167298 | S | R | —CH$_2$Ph | 89.5 |
| 167308 | R,S | R,S | —CH$_2$CH$_2$Ph[b] | 2.4 |
| 167337 | S | R | —CH$_2$CH$_2$CH$_2$Ph | 7.8 |
| 167395 | R | R | —CH$_2$CH$_2$CH$_2$Ph | 78.6 |
| 167341 | R | S | —CH$_2$CH$_2$CH$_2$Ph | 18 |
| 167408 | S | S | —CH$_2$CH$_2$CH$_2$Ph | >300 |
| 167354 | S | R | —CH$_2$CH=CHPh | 9.3 |
| 167371 | S | R | CH$_2$CH=CHCH(Ph)$_2$ | 14.0 |

[a] (—) = not determined
[b] Mixture of two syn-diastereomers
[c] Mixture of two anti-diastereomers
[d] Mixture of four diastereomers

TABLE 3

| Compound # | R** | LF (FRET) $K_i^{app}$ (μM) |
|---|---|---|
| 166976 | —OH | 138 |
| 167206 | (R)-OH | 66.1 |
| 167173 | —Oet | 171 |
| 167151 | —OCH$_2$Ph | 130 |
| 167366 | —Sme | 10.9 |

The compounds in Table 3 are racemic mixtures

TABLE 4

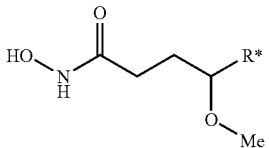

| Compound # | R³ | LF (FRET) $K_i^{app}$ (μM) |
|---|---|---|
| 167223 | H | 11.9 |
| 167675 | (S)-n-Pr | 2.6 |
| 167674 | (R)-n-Pr | 24 |

TABLE 4-continued

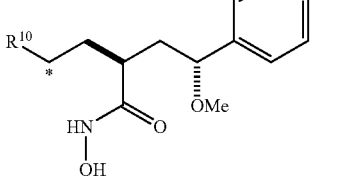

| Compound # | R³ | LF (FRET) $K_i^{app}$ (μM) |
|---|---|---|
| 167673 | (S)-CH₂CH=CH₂ | 6.6 |
| 167672 | (R)-CH₂CH=CH₂ | 42 |

TABLE 5

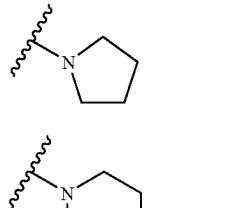

| Compound # | R⁵ | R⁶ | LF (FRET) $K_i^{app}$ (μM) |
|---|---|---|---|
| 167995 | Et | Et | 2.2 |
| 167784 | i-Pr | —CH₂Ph | 14.0 |
| 167796 | Ph | Ph | 2.1 |
| 167996 | —CH₂Ph | —CH₂Ph | 33.4 |

TABLE 6

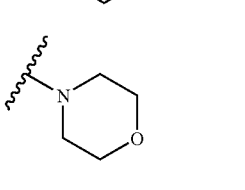

| Compound # | R⁵ | LF (FRET) $K_i^{app}$ (μM) |
|---|---|---|
| 167954 | Me— | 0.97 |
| 167922 | HOCH₂CH₂— | 1.49 |
| 167828 | n-Bu— | 1.1 |
| 168028 | Ph— | 1.82 |
| 168000 | 3-BrPh— | 2.8 |
| 168007 | 3-(3Me—4F—Ph)—Ph— | 19.5 |
| 168013 | 4-Br—Ph | 1.8 |
| 168038 | 4-(3Me—4F—Ph)—Ph— | 0.91 |
| 167785 | Ph—CH₂— | 2.0 |
| 168001 | 3-Br—Ph—CH₂— | 1.2 |
| 168003 | 3-(3Me—4F—Ph)—Ph—CH₂— | 2.3 |
| 167795 | 4-F—Ph—CH₂— | 2.1 |
| 168015 | 4-Br—Ph—CH₂— | 2.2 |
| 168037 | 4-(3Me—4F—Ph)—Ph—CH₂— | 0.68 |
| 167952 | Ph—CH₂CH₂— | 0.77 |
| 167953 | Ph—CH₂CH₂CH₂— | 0.23 |
| 167890 | Ph—O—CH₂CH₂— | 1.6 |
| 168058 | Ph—N(Me)—CH₂CH₂— | 0.78 |
| 168017 | (E)-Ph—CH=CH—CH₂— | 0.52 |
| 167892 | (3Me—4F—Ph)—CH₂CH₂CH₂— | 0.19 |
| 168082 | Ph(CH₂)₃—N(Me)—CH₂CH₂— | 0.82 |

TABLE 7

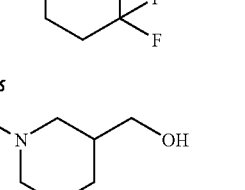

| Compound # | R¹⁰ | LF (FRET) $K_i^{app}$ (μm) |
|---|---|---|
| 167923 | 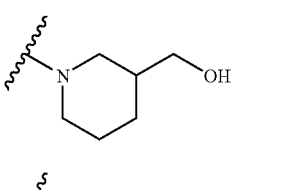 | 0.97 |
| 167889 | 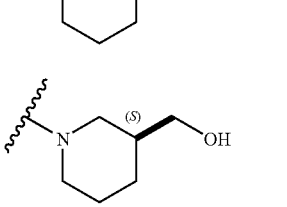 | 1.5 |
| 167829 | 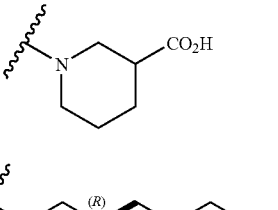 | 5.7 |
| 167884 |  | 2.2 |
| 167885 |  | 0.76 |
| 168059 |  | 0.60 |
| 168039 |  | 0.58 |
| 167924 |  | 9.0 |
| 168044 |  | 1.92 |

TABLE 7-continued

[Structure: R^10 group attached via * to a chain bearing C(=O)NHOH and CH2-CH(OMe)-(4-fluorophenyl)]

| Compound # | R^10 | LF (FRET) $K_i^{app}$ (µm) |
|---|---|---|
| 168045 | N-(3S)-(piperidin-1-ylmethyl)piperidin-1-yl | 0.43 |
| 167891 | 1,2,3,4-tetrahydroisoquinolin-2-yl | 0.92 |
| 167911 | azepan-1-yl | 69.5 |
| 167912 | azocan-1-yl | 284.5 |
| 167987 | 4-phenylpiperidin-1-yl | 0.76 |
| 167940 | 4-benzylpiperidin-1-yl | 0.4 |
| 167955 | piperazin-1-yl (NH) | 0.83 |
| 167944 | 4-Boc-piperazin-1-yl | 2.5 |

TABLE 7-continued

[Same parent structure]

| Compound # | R^10 | LF (FRET) $K_i^{app}$ (µm) |
|---|---|---|
| 167986 | 4-phenylpiperazin-1-yl | 2.22 |
| 167961 | 4-(cyclohexylmethyl)piperazin-1-yl | 1.8 |
| 167962 | 4-benzylpiperazin-1-yl | 1.9 |
| 167960 | 4-(4-fluoro-3-methylbenzyl)piperazin-1-yl | 0.97 |
| 167958 | 4-(2-phenylethyl)piperazin-1-yl | 2.4 |
| 167959 | 4-(3-phenylpropyl)piperazin-1-yl | 1.0 |

The dotted line represents the bond with which the nitrogen atom is connected to the carbon indicated with an asterisk.

TABLE 8

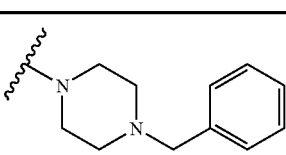

| Compound # | R⁵ | R⁶ | LF (FRET) $K_i^{app}$ (μM) |
|---|---|---|---|
| 168227 | —CH₂-cyclohexyl | H | 0.69 |
| 168229 | 4-F—Ph | H | 2.8 |
| 168137 | —CH₂-(4-F—Ph) | H | 0.70 |
| 168136 | —CH₂-(3-Me-4-F—Ph) | H | 0.19 |
| 168224 | —CH₂-4-(PhO)—Ph | H | 0.23 |
| 168230 | —CH₂-(4'-F-biphenyl-4-yl) | H | 0.45 |
| 168221 | —(CH₂)₂-(4-F—Ph) | H | 0.28 |
| 168222 | —(CH₂)₃-(4-F—Ph) | H | 0.17 |
| 168228 | —CH₂-2-(5-Me-furanyl) | H | 2.8 |
| 168223 | —CH₂-2-thienyl | H | 0.21 |
| 168231 | —CH₂-(benzo[b]thiophen-2-yl) | H | 0.32 |
| 168138 | —CH₂-(4-F—Ph) | Me | 0.39 |

TABLE 9

| Compound # | R¹⁰ | LF (FRET) $K_i^{app}$ (μM) |
|---|---|---|
| 168226 | (piperazinyl-benzyl) | 0.58 |

The dotted line represents the bond with which the nitrogen atom is connected to the carbon indicated with an asterisk.

GENERAL EMBODIMENTS AND SYNTHETIC METHODOLOGY

Definitions

The term alkyl refers to and covers any and all groups which are known as normal alkyl and branched-chain alkyl. Unless specified otherwise, lower alkyl means the above-defined broad definition of alkyl groups having 1 to 6 carbons in case of normal lower alkyl, and 3 to 6 carbons for lower branch chained alkyl groups. A pharmaceutically acceptable salt may be prepared for any compound used in accordance with the invention having a functionality capable of forming a salt, for example an acid or an amino functionality. A pharmaceutically acceptable salt is any salt which retains the activity of the parent compound and does not impart any deleterious or untoward effect on the subject to which it is administered and in the context in which it is administered.

Pharmaceutically acceptable salts may be derived from organic or inorganic bases. The salt may be a mono or polyvalent ion. Of particular interest are the inorganic ions, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Where there is a nitrogen sufficiently basic as to be capable of forming acid addition salts, such may be formed with any inorganic or organic acids. Preferred salts are those formed with inorganic acids such as hydrochloric acid, sulfuric acid or phosphoric acid. Any of a number of simple organic acids such as mono-, di- or tri-acid may also be used.

Some compounds used in accordance with the present invention may have trans and cis (E and Z) isomers. Unless specific orientation of substituents relative to a double bond or a ring is indicated in the name of the respective compound, and/or by specifically showing in the structural formula the orientation of the substituents relative to the double bond or ring the invention covers trans as well as cis isomers.

Some of the compounds used in accordance with the present invention may contain one or more chiral centers and therefore may exist in enantiomeric and diastereomeric forms. The scope of the present invention is intended to cover all isomers per se, as well as mixtures of cis and trans isomers, mixtures of diastereomers, pure enantiomers (optical isomers) and 50:50 (racemic) or other ratio mixtures of enantiomers as well. In some cases one compound of a diastereomeric species, or one specific enantiomer of a chiral compound is more active than the other diastereomer(s) or optical isomer, and when such a case is established it is indicated in the respective designation of the compound.

General Synthetic Methodology

The novel compounds used in accordance with the invention are encompassed by the general Formula 1 provided above.

A general route for the synthesis of the compounds of Formula 1 are shown in the General Schemes 1-6, below.

Specifically, the compounds of the invention where with reference to Formula 1 the variable X is O and R³ is hydrogen are made in accordance with General Scheme 1.

General Scheme 1

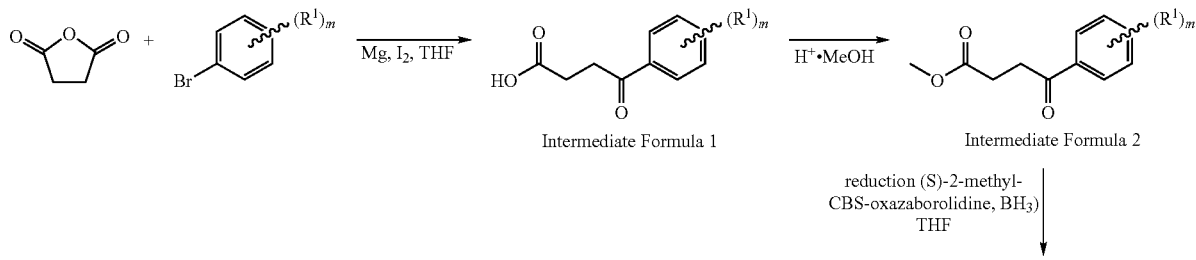

reduction (S)-2-methyl-CBS-oxazaborolidine, BH₃)
THF

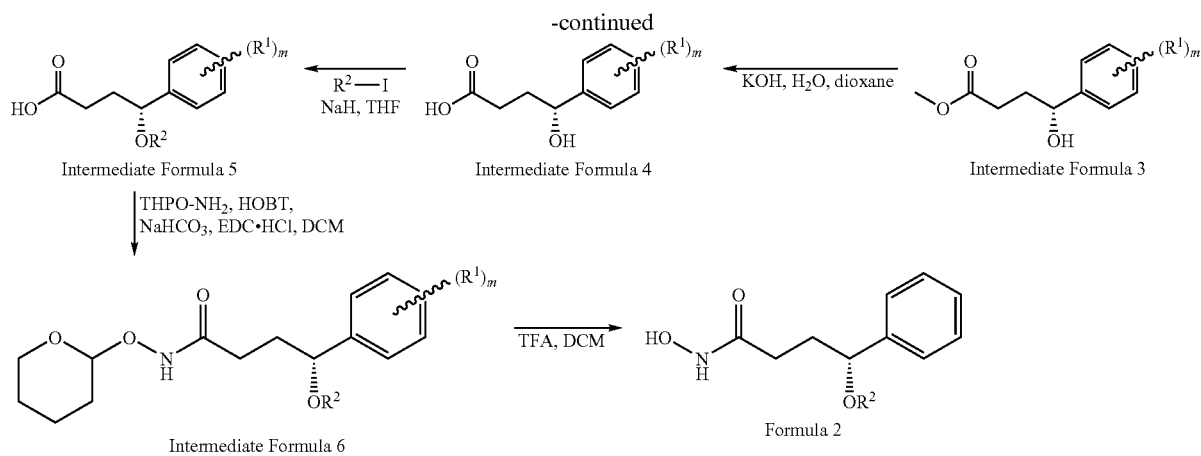

Intermediate Formula 5     Intermediate Formula 4     Intermediate Formula 3

Intermediate Formula 6     Formula 2

Referring now to General Scheme 1, a substituted bromo-benzene and succinic anhydride serve as starting materials. The variables $R^1$, m and $R^2$ are as defined in Formula 1. (Generally speaking throughout the description of the reaction schemes the variables shown in the schemes are defined as in Formula 1.) Such starting materials are either available commercially or can be obtained in accordance with known chemical scientific and or patent literature or by such modifications of known synthetic procedures which will be readily apparent to those skilled in the art.

The substituted bromo-benzene starting material is converted into a Grignard reagent and is reacted with the succinic anhydride in a suitable aprotic solvent, such as tetrahydrofuran (THF). The resulting gamma-keto-carboxylic acid of Intermediate Formula 1 is esterified to provide the corresponding methyl ester of Intermediate Formula 2. The gamma-keto function of the latter compound is reduced to a hydroxyl function to provide Intermediate Formula 3. The reaction scheme indicates a stereospecific or stereoselective reduction step which gives substantially only one of the two possible resulting chiral compounds. This reduction is performed with borane ($BH_3$) in the presence of (S)-2-methyl-CBS-oxazaborolidine in a suitable solvent, such as THF. It should be understood that if a non-stereospecific reduction were desired it could be performed with other reagents, such as $NaBH_4$.

The gamma-hydroxy-butyric acid ester compound of Intermediate Formula 3 is saponified to give the free acid of Intermediate Formula 4. Intermediate Formula 4 is then reacted with a halide compound of formula $R^2$—I in the presence of strong base, such as sodium hydride (NaH), to give the chiral gamma-ether compound of Intermediate Formula 5. The latter compound is reacted with tetrahydropyranyl-hydroxylamine (THPO—$NH_2$) in the presence of 1-hydroxybenzotriazole (HOBt), N-(dimethylaminopropyl)-N'-ethylcarbodiimide (EDC) in a solvent, such as dichloromethane (DCM) to give the tetrahydropyranyl protected derivative of the desired hydroxamic acids shown as Intermediate Formula 6. Intermediate Formula 6 is then treated with trifluoroacetic acid (TFA) in dichloromethane (DCM) to give compounds of Formula 2. The compounds of Formula 2 are within the scope of the invention and represent a subgenus of Formula 1.

General Reaction Scheme 2 discloses the synthesis of another subgenus of the compounds of Formula 1 wherein the variable X is O and $R^3$ is an alkyl group, such as the R—$(CH_2)_3$ group actually shown in the scheme where R represents alkyl of 1 to 5 carbons.

General Scheme 2

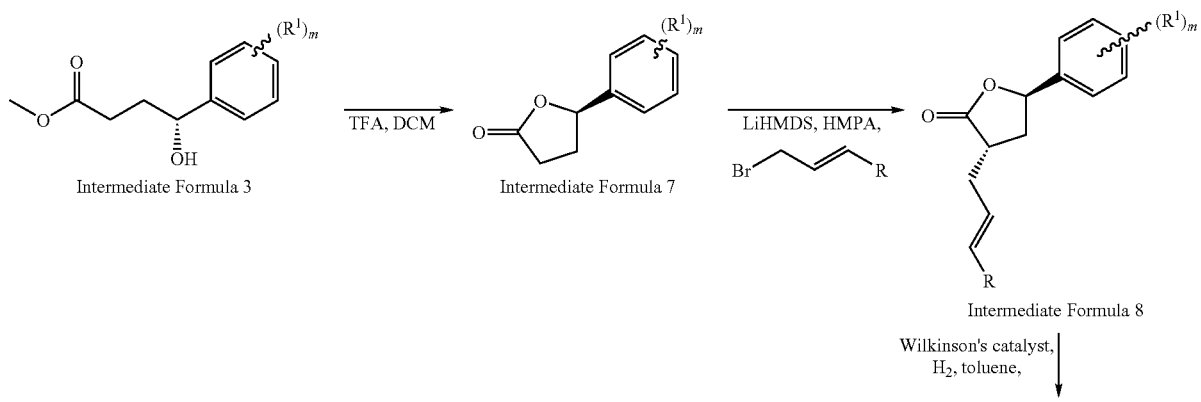

Intermediate Formula 3     Intermediate Formula 7     Intermediate Formula 8

Wilkinson's catalyst, $H_2$, toluene,

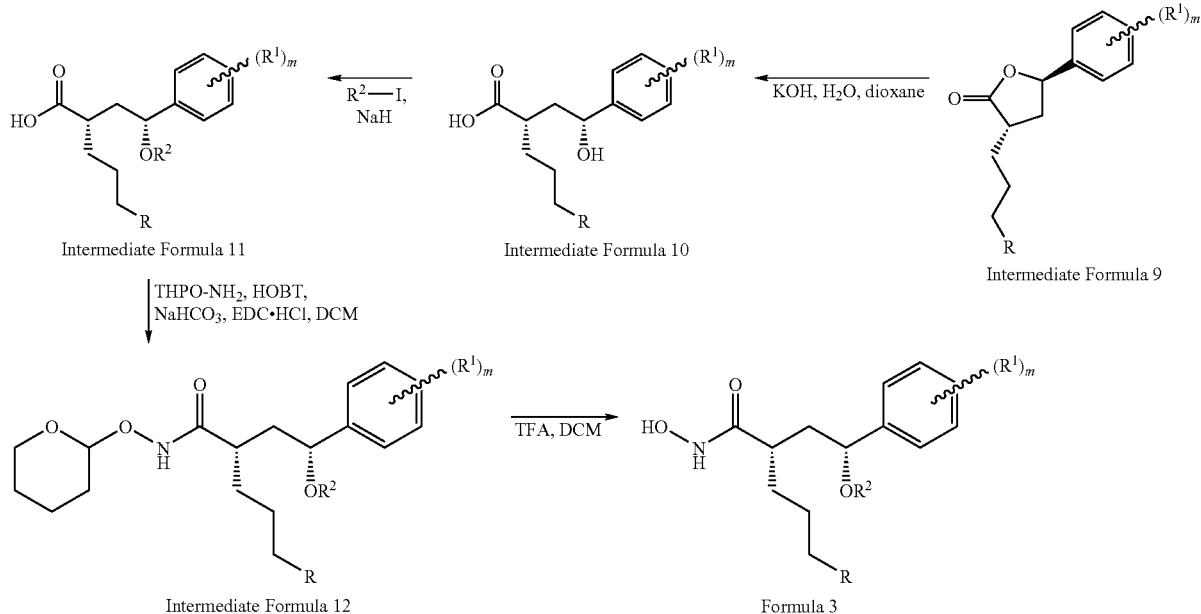

Referring now to General Scheme 2 the starting material is Intermediate Formula 3 which can be made in accordance with General Scheme 1. It should be understood in this regard that several 4-phenyl (or substituted phenyl) 4-oxo-butyric acids are commercially available and therefore several important compounds of Intermediate Formula 3 can be prepared from the commercially available "carboxylic acid" compound through esterification followed by reduction of the 4-oxo group as that reduction step is shown in General Scheme 1. In General Scheme 2 also as in Scheme 1 the result of the reduction step is shown as a single enantiomer, although it should be understood that by using other reagents such as NaBH$_4$ or other synthetic methods, such as one shown in General Reaction Scheme 3, a racemic mixture of the chiral compounds could be obtained and these could serve as starting compound in General Scheme 2.

As is shown in the scheme, the Intermediate Formula 3 is cyclized by treatment with trifluoroacetic acid (TFA) in dichloromethane (DCM) to give the compound of Intermediate Formula 7. Intermediate Formula 7 is then reacted with an alkyl or alkenyl halide in the presence of strong base, such as lithium bis(trimethylsilyl)amide (LiHMDS), in the presence of hexamethylphosphoramide (HMPA) to introduce an alkyl or alkenyl group alpha to the oxo group in the dihydrofuran-2(3H)-one moiety. This reaction is stereoselective due to the presence of the phenyl group which blocks one face of the lactone ring (see for example Fray, A. H. et al. *J. Org. Chem.* 1986, 51, 4828). General Scheme 2 shows this reaction with 1-bromo-but-2-ene to give the Intermediate Formula 8. The alkenyl bond of Intermediate Formula 8 is reduced with hydrogen gas in the presence of Wilkinson catalyst to give the corresponding butyl side chained compound of Intermediate Formula 9. It should be understood that instead of one-bromo-but-2-ene other alkyl bromides or appropriate alkenyl bromides can be used to introduce, after hydrogenation of the alkenyl group when applicable, the alkyl group shown as R$^3$ in Formula 1

The Intermediate of Formula 9 is then reacted with strong base, such as potassium hydroxide (KOH) to open the dihydrofuran-2(3H)-one ring to give the 2-butyl-4-(substituted phenyl)-4-hydroxy butyric acid of Intermediate Formula 11. Intermediate Formula 11 is then subjected to the same or substantially the same reaction steps as Intermediate Formula 4 is subjected in General Scheme 1 to give compounds of Formula 3. The compounds of Formula 3 are within the scope of the invention and represent subgenus of Formula 1.

General Reaction Scheme 3 discloses an alternative synthetic method to obtain Intermediate Formula 1 and also to obtain Intermediate Formula 3 and/or a racemic or close to racemic mixture of the compound corresponding to Intermediate Formula 3 identified as Intermediate Formula 14.

General Scheme 3

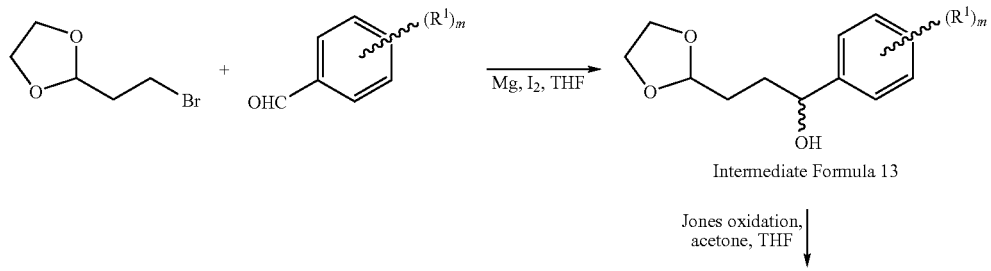

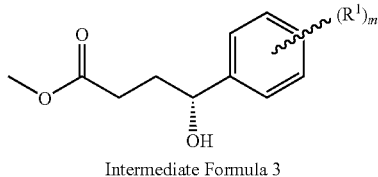

Intermediate Formula 3

1. esterification
2. reduction (S)-2-methyl-CBS-oxazaborolidine BH₃) THF

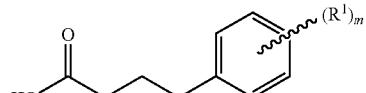

Intermediate Formula 1

|NaBH₄

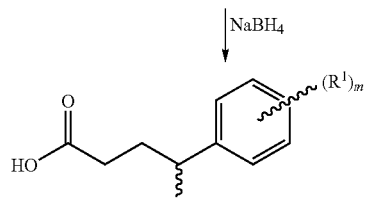

Intermediate Formula 14

Referring now to General Scheme 3 2-(2-bromoethyl)-[1,3]dioxolane is converted into a Grignard reagent and reacted with benzaldehyde or substituted benzaldehyde. The latter compounds are either available commercially or can be obtained in accordance with the chemical literature or by such modifications of known literature procedures which will be readily apparent to those skilled in the art. The hydroxyl function of the resulting Intermediate Formula 13 is converted to a keto function by Jones oxidation to give the compounds of Intermediate Formula 1. The latter compounds can be reduced by a non-selective hydrogenation method to give a racemic or closely racemic mixture shown as Intermediate Formula 14. Intermediate Formula 14 can serve as a starting material in the series of reactions shown in General Scheme 2. After esterification Intermediate Formula 1 can also be reduced in a stereoselective manner, as shown in General Scheme 2 to provide Intermediate Formula 3 that serves as intermediate in the synthetic sequence shown both in General Scheme 1 and General Scheme 2.

General Scheme 4 discloses the synthesis of another subgenus of the compounds of Formula 1 wherein the variable X is O and $R^3$ is an allyl or related group. R in this scheme represents H or an alkyl or substituted alkyl group.

General Scheme 4

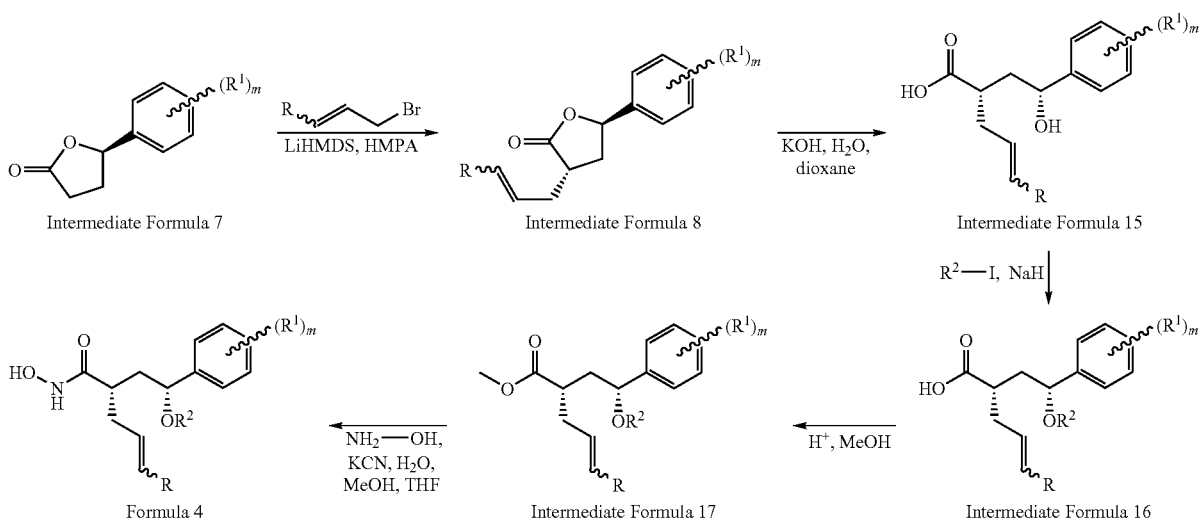

In accordance with this scheme Intermediate Formula 7 that can be obtained as shown in General Scheme 2 is reacted with allyl bromide in the presence of strong base (lithium bis(trimethylsilyl)amide (LiHMDS)) and HMPA to introduce an allyl group alpha to the oxo group in the dihydrofuran-2(3H)-one moiety to give Intermediate Formula 8. Thereafter, the dihydrofuranone ring is opened by treatment with strong base to give Intermediate Formula 15. The $R^2$ group is introduced into the latter compound by reaction with an alkyl halide of the formula $R^2$—I in the presence of strong base to provide Intermediate Formula 16. Intermediate Formula 16 is esterified to give Intermediate Formula 17, and the latter is converted into the hydroxamic acid compound of Formula 4 by reaction with hydroxylamine ($NH_2OH$) potassium cyanide (KCN) in water and methanol. The compounds of Formula 4 are within the scope of the invention and represent a subgenus of the compounds of Formula 1.

General Scheme 5

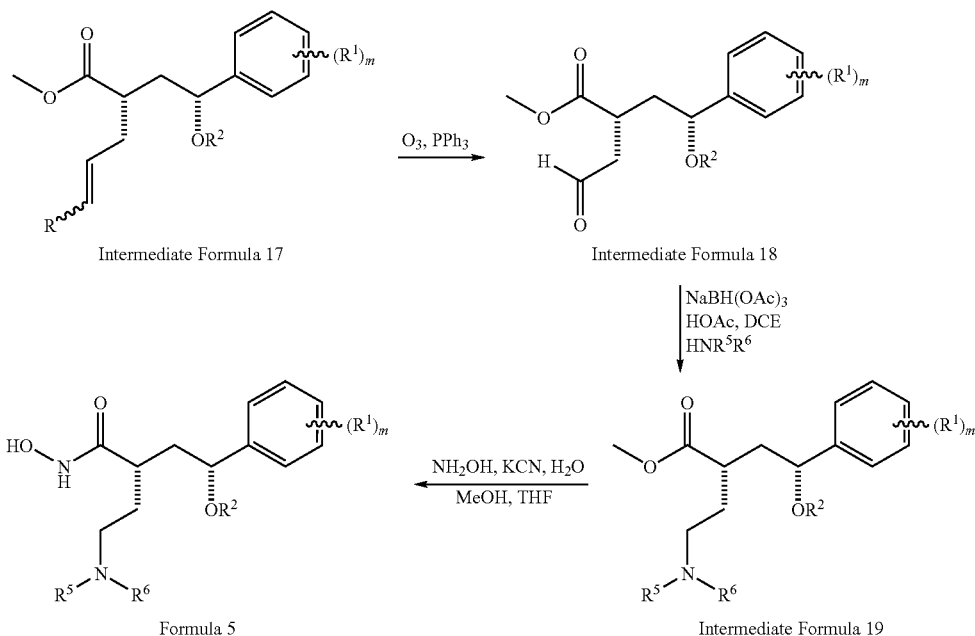

Intermediate Formula 17 → Intermediate Formula 18 → Intermediate Formula 19 → Formula 5

General Scheme 5 discloses the synthesis of still another subgenus of the compounds of Formula 1 where the variable X is O and $R^3$ is represented by $R^5R^6N-CH_2CH_2-$. In accordance with this scheme Intermediate Formula 17 (available as shown in Reaction Scheme 4) is oxidized with ozone ($O_3$) in the presence triphenylphosphine ($PPh_3$) to give Intermediate Formula 18 where there is a $CH_2CHO$ group on carbon number 2 of the butanoic acid chain. Intermediate Formula 18 is then reacted with $NaBH(OAc)_3$ and an amine of the formula $HNR^5R^6$ in the presence of acetic acid and DCE to five Intermediate Formula 19. The latter compound is converted into the hydroxamic acid of Formula 5 by treatment with hydroxylamine and potassium cyanide, as described above in other reaction schemes. The compounds of Formula 5 are within the scope of the invention and represent a subgenus of the compounds of Formula 1.

General Scheme 6

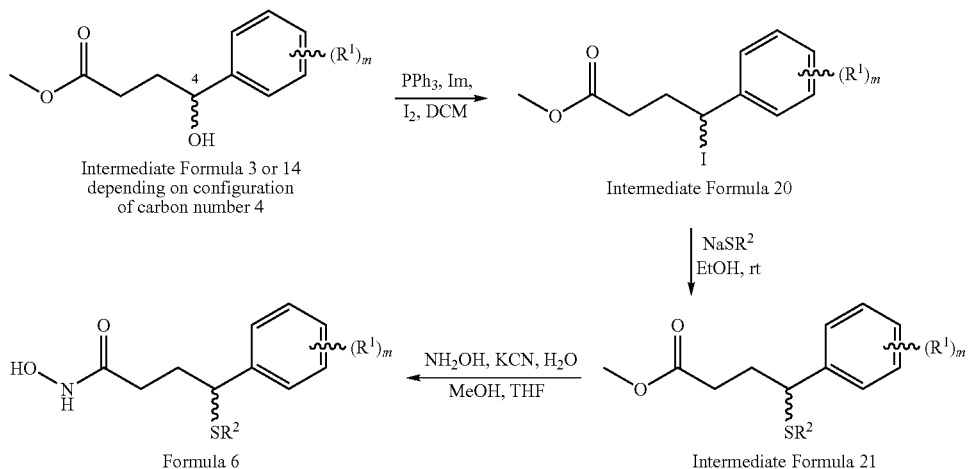

Intermediate Formula 3 or 14 depending on configuration of carbon number 4 → Intermediate Formula 20 → Intermediate Formula 21 → Formula 6

General Scheme 6 discloses the synthesis of still another subgenus of the compounds of Formula 1 where the variable X is S and $R^3$ is H. In accordance with this scheme the Intermediate of Formula 3 or of Formula 14 (depending on stereospecificity) is reacted with iodine in the presence of triphenylphosphine, imidazole (Im) and DCM to replace the hydroxyl group on carbon number 4 of the butanoic acid ester chain and give Intermediate Formula 20. Intermediate Formula 20 is reacted with the sodium salt of a thiol compound of the formula $NaSR^2$ to give Intermediate Formula 21. The latter is converted into the compounds of the invention of Formula 6 by steps described above in connection with other reaction schemes. The compounds of Formula 6 are within the scope of the invention and represent a subgenus of the compounds of Formula 1.

A modification of Reaction Scheme 6 provides compounds of the invention within the scope of Formula 1 where the X is S and $R^3$ is not hydrogen. In this modification (not specifically shown as a reaction scheme) Intermediate Formula 15 (shown in General Scheme 4) is converted into an ester, for example by treatment with methanol and HCl, The resulting ester is then subjected to the reaction steps shown in General Scheme 6 starting with iodine in the presence of triphenylphosphine imidazole and DCM to provide another subgenus of the compounds of the invention.

General Scheme 7 discloses the presently preferred synthetic route to yet another subgenus of the compounds of the invention, particularly but not exclusively those which are shown in Table 8 and analogous to Table 7 but with four (4) rather than two (2) carbons in the side chain before the $NR^5R^6$ moiety. With reference to Formula 1 in these compounds the $R^3$ group is $(CH_2)_nNR^5R^6$, and n is 4. The starting material is Intermediate Formula 7 that can be obtained as is described in General Scheme 2.

As is shown in the scheme, Intermediate Formula 7 is reacted with 4-benzyloxy-1-iodo-but-2,3-ene in the presence of strong base, such as lithium bis(trimethylsilyl)amide (LiHMDS) in an aprotic solvent, such as THF to give Intermediate

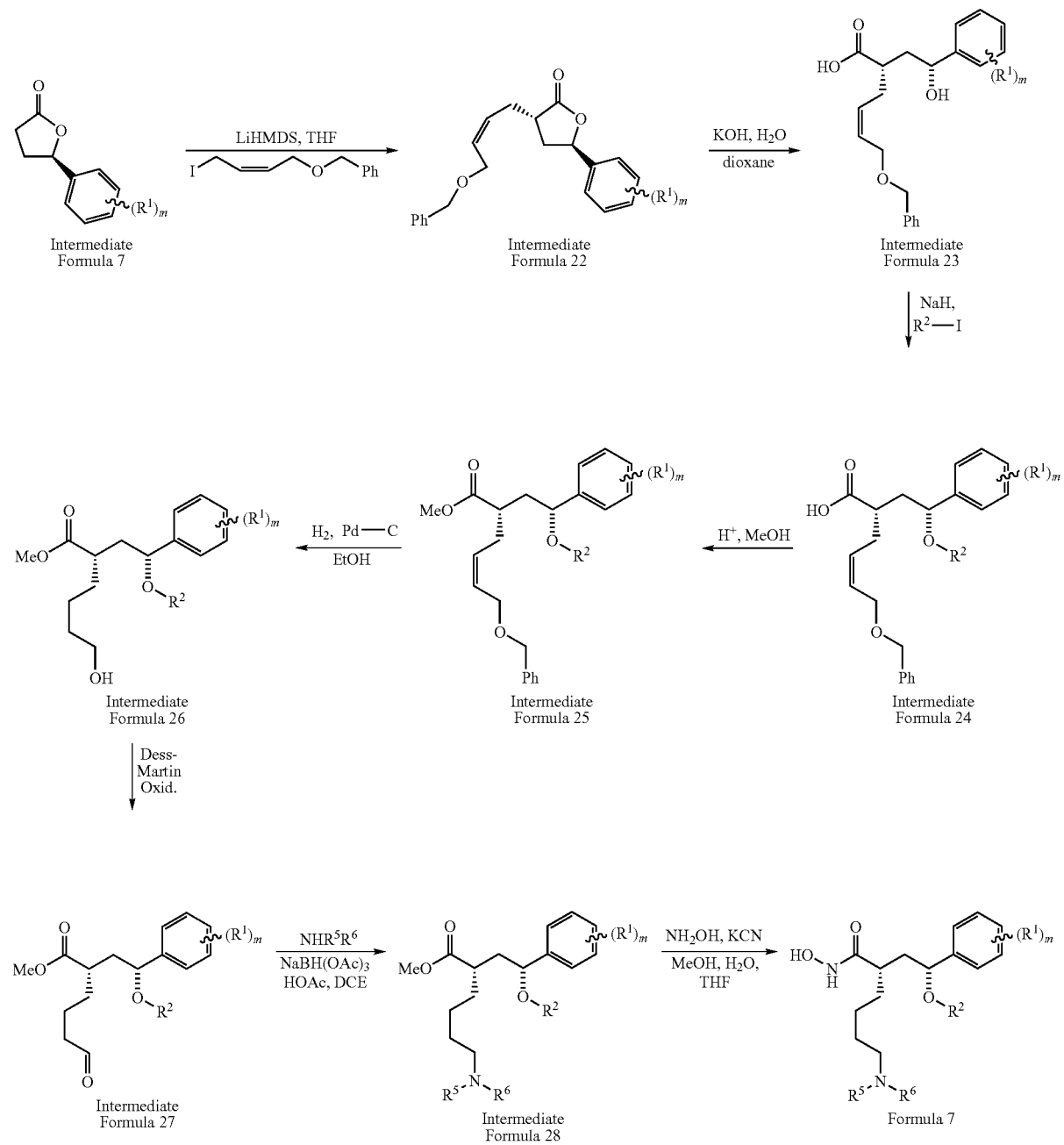

Formula 22. Intermediate Formula 22 is then reacted with strong base to open the 2-oxo-furan ring and provide Intermediate Formula 23. The hydroxyl group of Intermediate Formula 23 is etherified by treatment with a reagent of the formula $R^2$—I in the presence of strong base, such as sodium hydride. An example for the reagent $R^2$—I is methyl iodide. The resulting Intermediate Formula 24 is then esterified in methanol (or other alkanol) in the presence of acid to provide Intermediate Formula 25. The olephinic bond in the side chain of Intermediate Formula 25 is removed by hydrogenation to give Intermediate Formula 26. The hydroxyl group of the latter is oxidized using for example 1,1,1-tris(acetyloxy)-1,1-dihydro-1,2-benziodoxol-3-(1H)-one (Dess-Martin periodane) to give an aldehyde of Intermediate Formula 27. Intermediate Formula 27 is then reacted with an amine of the formula $NHR^5R^6$ and the resulting intermediate is reduced with sodium triacetoxyborohydride $NaBH(OAc)_3$ to provide the amine compound of Intermediate Formula 28. Intermediate Formula 28 is converted into the compounds of the invention of Formula 7 by steps described above in connection with other reaction schemes. The compounds of Formula 7 are within the scope of the invention and represent a subgenus of the compounds of Formula 1.

General Scheme 8

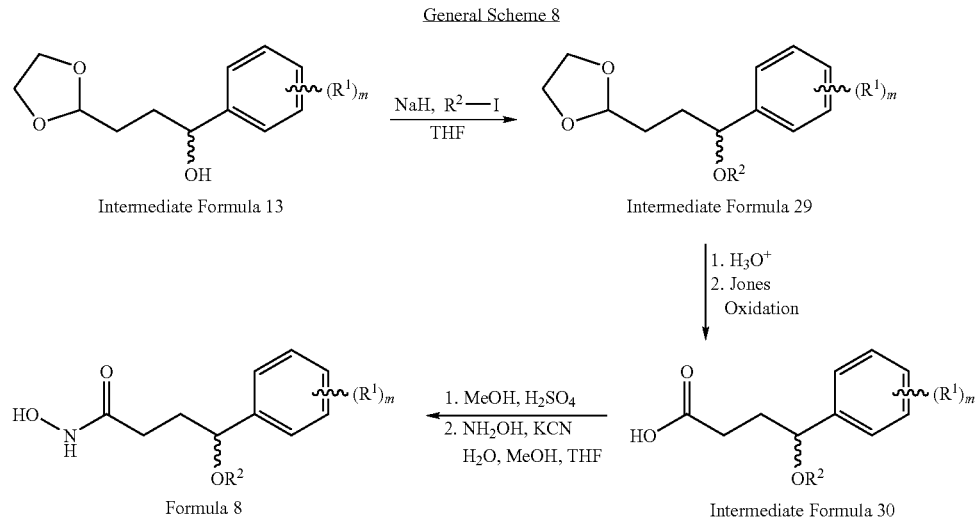

General Scheme 8 discloses a generally preferred route for the synthesis of compounds in Table 1. Intermediate Formula 13 (obtained as shown in General Scheme 3) is reacted in the presence of strong base (NaH) with an agent of the formula $R^2$—I where the variable $R^2$ is defined as in connection with Formula 1, but specifically for the compounds of Table 1 $R^{24}$ is methyliodide. The resulting Intermediate Formula 29 is subjected to treatment with acid and then Jones oxidation to give Intermediate Formula 30. Intermediate Formula 30 is then converted to the corresponding methyl ester by treatment with methanol and acid and the resulting ester is converted into the hydroxamic acid of Formula 8 by treatment with hydroxylamine and potassium cyanide, as described above in other reaction schemes. The compounds of Formula 8 are within the scope of the invention and represent a subgenus of the compounds of Formula 1.

General Scheme 9

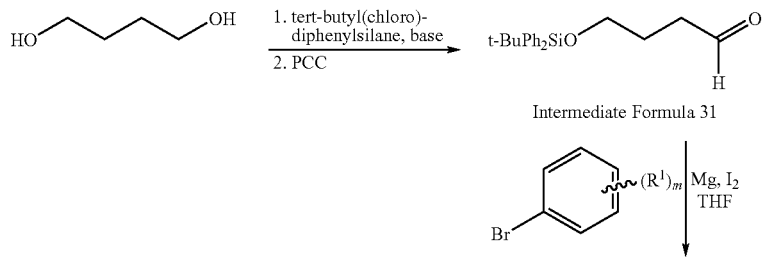

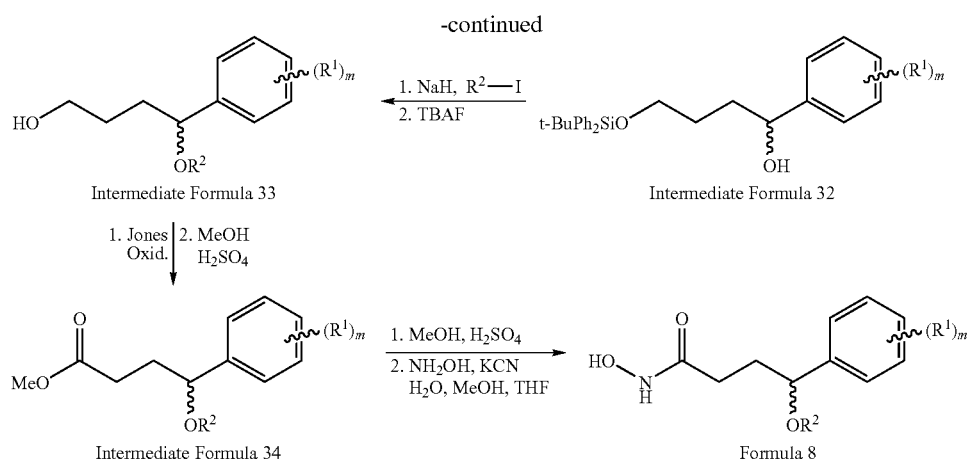

General Scheme 9 discloses a still another generally preferred route for the synthesis of compounds in Table 1. In accordance with this scheme one hydroxyl group of 1,4-butanediol is reacted with a silylating agent, such as tert-butyl(chloro) diphenylsilane and then oxidized with pyridinium chlorochromate (PCC) to provide Intermediate Formula 31. Intermediate Formula 31 is then reacted with a Grignard reagent derived from the compound having the formula $(R^1)_m$phenyl-Br (or the corresponding iodide) to provide Intermediate Formula 32. $R^1$ is defined as in connection with Formula 1. Intermediate Formula 32 is then reacted in the presence of strong base (NaH) with an agent of the formula $R^2$—I where the variable $R^2$ is defined as in connection with Formula 1, but specifically for the compounds of Table 1 $R^2$—I is methyliodide. The tert-butyldiphenylsilyl protecting group is then removed by treatment with tetrabutylammonium fluoride (TBAF) to give Intermediate Formula 33. Intermediate Formula 33 is then subjected to Jones oxidation followed by esterification to give Intermediate Formula 34. Intermediate Formula 34 is converted into the hydroxamic acid of Formula 8 by treatment with hydroxylamine and potassium cyanide, as described above in other reaction schemes.

Preferred Examples

Referring now to the variable $R^1$ in Formula 1, in the compounds of the invention $R^1$ represents a substituent on the phenyl group shown in the formula. In the preferred compounds of the invention $R^1$ is F, $CF_3$, Cl, methyl, or methoxy. The variable m is preferably the integer selected from 1, 2 and 3. Even more preferably the variable m is 1 or 2. Particularly preferred are compounds of the invention where m is 1 and $R^1$ is fluoro in a position para to the side chain of the phenyl moiety. Also particularly preferred are compounds where m is 2, and the $R^1$ groups are methyl and fluoro, with the methyl group being in the 3 (meta) position and the fluoro being in the 4 (para) position relative to the side chain.

The variable X in the preferred compounds of the invention is O or S; in the majority of the presently preferred compounds X is O.

Referring now to the variable $R^2$ in Formula 1 in the preferred compounds of the invention $R^2$ is H, alkyl of 1 to 3 carbons, or alkylphenyl where the alkyl group has 1 to 3 carbons. Even more preferably $R^2$ is methyl, or benzyl. In the preferred compounds of this group the phenyl group, where applicable, is either unsubstituted or has only a single substituent selected from the preferred $R^1$ groups.

Referring now to the variable $R^3$ of Formula 1 compounds this variable preferably represents H, alkyl of 1 to 6 carbons, alkenyl of 1 to 4 carbons, alkyl-phenyl and alkenylphenyl where the alkyl or alkenyl group has 1 to 4 carbons, or alkenyl (phenyl)$_2$ where the alkenyl group has 4 carbons. The following are also preferred examples of the variable $R^3$: $(CH_2)_n NHR^5$ where n is 2 or 4, and $(CH_2)_n NR^5R^6$ where n is 2 or 4. When $R^3$ is $(CH_2)_n NR^5R^6$ and n is 4 then particularly preferred are compounds where $NR^5R^6$ represents a heterocyclic ring.

The most preferred compounds of the invention are shown in Tables 1 through 8 above, and are also shown and disclosed below with their characteristic data such as nmr, mass spectrometry and optical rotation, as applicable.

Experimental

Schemes and experimental descriptions for the synthesis of the specific exemplary compounds of the invention are provided below. The LC/MS data given was obtained using the following conditions: LC/MSD/ELSD analysis performed in ESI positive mode with an Agilent 1100 LC/MSD VL system equipped with Agilent 1100 HP PDA and Sedex 75 ELSD detectors. Column: Zorbax Eclipse SD-C18, 5 μm, 4.6×75 mm; Temperature set at 25° C.; Mobile Phase: % A=0.025% trifluoroacetic acid-water, % B=0.025% trifluoroacetic acid-acetonitrile; or % A=0.10 formic acid-water, % B=0.10 formic acid-acetonitrile Linear Gradient: 20%-98% B in 15 min.; Flow rate: 1.0 mL/min.; ELSD gain set @ 3; UV set at 254 nm and 214 nm.

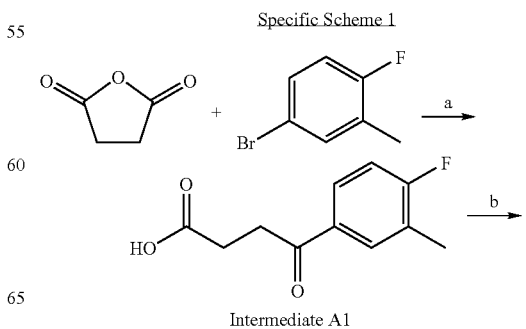

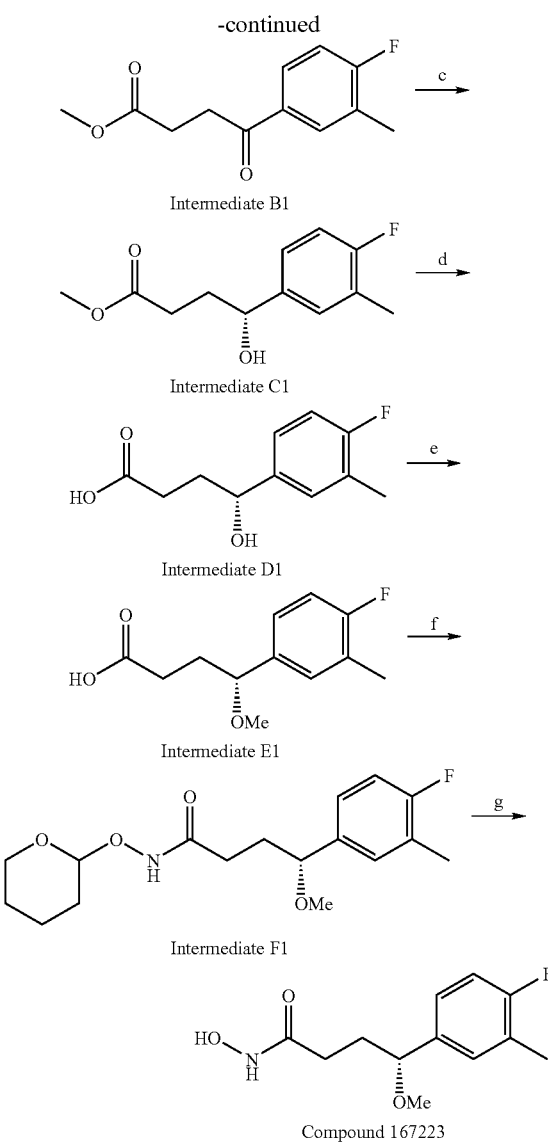

Compound 167223

Reagents and conditions: a) Mg, I₂, THF, -30-60° C., 3 h; b) conc. H₂SO₄, MeOH, 25° C., 12 h; c) (S)-2-methyl-CBS-oxazaborolidine, BH₃, THF, 25° C., 30 min; d) KOH, H₂O, dioxane, 25° C., 30 min; e) MeI, NaH, THF, 25° C., 3 h; f) THPO-NH₂, HOBt, NaHCO₃, EDC·HCl, DCM, 25° C., 3 h; g) TFA, DCM, 25° C., 30 min.

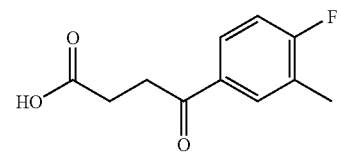

4-(4-fluoro-3-methylphenyl)-4-oxobutanoic acid (Intermediate A1)

To an oven dried three neck flask was added Mg turnings (355 mg, 14.6 mg-at.) catalytic amount of iodine, and 20 mL THF. To the resulting mixture was added dropwise 4-bromo-1-fluoro-2-methyl-benzene (1.0 g, 0.005 mol) with heating to ~62° C. After completing the addition of the aryl bromide, the mixture was stirred for an additional 30 min at 62° C. The THF solution of the prepared aryl magnesium bromide was cooled to -70° C. and succinic anhydride (1.0 g, 0.01 mmol) added as a solution in 10 mL THF. The mixture was vigorously stirred with warming to rt over 3 h and then hydrolyzed by the addition of 30 mL of 1M HCl. The resulting mixture was extracted with ethyl acetate (2×20 mL). The combined organic layers were extracted with 5% aqueous K₂CO₃ (3×10 mL) and the combined aqueous layers acidified with 1M HCl to pH3. A milky colloidal suspension was extracted with ethyl acetate (3×30 mL) and the combined organic layers washed with brine (2×20 mL). The solvent was evaporated under reduced pressure and the crude product used directly in the next step without further purification.

LC/MS: $t_R$=6.0 min. MS (API-ES) m/z 211 (M+H⁺).

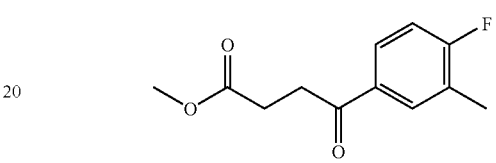

Methyl 4-(4-fluoro-3-methylphenyl)-4-oxobutanoate (Intermediate B1)

To the crude 4-(4-fluoro-3-methyl-phenyl)-4-oxo-butyric acid in 50 mL methanol was added 500 µL concentrated H₂SO₄ at 25° C. After stirring for 16 h, the mixture was concentrated under reduced pressure and 50 mL water was added. The mixture was extracted with ethyl acetate (3×50 mL) and the combined organic layers washed with brine (2×30 mL) and the product isolated using silica gel chromatography to afford 1.2 g of the title compound as a colorless oil.

LC/MS: $t_R$=7.8 min. MS (API-ES) m/z 225 (M+H⁺).

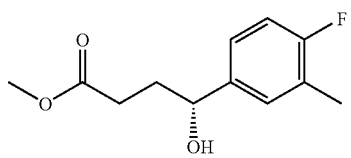

(R)-Methyl 4-(4-fluoro-3-methylphenyl)-4-hydroxybutanoate (Intermediate C1)

A solution of BH₃.THF (1M, 1.2 mL, 1.2 mmol) was added to 10 mL anhydrous THF followed by the dropwise addition of (S)-2-methyl-CBS-oxazaborolidine (1M, 109 µL, 0.1 mmol) in toluene at 25° C. After stirring for 5 min, methyl 4-(4-fluoro-3-methylphenyl)-4-oxobutanoate (229 mg, 1.0 mmol) was slowly added as a solution in 5 mL THF. The mixture was stirred for 30 min at room temperature and then the reaction was quenched by the careful addition of saturated aqueous ammonium chloride (10 mL). The resulting mixture was extracted with ethyl acetate (3×20 mL) and the combined organic layers washed with brine (2×10 mL) before being dried over Na₂SO₄. The solvents were removed under reduced pressure and the product isolated by silica gel chromatography to afford the title compound 181 mg, as an oil.

LC/MS: $t_R$=6.6 min. MS (API-ES) m/z 210 (M+H⁺—H₂O).

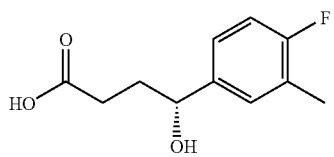

(R)-4-(4-Fluoro-3-methyl-phenyl)-4-hydroxy-butanoic acid (Intermediate D1)

To a solution of (R)-Methyl 4-(4-fluoro-3-methylphenyl)-4-hydroxybutanoate (181 mg, 0.80 mmol) in 5 mL dioxane was added 5 mL aqueous 5% KOH at 25° C. The mixture was stirred for 30 min at room temperature and then the reaction quenched by the addition of 10 mL of 1M HCl and the resulting mixture extracted with ethyl acetate (2×10 mL). The combined organic layers were extracted with 5% $K_2CO_3$ (3×5 mL) and the aqueous extracts acidified with 1M HCl to pH3. The resulting white colloidal suspension was extracted with ethyl acetate (3×20 mL) and the combined organic layers washed with brine (2×15 mL) before being dried over $Na_2SO_4$. The solvent was evaporated under reduced pressure and the crude product (233 mg) was used in the next step without further purification.

LC/MS: $t_R$=5.0 min. MS (API-ES) m/z 235 (M+H$^+$+Na$^+$).

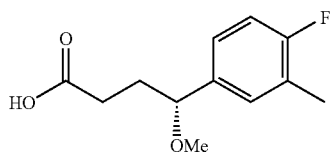

(R)-4-(4-Fluoro-3-methylphenyl)-4-methoxybutanoic acid (Intermediate E1)

To the suspension of NaH (373 mg of a 60% dispersion in mineral oil, 9.3 mmol) in 20 mL THF was slowly added (R)-4-(4-Fluoro-3-methyl-phenyl)-4-hydroxy-butanoic acid as a solution in 10 mL THF at 25° C. Methyl iodide (974 mg, 6.9 mmol, 427 µL) was then added dropwise to the mixture. The resulting mixture was stirred for 3 h at room temperature and then the reaction was quenched by the addition of 20 mL of 1M HCl. The mixture was and extracted with ethyl acetate (3×30 mL) and the combined organic layers washed with brine (2×20 mL) and dried over sodium sulfate. Evaporation of solvent left the crude product as an oil which was used in the next step without further purification.

LC/MS: $t_R$=6.8 min. MS (API-ES) m/z 249 (M+H$^+$+Na$^+$).

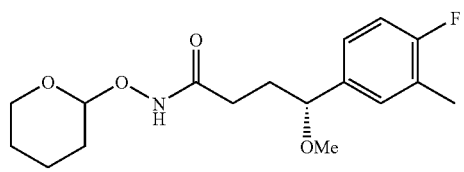

(4R)-4-(4-fluoro-3-methylphenyl)-4-methoxy-N-(tetrahydro-2H-pyran-2-yloxy)butanamide (Intermediate F1)

To a mixture of O-(tetrahydro-2H-pyran-2-yl)hydroxylamine (175 mg, 1.5 mmol), HOBt (810 mg, 6.0 mmol), NaHCO$_3$ (1.0 g, 11.9 mmol) and the crude (R)-4-(4-fluoro-3-methylphenyl)-4-methoxybutanoic acid in 60 mL CH$_2$Cl$_2$ was added EDC.HCl (958 mg, 5.0 mmol). The mixture was stirred for 3 h at 25° C. The solvent was removed under reduced pressure and the product isolated by flash column chromatography, eluting with 10% to 60% Ethyl acetate/Hexane gradient solvent to give 208 mg of the title compound.

LC/MS: $t_R$=7.0 min. MS (API-ES) m/z 326 (M+H$^+$).

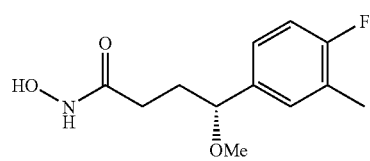

(R)-4-(4-fluoro-3-methylphenyl)-N-hydroxy-4-methoxybutanamide (Compound 167223)

To the solution of 4R)-4-(4-fluoro-3-methylphenyl)-4-methoxy-N-(tetrahydro-2H-pyran-2-yloxy)butanamide (66 mg, 0.2 mmol) in 4 mL DCM was slowly added 2 mL TFA and the resulting solution stirred for 30 min at 25° C. The solvent was evaporated and the product isolated by flash column chromatography eluting with 0% to 10% methanol/DCM gradient solvent to give 32 mg of the title compound as a white solid.

1H NMR (CD$_3$OD): δ 7.12 (dd, 2H, J=7.9 and 16.8), 7.00 (t, 1H, J=9.18), 4.10 (dd, 1H, J=5.6 and 7.7), 3.17 (s, 3H), 2.26 (s, 3H), 2.13 (t, 2H, J=7.4), 2.04-1.81 (m, 2H).

LC/MS: $t_R$=4.9 min. MS (API-ES) m/z 264 (M+H$^+$+Na$^+$).

Specific Scheme 2

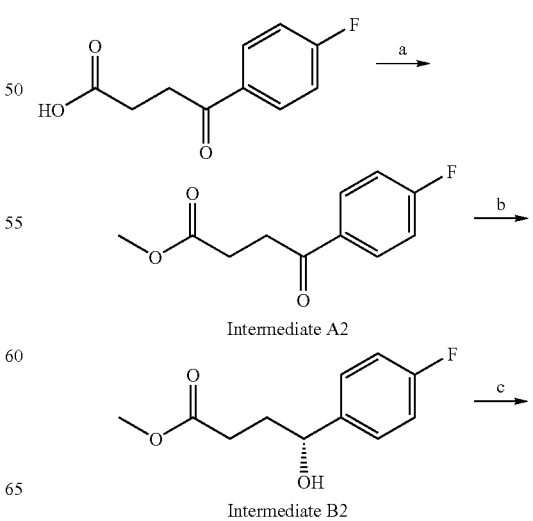

Intermediate A2

Intermediate B2

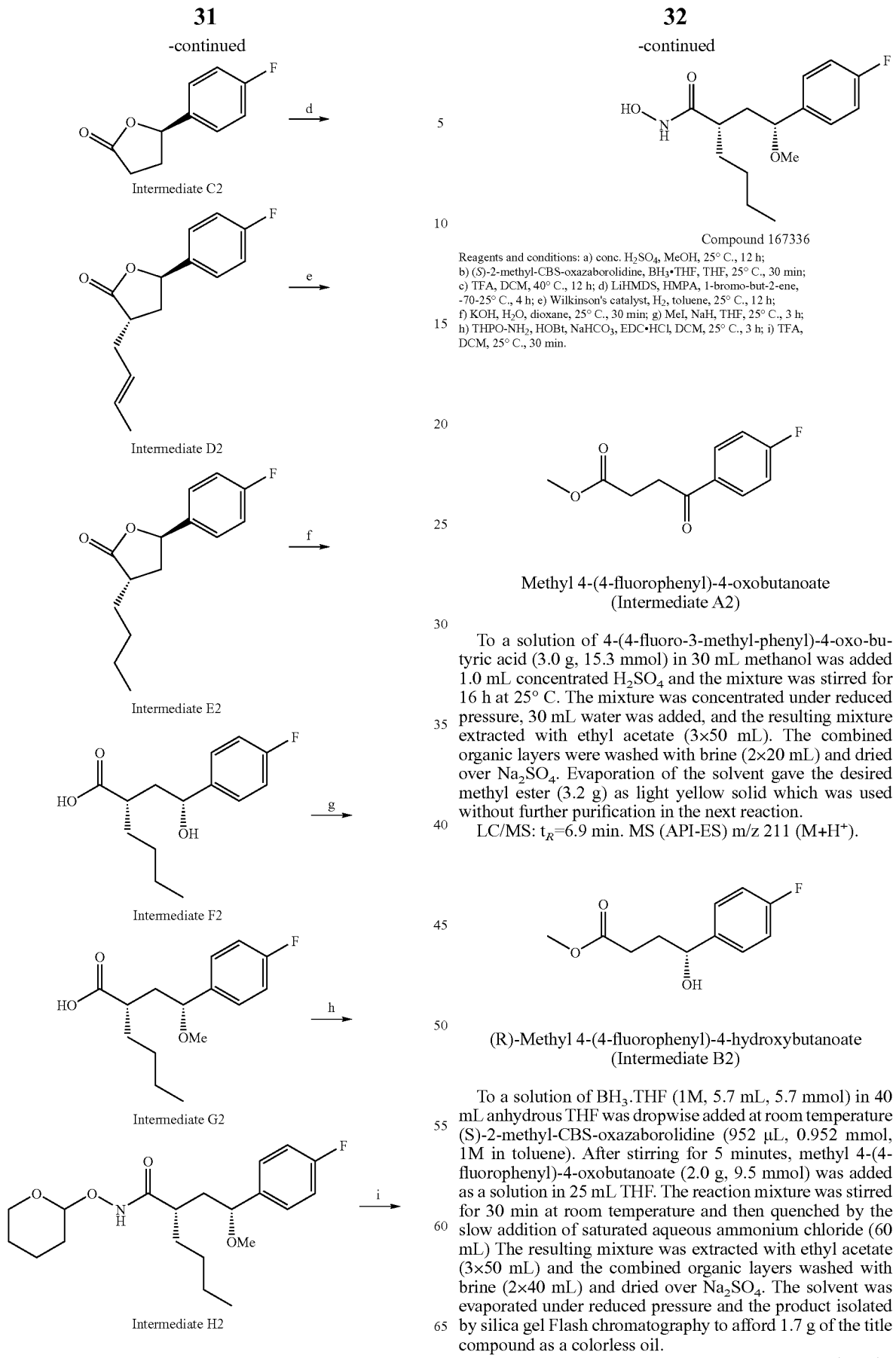

Reagents and conditions: a) conc. H$_2$SO$_4$, MeOH, 25° C., 12 h;
b) (S)-2-methyl-CBS-oxazaborolidine, BH$_3$•THF, THF, 25° C., 30 min;
c) TFA, DCM, 40° C., 12 h; d) LiHMDS, HMPA, 1-bromo-but-2-ene,
-70-25° C., 4 h; e) Wilkinson's catalyst, H$_2$, toluene, 25° C., 12 h;
f) KOH, H$_2$O, dioxane, 25° C., 30 min; g) MeI, NaH, THF, 25° C., 3 h;
h) THPO-NH$_2$, HOBt, NaHCO$_3$, EDC•HCl, DCM, 25° C., 3 h; i) TFA,
DCM, 25° C., 30 min.

Methyl 4-(4-fluorophenyl)-4-oxobutanoate (Intermediate A2)

To a solution of 4-(4-fluoro-3-methyl-phenyl)-4-oxo-butyric acid (3.0 g, 15.3 mmol) in 30 mL methanol was added 1.0 mL concentrated H$_2$SO$_4$ and the mixture was stirred for 16 h at 25° C. The mixture was concentrated under reduced pressure, 30 mL water was added, and the resulting mixture extracted with ethyl acetate (3×50 mL). The combined organic layers were washed with brine (2×20 mL) and dried over Na$_2$SO$_4$. Evaporation of the solvent gave the desired methyl ester (3.2 g) as light yellow solid which was used without further purification in the next reaction.

LC/MS: $t_R$=6.9 min. MS (API-ES) m/z 211 (M+H$^+$).

(R)-Methyl 4-(4-fluorophenyl)-4-hydroxybutanoate (Intermediate B2)

To a solution of BH$_3$.THF (1M, 5.7 mL, 5.7 mmol) in 40 mL anhydrous THF was dropwise added at room temperature (S)-2-methyl-CBS-oxazaborolidine (952 µL, 0.952 mmol, 1M in toluene). After stirring for 5 minutes, methyl 4-(4-fluorophenyl)-4-oxobutanoate (2.0 g, 9.5 mmol) was added as a solution in 25 mL THF. The reaction mixture was stirred for 30 min at room temperature and then quenched by the slow addition of saturated aqueous ammonium chloride (60 mL) The resulting mixture was extracted with ethyl acetate (3×50 mL) and the combined organic layers washed with brine (2×40 mL) and dried over Na$_2$SO$_4$. The solvent was evaporated under reduced pressure and the product isolated by silica gel Flash chromatography to afford 1.7 g of the title compound as a colorless oil.

LC/MS: $t_R$=5.7 min. MS (API-ES) m/z 235 (M+H$^+$+Na$^+$).

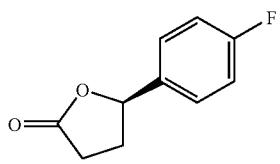

(R)-5-(4-fluorophenyl)dihydrofuran-2(3H)-one (Intermediate C2)

To a solution of (R)-methyl 4-(4-fluorophenyl)-4-hydroxybutanoate (1.7 g, 8.0 mmol) in DCM (40 mL) was added 8 drops TFA at room temperature. The reaction mixture was warmed to 40° C. and stirred for 16 h. Evaporation of the solvent gave a light yellow oil from which the product was isolated by Flash chromatography eluting with 0% to 30% ethyl acetate/hexane to give 1.6 g of the title compound as a colorless oil.

LC/MS: $t_R$=6.2 min. MS (API-ES) m/z 181 (M+H$^+$).

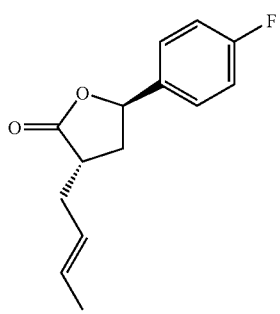

(3S,5R)-3-((E)-but-2-enyl)-5-(4-fluorophenyl)dihydrofuran-2(3H)-one (Intermediate D2)

To the solution of lithium bis(trimethylsilyl)amide (2.4 mL, 2.4 mmol, 1M in THF) in anhydrous 20 mL THF at −70° C. was slowly added over 15 minutes (R)-5-(4-fluorophenyl)dihydrofuran-2(3H)-one (360 mg, 2.0 mmol) as a solution in 1.0 mL THF. The reaction mixture was stirred for 20 min at −70° C. and then for 10 min at room temperature. The mixture was cooled to −70° C. and to it was slowly added a pre-cooled solution of 1-bromo-but-2-ene (324 mg, 2.4 mmol) in 400 μl HMPA an 100 μL of THF. The resulting mixture was stirred at −70° C. for 2 h and the temperature was slowly raised over a period of 2 h. The mixture was poured into 20 mL saturated NH$_4$Cl and extracted with ethyl acetate (3×30 mL). The combined organic layers were washed with brine (2×20 mL) and dried over Na$_2$SO$_4$. The solvent was removed under reduced pressure and the product isolated by Flash column chromatography eluting with 0% to 50% ethyl acetate/hexane to the title compound.

LC/MS: $t_R$=9.0 min. MS (API-ES) m/z 235 (M+H$^+$).

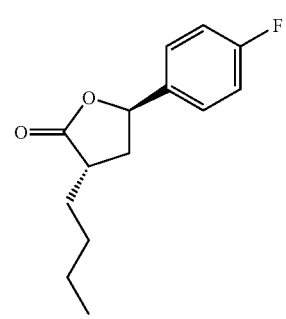

(3S,5R)-3-butyl-5-(4-fluorophenyl)dihydrofuran-2(3H)-one (Intermediate E2)

(3S,5R)-3-((E)-but-2-enyl)-5-(4-fluorophenyl)dihydrofuran-2(3H)-one (100.0 mg, 0.43 mmol) was dissolved into 8 mL benzene and to it added Wilkinson catalysis (39.0 mg, 0.4 mmol). The solution was saturated with H$_2$ (stream of H$_2$ bubbled through solution) and then stirred for 20 h at room temperature under an atmosphere of hydrogen balloon. The solvent was removed under reduced pressure and the product isolated by flash column chromatography eluting with 3% to 30% ethyl acetate/hexane to give 94 mg of the title compound as a colorless oil.

LC/MS: $t_R$=9.4 min. MS (API-ES) m/z 237 (M+H$^+$+Na$^+$).

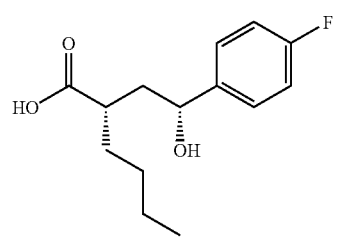

(S)-2-((R)-2-(4-fluorophenyl)-2-hydroxyethyl)hexanoic acid (Intermediate F2)

To the solution of (3S,5R)-3-butyl-5-(4-fluorophenyl)dihydrofuran-2(3H)-one (94.0 mg, 0.40 mmol) in 5 mL dioxane was added 5 mL aqueous 5% KOH at 25° C. After being stirred for 30 min at room temperature the reaction was quenched by the addition of 6 mL of 1M aqueous HCl. The mixture was extracted ethyl acetate (2×10 mL) and the combined organic layers were washed with brine (2×10 mL) before being concentrated under reduced pressure. The crude product was used directly in the next reaction without further purification.

LC/MS: $t_R$=7.2 min. MS (API-ES) m/z 277 (M+H$^+$+Na$^+$).

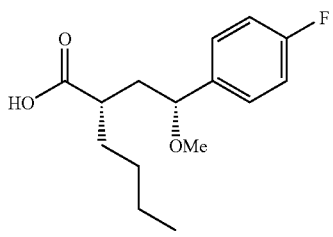

(S)-2-((R)-2-(4-fluorophenyl)-2-methoxyethyl)hexanoic acid (Intermediate G2)

To a suspension of NaH (129 mg, 60% oil dispersion) in 20 mL THF was slowly added at room temperature the crude (S)-2-((R)-2-(4-fluorophenyl)-2-hydroxyethyl)hexanoic acid isolated above as a solution in 10 mL THF. To this mixture was added dropwise methyl iodide (164 mL, 373.9 mg, 2.6 mmol) and the resulting stirred for 3 h at room temperature. The reaction was quenched by the slow addition of 15 mL 1M aqueous HCl and the mixture extracted with ethyl acetate (3×30 mL). The combined organic layers were washed with brine (2×20 mL) and dried over sodium sulfate. Evaporation of solvent afforded the product as an oil which was used directly in the next reaction without further purification.

LC/MS: $t_R$=808 min. MS (API-ES) m/z 291 (M+H$^+$+Na$^+$).

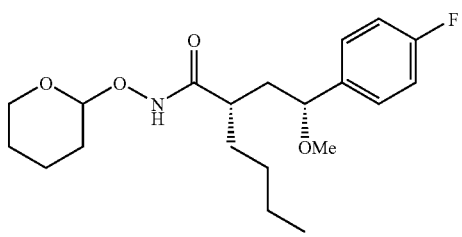

(2S)-2-((R)-2-(4-fluorophenyl)-2-methoxyethyl)-N-(tetrahydro-2H-pyran-2-yloxy)hexanamide (Intermediate H2)

To a mixture of O-(tetrahydro-2H-pyran-2-yl)hydroxylamine (73.8 mg, 0.63 mmol), HOBT (340 mg, 2.5 mmol), NaHCO$_3$ (423 mg, 2.9 mmol), and the (S)-2-((R)-2-(4-fluorophenyl)-2-methoxyethyl)hexanoic acid in 30 mL DCM was added EDC.HCl (407 mg, 2.1 mmol) as solid. The reaction mixture was stirred for 3 h at room temperature and then the solvent was removed under reduced pressure. The product was isolated by flash column chromatography, eluting with 10% to 60% EtOAc/Hexane gradient solvent to give 128 mg of the title compound.

LC/MS: $t_R$=8.9 min. MS (API-ES) m/z 368 (M+H$^+$).

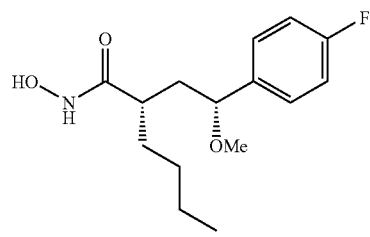

(S)-2-((R)-2-(4-fluorophenyl)-2-methoxyethyl)-N-hydroxyhexanamide (Compound 167336)

To a solution of (2S)-2-((R)-2-(4-fluorophenyl)-2-methoxyethyl)-N-(tetrahydro-2H-pyran-2-yloxy)hexanamide (43 mg, 0.12 mmol) in 3 mL DCM was slowly added 3 mL TFA followed by stirring for 30 min at room temperature. The solvent was evaporated and the product isolated by flash column chromatography eluting with 0% to 10% methanol/DCM to give 26 mg of the title compound as white solid.

1H NMR (CD$_3$OD): δ 7.28 (dd, 2H, J=5.4 and 8.6), 7.06 (t, 2H, J=8.5), 4.02 (dd, 1H, J=3.8 and 9.7), 3.17 (s, 3H), 2.44 (m, 1H), 1.75 (m, 2H), 1.32 (m, 6H), 0.90 (t, 3H, J=639).

LC/MS: $t_R$=6.6 min. MS (API-ES) m/z 306 (M+H$^+$+Na$^+$).

Specific Scheme 3

Intermediate A3

Intermediate B3

Reagents and conditions: a) Mg, I$_2$, THF, -30-60° C., 3h; b) Jones oxidation, acetone, THF, 25° C., 20 min;

3-(1,3-Dioxolan-2-yl)-1-(4-fluoro-3-methylphenyl)propan-1-ol (Intermediate A3)

To a suspension of Mg turnings (1.1 g, 0.05 g-at.) and catalytic amount of iodine in 200 mL THF was added dropwise 2-(2-bromoethyl)-[1,3]dioxolane (4.3 g, 0.02 mol) with heating over a period of 30 min. The resulting mixture was stirred for 30 min at 63° C. and then cooled to −30° C. and 4-fluoro-3-methyl-benzaldehyde (3.0 g, 0.02 mol) added slowly as a solution in 50 mL of THF. The temperature was maintained at −30° C. for 1 h and then slowly raised to room temperature over a period of 3 h. The excess Grignard was destroyed by the careful addition of 200 mL saturated aqueous NH₄Cl. The mixture was extracted with ethyl acetate (3×100 mL) and the combined organic layers washed with brine (2×50 mL) and dried over Na₂SO₄. After evaporation of the solvent, the product was isolated by flash column chromatography eluting with 0% to 50% ethyl acetate/hexanes to give 1.6 g of the title compounds as a light yellow oil.

LC/MS: $t_R$=7.8 min. MS (API-ES) m/z 241 (M+H⁺).

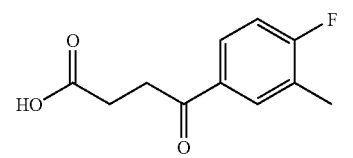

4-(4-Fluoro-3-methylphenyl)-4-oxobutanoic acid (Intermediate B3)

To a solution of 3-(1,3-dioxolan-2-yl)-1-(4-fluoro-3-methylphenyl)propan-1-ol (1.6 g, 6.7 mmol) in 15 ml acetone was added Jones reagent (1.5 mL) dropwise at room temperature. The mixture was stirred for 30 min. and then 50 mL of water was added before extracting with DCM (3×40 mL). The combined DCM layers were washed with water (2×20 mL) and dried over Na₂SO₄. The solvent was evaporated under reduce pressure and the crude product used for the next step without further purification.

LC/MS: $t_R$=6.0 min. MS (API-ES) m/z 211 (M+H⁺).

Specific Scheme 4

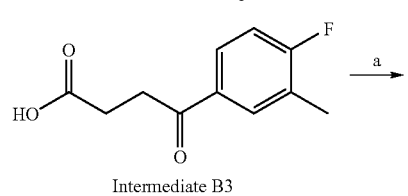
Intermediate B3

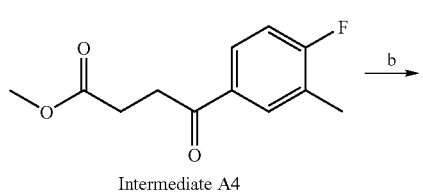
Intermediate A4

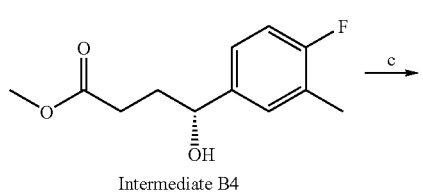
Intermediate B4

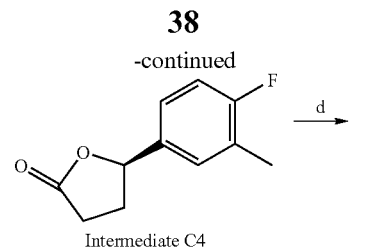
Intermediate C4

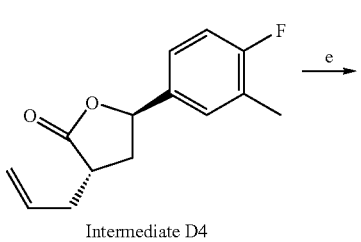
Intermediate D4

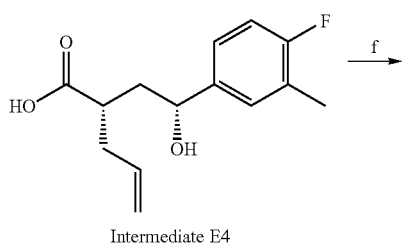
Intermediate E4

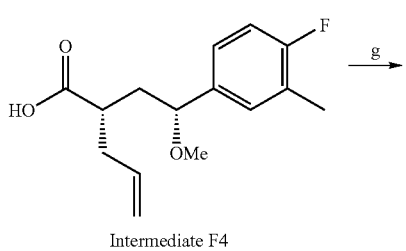
Intermediate F4

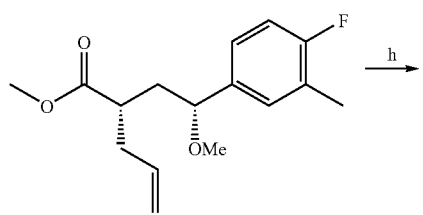
Intermediate G4

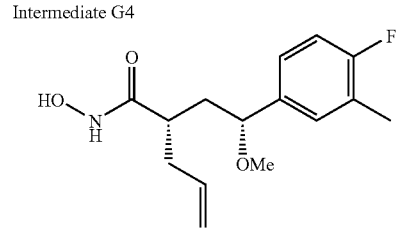
Compound 167673

Reagents and conditions: a) conc. H₂SO₄, MeOH, 25° C., 12 h; b) (S)-2-methyl-CBS-oxazaborolane, BH₃·THF, THF, 25° C., 30 min; c) TFA, DCM, 40° C., 12 h; d) LiHMDS, HMPA, allyl iodine, −70-25° C., 4 h; e) KOH, H₂O, dioxane, 25° C., 30 min; f) MeI, NaH, THF, 25° C., 3 h; g) conc. H₂SO₄, MeOH, 25° C., 12 h; h) NH²-OH, KCN, H₂O, MeOH, THF, 25° C., 24 h.

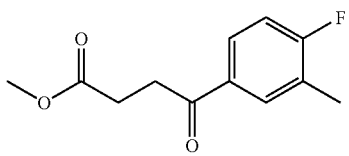

Methyl 4-(4-fluoro-3-methylphenyl)-4-oxobutanoate (Intermediate A4)

To a solution of 4-(4-fluoro-3-methylphenyl)-4-oxobutanoic acid in 30 mL methanol was added concentrated H$_2$SO$_4$ (300 mL) at room temperature and the resulting mixture was stirred for 16 h. The mixture was concentrated under reduced pressure and the residue treated with 30 mL water and the resulting mixture extracted with ethyl acetate (3×40 mL). The combined organic layers were washed with brine (2×20 mL) and dried over Na$_2$SO$_4$. The product was isolated by flash column chromatography eluting with 0% to 10% ethyl acetate/hexane gradient solvent to give 568 mg of the title compound as a colorless oil.

LC/MS: t$_R$=7.8 min. MS (API-ES) m/z 225 (M+H$^+$).

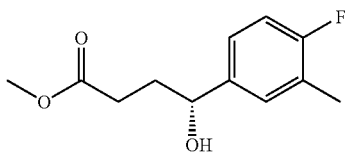

(R)-Methyl 4-(4-fluoro-3-methyl-phenyl)-4-hydroxy-butanoate (Intermediate B4)

To a solution of BH$_3$.THF (0.9 mmol) in 20 mL anhydrous THF, was added dropwise at room temperature 158 mL (S)-2-methyl-CBS-oxazaborolidine in toluene and the mixture stirred for 5 min. To this mixture was slowly added methyl 4-(4-fluoro-3-methyl-phenyl)-4-oxo-butyric acid methyl ester (354 mg) in 5 mL THF and stirring continued for 30 min at 25° C. Saturated ammonium chloride (30 mL) was slowly added and the resulting mixture extracted with ethyl acetate (3×40 mL). The combined organic layers were washed with brine (2×20 mL) and dried over Na$_2$SO$_4$. The solvent was evaporated under reduced pressure and the product isolated by silica gel chromatography to afford 289 mg of the title compound as a colorless oil.

LC/MS: t$_R$=6.6 min. MS (API-ES) m/z 249 (M+H$^+$+Na$^+$).

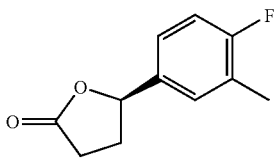

(R)-5-(4-Fluoro-3-methyl-phenyl)-dihydro-furan-2-one (Intermediate C4)

To a solution of (R)-methyl 4-(4-fluoro-3-methyl-phenyl)-4-hydroxy-butanoate (289 mg) in 20 mL DCM was added 4 drops TFA at room temperature and the resulting solution warmed to 40° C. After stirring for 16 h the reaction was cooled to room temperature and concentrated under reduced pressure. The product was isolated by flash column chromatograph eluting with 0% to 30% ethyl acetate/hexane gradient solvent to give 279 mg of (R)-5-(4-fluoro-3-methylphenyl)-dihydro-furan-2-one as a colorless oil.

LC/MS: t$_R$=7.0 min. MS (API-ES) m/z 195 (M+H$^+$+Na$^+$).

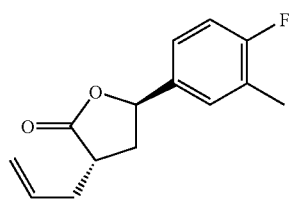

(3S,5R)-3-Allyl-5-(4-fluoro-3-methylphenyl)dihydrofuran-2(3H)-one (Intermediate D4)

To a solution of lithium bis(trimethylsilyl)amide (1.2 mmol) in anhydrous THF (20 mL) was added (R)-5-(4-fluoro-3-methyl-phenyl)-dihydro-furan-2-one (194 mg) in 1 mL THF at −70° C. over a period of 15 minutes. After completing the addition, the mixture was stirred for an additional 20 min at −70° C. and then for 10 min at room temperature. The mixture was cooled down again to −70° C. and a pre-cooled solution of 200 mg 1-bromo-but-2-ene and 400 µL HMPA in 1 mL THF slowly added. The mixture was further stirred at −70° C. for 2 h and the temperature was slowly raised to room temperature over a period of 2 h. The reaction was quenched by pouring into saturated NH$_4$Cl (20 mL) and followed extraction with ethyl acetate (3×30 mL). The combined organic layers were washed with 20 mL brine twice and dried over Na$_2$SO$_4$. The solvent was removed under reduced pressure and the product isolated by flash column chromatographed eluting with 0% to 50% ethyl acetate/hexane gradient solvent to give the anti/syn products (94:6 ratios).

LC/MS: t$_R$=8.9 min. MS (API-ES) m/z 235 (M+H$^+$).

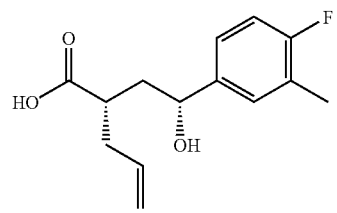

(S)-2-((R)-2-(4-Fluoro-3-methylphenyl)-2-hydroxyethyl)pent-4-enoic acid (Intermediate E4)

To a solution of 150 mg (3S,5R)-3-allyl-5-(4-fluoro-3-methylphenyl)dihydrofuran-2(3H)-one in 5 mL dioxane was added 5 mL aq. 5% KOH at 25° C. The mixture was stirred for 30 min at 25° C. then hydrolyzed with 10 mL of 1M HCl. The resulting mixture was extracted twice with ethyl acetate (10 mL). The combined organic layers were then extracted with 5 mL 5% K$_2$CO$_3$ three times and the combined aqueous layers acidified with 1M HCl to pH3. The resulting mixture was extracted with ethyl acetate (3×30 mL), the combined organic layers washed with brine (2×20 mL) before being concentrated under reduced pressure. The crude product residue was used for the next step without further purification.

LC/MS: $t_R$=6.7 min. MS (API-ES) m/z 235 (M+H$^+$—H$_2$O).

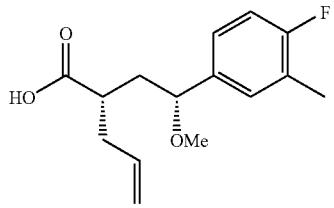

(S)-2-((R)-2-(4-Fluoro-3-methylphenyl)-2-methoxy-ethyl)pent-4-enoic acid (Intermediate F4)

To a suspension of 217 mg NaH in 20 mL THF was added (S)-2-((R)-2-(4-fluoro-3-methylphenyl)-2-hydroxyethyl) pent-4-enoic acid in 5 mL THF slowly at room temperature. To this mixture was added methyl iodide (289 µL) dropwise followed by stirring for 3 h at 25° C. The reaction was quenched by the addition of 10 mL 1M HCl and then extracted with ethylacetate (3×30 mL). The combined organic layers were washed with brine (2×20 mL) and dried over sodium sulfate. Evaporation of solvent afforded an oil which was used without further purification in the next reaction.

LC/MS: $t_R$=8.3 min. MS (API-ES) m/z 235 (M+H$^+$-OMe).

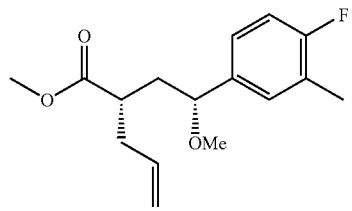

(S)-Methyl 2-((R)-2-(4-fluoro-3-methylphenyl)-2-methoxyethyl)pent-4-enoate (Intermediate G4)

To a solution of (S)-2((R)-2-(4-fluoro-3-methylphenyl)-2-methoxyethyl)pent-4-enoic acid in 5 mL methanol was added concentrated H$_2$SO$_4$ (50 mL) at room temperature and the resulting solution stirred for 16 h. The reaction mixture was concentrated under reduced pressure, the residue treated with water, and the mixture was extracted with ethyl acetate (3×20 mL). The combined organic layers were washed with brine (2×10 mL) and dried over Na$_2$SO$_4$. The product was isolated by flash column chromatography eluting with 0% to 10% ethyl acetate/hexane gradient solvent to give 122 mg of the title compound as a colorless oil.

LC/MS: $t_R$=10.3 min. MS (API-ES) m/z 250 (M+H$^+$—OMe).

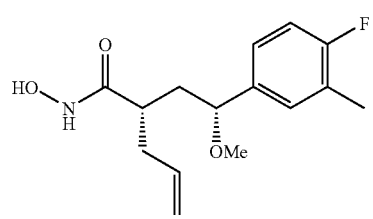

(S)-2-((R)-2-(4-Fluoro-3-methylphenyl)-2-methoxy-ethyl)-N-hydroxypent-4-enamide (Compound 167673)

(S)-Methyl 2-((R)-2-(4-fluoro-3-methylphenyl)-2-methoxyethyl)pent-4-enoate (50 mg) was dissolved into 1 mL of a mixture of THF, methanol, and 50% NH$_2$OH in H$_2$O (2:2:1) and to this solution was added 2 mg KCN. The reaction was stirred for 3 days at room temperature and then quenched by the addition of 1M HCl (10 mL). The mixture was extracted with ethyl acetate (3×20 mL). The combined organic layers were washed with brine (2×10 mL) before being concentrated under reduced pressure. The product was isolated by flash column chromatography eluting with 0% to 10% methanol/DCM to obtain the title compound (34 mg) as white solid.

1H NMR (CD$_3$OD): δ 7.12 (dd, 2H, J=7.1 and 16.8), 6.99 (t, 1H, J=8.91), 5.08 (m, 1H), 4.99 (m, 2H), 4.05 (dd, 2H, J=4.8 and 8.7, 1H), 3.59 (t, 2H, J=4.1), 3.12 (s, 3H), 2.32-2.13 (m, 5H).

LC/MS: $t_R$=6.2 min. MS (API-ES) m/z 304 (M+H++Na$^+$).

Specific Scheme 5

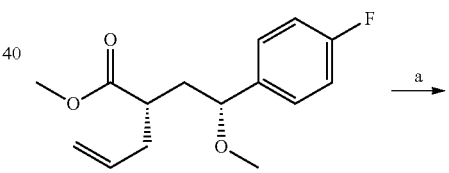

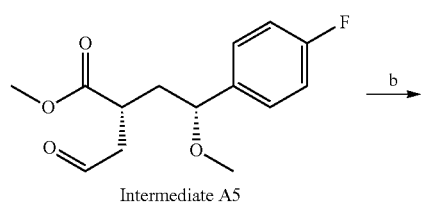

Intermediate A5

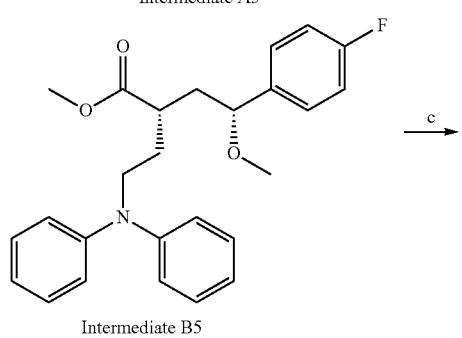

Intermediate B5

-continued

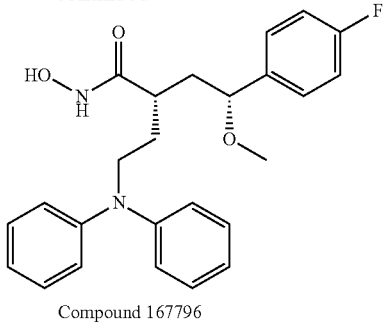

Compound 167796

Reagents and conditions: a) O₃, Ph₃P, DCM, -70° C. to RT, 4 h;
b) diphenylamine, NaBH(OAc)₃, AcOH, DCE, RT, 8 h; c) NH₂—OH, KCN, H₂O, MeOH, THF, 25° C., 3 days.

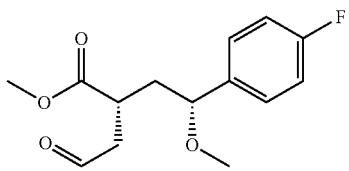

(4R)-(4-Fluoro-phenyl)-4-methoxy-2(S)-(2-oxo-ethyl)-butyric acid methyl ester (Intermediate A5)

A solution of (2S)-[2-(4-Fluoro-phenyl)-2(R)-methoxy-ethyl]-pent-4-enoic acid methyl ester (200 mg, 0.75 mmol) in 20 mL DCM was cooled to −70° C. and O₃ bubbled through it until the solution showed a faint blue color. The solution was purged of any remaining O₃ tubing by sparging with N₂ for about 30 minutes. Triphenylphosphine (787 mg, 3.0 mmol) was added at −70° C. and the temperature was slowly raised to room temperature. The resulting mixture was stirred for 3 h. After concentrating under reduced pressure, the product was isolated by silica gel chromatography to afford the title compound 198 mg, as an colorless oil.

1H NMR (CDCl₃): δ 9.76 (s, 1H), 7.26 (m, 2H), 7.04 (t, 2H, J=8.4), 4.15 (dd, 1H, J=3.6 and 9.5), 3.71 (s, 3H), 3.21 (m, 1H), 3.16 (s, 3H), 2.90 (dd, 1H, J=8.0 and 17.9), 2.68 (dd, 1H, J=5.2 and 18.0), 1.93 (m, 2H).

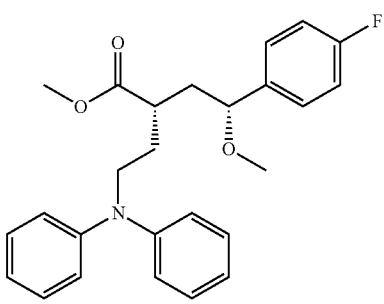

(2S)-(2-Diphenylamino-ethyl)-(4R)-(4-fluoro-phenyl)-4-methoxy-butyric acid methyl ester (Intermediate B5)

To a solution of 4(R)-(4-Fluoro-phenyl)-4-methoxy-2(S)-(2-oxo-ethyl)-butyric acid methyl ester (50 mg, 0.18 mmol) in 5 mL DCE was added diphenylamine (30.5 mg, 0.18 mmol) followed by NaBH(OAc)₃ (55.3 mg, 0.26 mmol) and AcOH (10.8 mg, 0.18 mmol) at room temperature. The mixture was stirred for 8 h at the room temperature. The reaction was quenched by pouring into 20 mL 5% aqueous NaOH and diluted with ethyl acetate. The mixture was extracted with more ethyl acetate (3×15 mL) and the combined organic layers washed with brine (2×10 mL) and dried over Na₂SO₄. The mixture was concentrated under reduced pressure and the product isolated by flash column chromatography eluting with 6% to 60% ethyl acetate/hexane to provide 58 mg of the title compound as an colorless oil.

LC/MS: $t_R$=12.0 min. MS (API-ES) m/z 422 (M+H⁺).

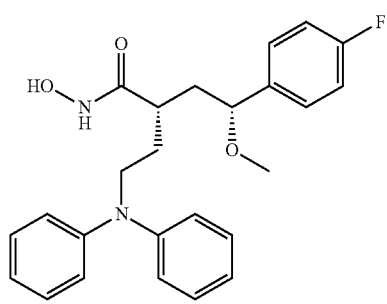

(2S)-(2-Diphenylamino-ethyl)-(4R)-(4-fluoro-phenyl)-N-hydroxy-4-methoxy-butyramide (Compound 167796)

To a solution of (2S)-(2-Diphenylamino-ethyl)-(4R)-(4-fluoro-phenyl)-4-methoxy-butyric acid methyl ester (50.0 mg, 0.11 mmol) dissolved in 2 mL of THF, methanol, and 50 wt % NH₂OH in H₂O (2:2:1) was added KCN (4.0 mg, 0.06) and the resulting mixture stirred for 3 days at room temperature. The reaction was quenched by the addition of water (10 mL) and the resulting mixture extracted with ethyl acetate (3×10 mL). The combined organic layers were washed with brine (2×5 mL). The product was isolated by flash column chromatography eluting with 0% to 10% methanol/DCM to give the title compound (34 mg) as white solid 1H NMR (CD₃OD): δ 7.23 (m, 6H), 7.04 (t, 2H, J=8.8), 6.93 (m, 6H), 4.02 (dd, 1H, J=3.6 and 9.87), 3.66 (t, 2H, J=8.1), 3.16 (s, 3H), 2.51 (m, 1H), 2.01-1.65 (m, 4H).

LC/MS: $t_R$=9.5 min. MS (API-ES) m/z 423 (M+H⁺).

Specific Scheme 6

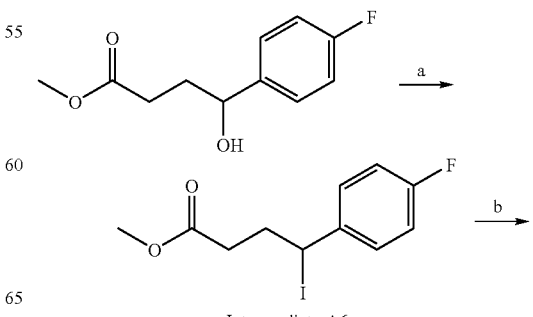

Intermediate A6

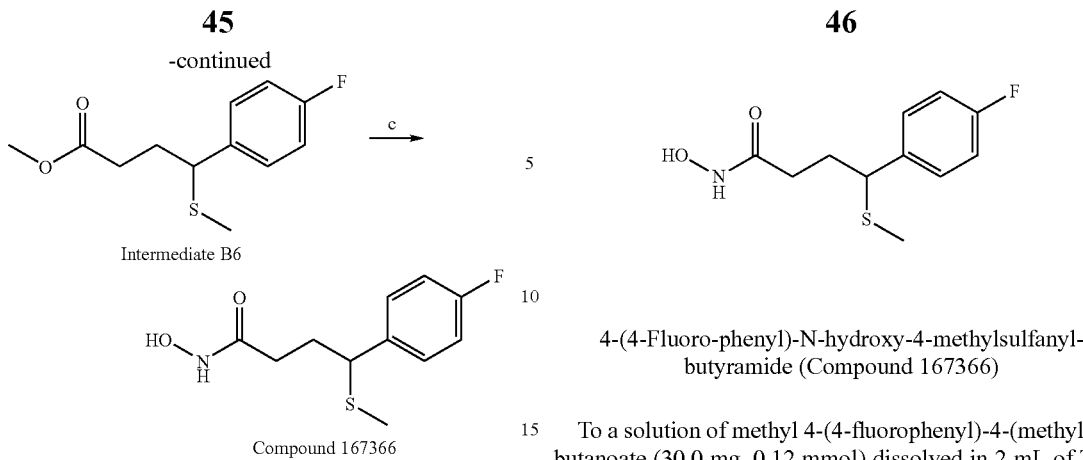

Compound 167366

Reagents and conditions: a) Ph₃P, Im, I₂, DCM, 0° C. to RT, 3 h; b) NaSMe, EtOH, 8 h. c) NH₂—OH, KCN, H₂O, MeOH, THF, 25° C., 3 days.

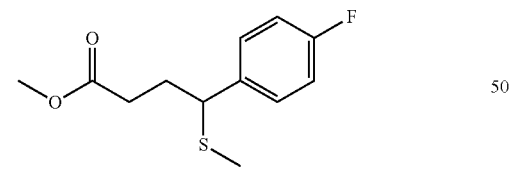

Methyl 4-(4-fluorophenyl)-4-iodobutanoate (Intermediate A6)

To a solution of triphenylphosphine (419 mg, 1.6 mmol) in anhydrous 20 mL DCM was added imidazole (224 mg, 3.3 mmol) and iodine (406 mg, 1.6 mmol) at 0° C. The reaction mixture was stirred for 30 min at 0° C. and then methyl 4-(4-fluorophenyl)-4-hydroxybutanoate (212 mg, 1 mmol) in 10 mL DCM was added to the mixture. The resulting mixture was stirred at 0° C. for 2 h and the temperature was slowly raised to room temp over a period of 3 h. Evaporation of solvent left the crude product as an oil from which the product was isolated by Flash column chromatography eluting with 0% to 10% ethyl acetate/hexane to give the title compound, 161 mg, as a light yellow oil.

LC/MS: $t_R$=8.2 min. MS (API-ES) m/z 196 (M+H⁺—I).

Methyl 4-(4-fluorophenyl)-4-(methylthio)butanoate (Intermediate B6)

To a solution of methyl 4-(4-fluorophenyl)-4-iodobutanoate (100 mg, 0.31 mmol) in 4 mL ethanol was added NaSMe (200 mg, 2.8 mmol) at 25° C. After being stirred for 8 h at room temperature, the reaction mixture was diluted with water and extracted ethyl acetate (3×10 mL). The combined organic layers were washed with brine (2×10 mL) before being dried over Na₂SO₄. The mixture was concentrated under reduced pressure. The crude product was used directly in the next reaction without further purification.

4-(4-Fluoro-phenyl)-N-hydroxy-4-methylsulfanyl-butyramide (Compound 167366)

To a solution of methyl 4-(4-fluorophenyl)-4-(methylthio)butanoate (30.0 mg, 0.12 mmol) dissolved in 2 mL of THF, methanol, and 50 wt % NH₂OH in H₂O (2:2:1) was added KCN (4.0 mg, 0.06) and the resulting mixture stirred for 3 days at room temperature. The reaction was quenched by the addition of aqueous 1M HCl (10 mL) and the resulting mixture extracted with ethyl acetate (3×10 mL). The combined organic layers were washed with brine (2×5 mL). The product was isolated by flash column chromatography eluting with 0% to 10% methanol/DCM to give the title compound (27 mg) as a colorless oil.

1H NMR (CD₃OD): δ7.87 (s, 1H), 7.31 (dd, 2H, J=5.4 and 8.5), 7.03 (t, 2H, J=8.7), 3.70 (t, 1H, J=7.8), 2.22-1.94 (m, 4H), 1.85 (s, 3H).

LC/MS: $t_R$=5.2 min. MS (API-ES) m/z 266 (M+H⁺+Na⁺).

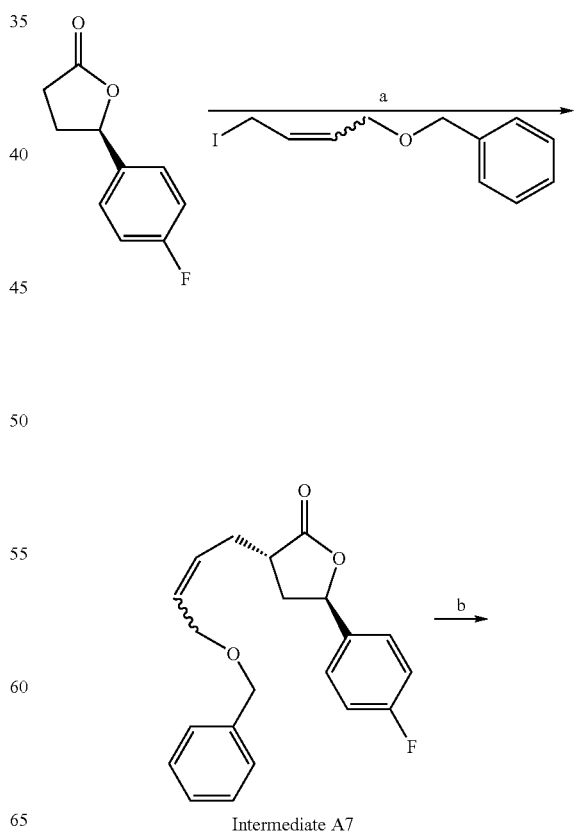

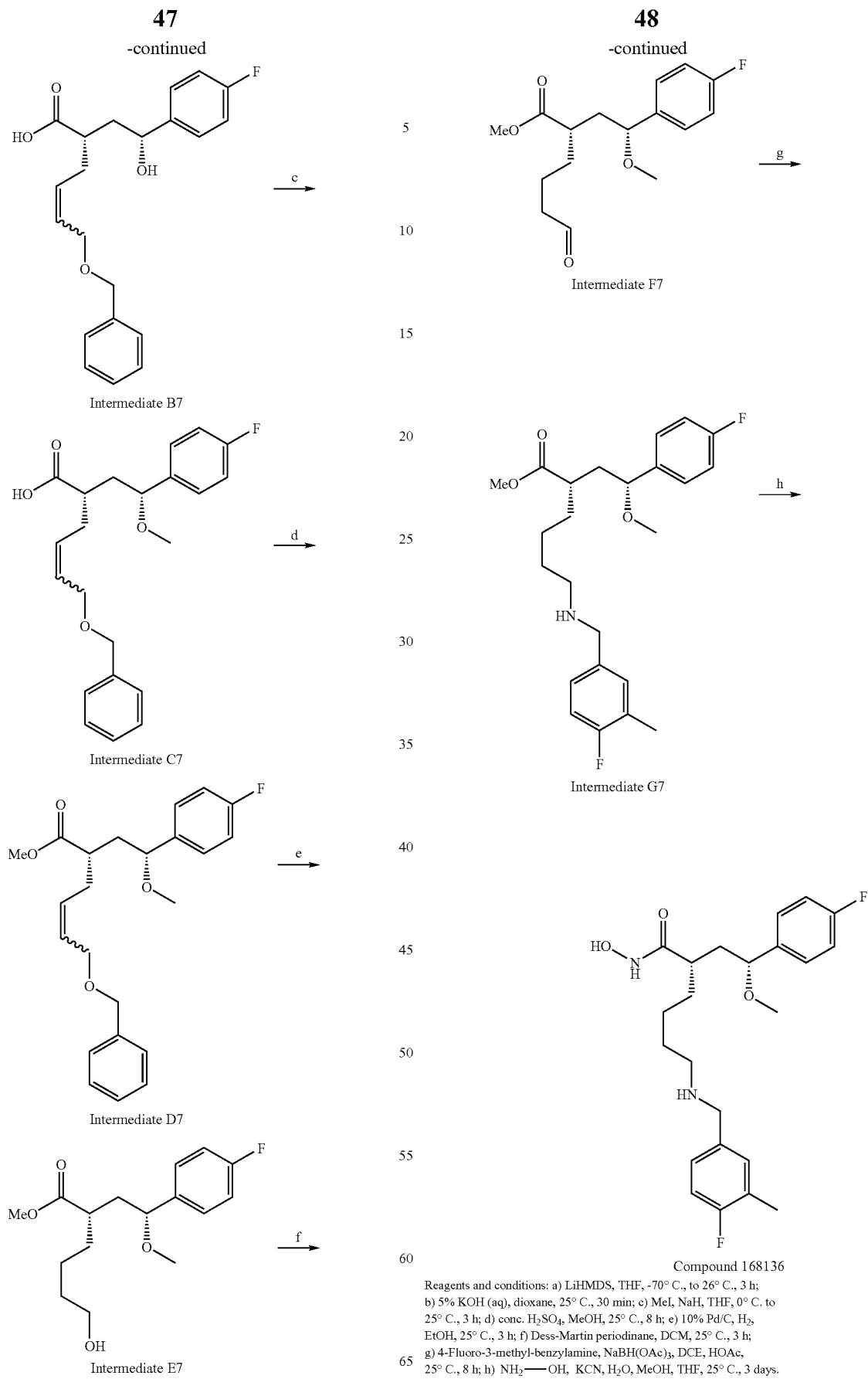
Reagents and conditions: a) LiHMDS, THF, -70° C., to 26° C., 3 h; b) 5% KOH (aq), dioxane, 25° C., 30 min; c) MeI, NaH, THF, 0° C. to 25° C., 3 h; d) conc. H₂SO₄, MeOH, 25° C., 8 h; e) 10% Pd/C, H₂, EtOH, 25° C., 3 h; f) Dess-Martin periodinane, DCM, 25° C., 3 h; g) 4-Fluoro-3-methyl-benzylamine, NaBH(OAc)₃, DCE, HOAc, 25° C., 8 h; h) NH₂—OH, KCN, H₂O, MeOH, THF, 25° C., 3 days.

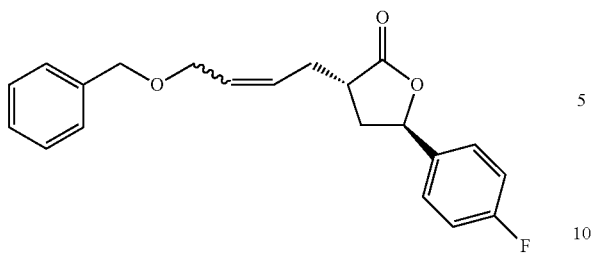

(3S,5R)-3-(4-(benzyloxy)but-2-enyl)-5-(4-fluorophenyl)dihydrofuran-2(3H)-one (Intermediate A7)

To a solution of lithium bis(trimethylsilyl)amide (4.6 mL, 4.6 mmol, 1M in THF) in anhydrous 40 mL THF at −70° C. was slowly added over 15 minutes ((R)-5-(4-fluorophenyl)dihydrofuran-2(3H)-one (685 mg, 3.8 mmol) as a solution in 4 mL THF. After the reaction mixture was stirred for 30 min at −70° C. a pre-cooled solution of (4-Iodo-but-2-enyloxymethyl)-benzene (1.3 g, 4.6 mmol) in 4 mL of THF was slowly added. The resulting mixture was stirred at −70° C. for 1 h and the temperature was slowly raised to room temperature over a period of 2 h. The mixture was poured into 20 mL saturated NH$_4$Cl and extracted with ethyl acetate (3×50 mL). The combined organic layers were washed with brine (2×30 mL) and dried over Na$_2$SO$_4$. The solvent was removed under reduced pressure and the product isolated by Flash column chromatography eluting with 0% to 50% ethyl acetate/hexane to give 827 mg of the title compound as a light yellow oil.

MS (EI) m/z 139 (M−201) base peak.

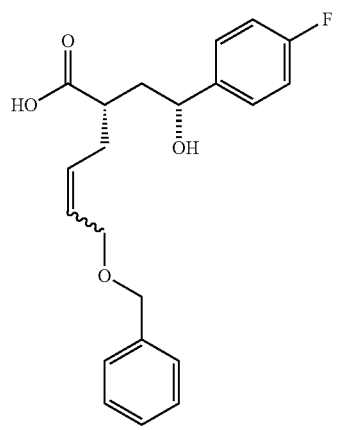

(S)-6-(benzyloxy)-2-((R)-2-(4-fluorophenyl)-2-hydroxyethyl)hex-4-enoic acid (Intermediate B7)

To a solution of (3S,5R)-3-(4-(benzyloxy)but-2-enyl)-5-(4-fluorophenyl)dihydrofuran-2(3H)-one (643 mg, 1.9 mmol) in 7 mL dioxane was added 7 mL aqueous 5% KOH at 25° C. After being stirred for 30 min at room temperature the reaction was quenched by the addition of 10 mL of 1M aqueous HCl. The mixture was extracted ethyl acetate (2×50 mL) and the combined organic layers were washed with brine (2×30 mL). The solution was dried over Na$_2$SO$_4$ before being concentrated under reduced pressure. The crude product was used directly in the next reaction without further purification.

MS (EI) m/z 139 (M−219) base peak.

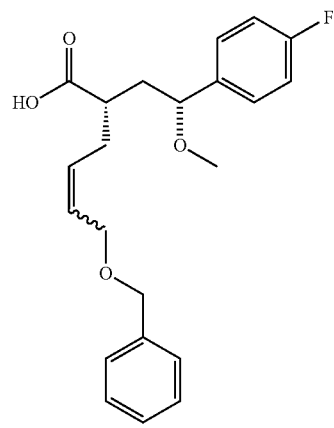

(S)-6-(benzyloxy)-2-((R)-2-(4-fluorophenyl)-2-methoxyethyl)hex-4-enoic acid (Intermediate C7)

To a suspension of NaH (605 mg, 60% oil dispersion) in 30 mL THF was slowly added at room temperature the crude (S)-6-(benzyloxy)-2-((R)-2-(4-fluorophenyl)-2-hydroxyethyl)hex-4-enoic acid isolated above as a solution in 5 mL THF. To this mixture was added dropwise methyl iodide (732 µL, 1.7 g, 11.3 mmol) and the resulting stirred for 3 h at room temperature. The reaction was quenched by the slow addition of 20 mL 1M aqueous HCl and the mixture extracted with ethyl acetate (3×50 mL). The combined organic layers were washed with brine (2×30 mL) and dried over sodium sulfate. Evaporation of solvent afforded the product as an oil which was used directly in the next reaction without further purification.

MS (EI) m/z 91 (M−281) base peak.

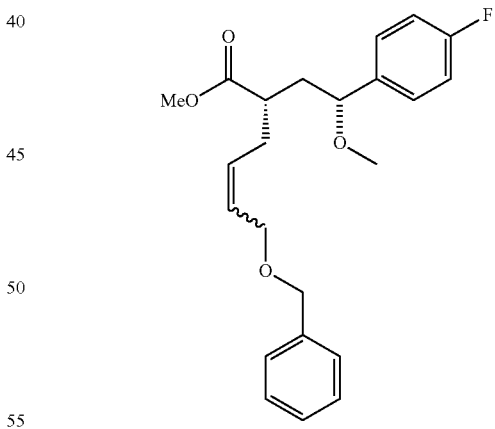

(S)-methyl 6-(benzyloxy)-2-((R)-2-(4-fluorophenyl)-2-methoxyethyl)hex-4-enoate (Intermediate D7)

To a solution of ((S)-6-(benzyloxy)-2-((R)-2-(4-fluorophenyl)-2-methoxyethyl)hex-4-enoic acid in 10 mL methanol was added concentrated H$_2$SO$_4$ (150 µL) at room temperature and the resulting solution stirred for 8 h. The reaction mixture was concentrated under reduced pressure, the residue treated with water, and the mixture was extracted with ethyl acetate (3×40 mL). The combined organic layers were washed with brine (2×30 mL) and dried over Na$_2$SO$_4$. The product was isolated by flash column chromatography eluting with 0% to 20% ethyl acetate/hexane gradient solvent to give 494 mg of the title compound as a colorless oil.

MS (EI) m/z 91 (M–295) base peak.

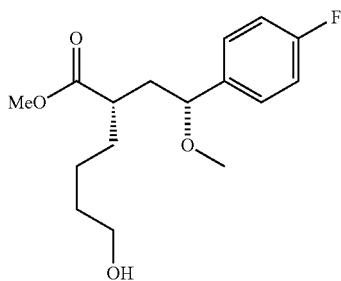

(S)-methyl 2-((R)-2-(4-fluorophenyl)-2-methoxyethyl)-6-hydroxyhexanoate (Intermediate E7)

(S)-methyl 6-(benzyloxy)-2-((R)-2-(4-fluorophenyl)-2-methoxyethyl)hex-4-enoate (494 mg, 1.2 mmol) was dissolved into 5 mL EtOH and to it added 10% Pd/C (450 mg). The solution was saturated with H$_2$ (stream of H$_2$ bubbled through solution) and then stirred for 3 h at room temperature under one atmosphere of hydrogen (balloon). The mixture was filtered through a bed of Celite and rinsed with ethyl acetate. The solvent was removed under reduced pressure and the crude product used directly in the next step without further purification.

MS (EI) m/z 91 (M–207) base peak.

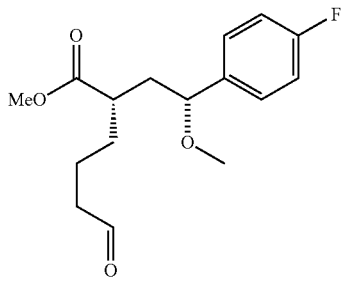

(S)-methyl 2-((R)-2-(4-fluorophenyl)-2-methoxyethyl)-6-oxohexanoate (Intermediate F7)

To the crude solution of ((S)-methyl 2-((R)-2-(4-fluorophenyl)-2-methoxyethyl)-6-hydroxyhexanoate isolated above (100 mg, 0.33 mmol) in 10 mL DCM was added Dess-Martin periodinane (284 mg, 0.67 mmol) at 25° C. After being stirred for 3 h at 25° C., the mixture was filtered through a bed of Celite and rinsed with more DCM. The solvent was removed under reduced pressure and the product isolated by Flash column chromatography eluting with 0% to 50% ethyl acetate/hexane to give 78 mg of the title compound as a light yellow oil.

MS (EI) m/z 91 (M–205) base peak.

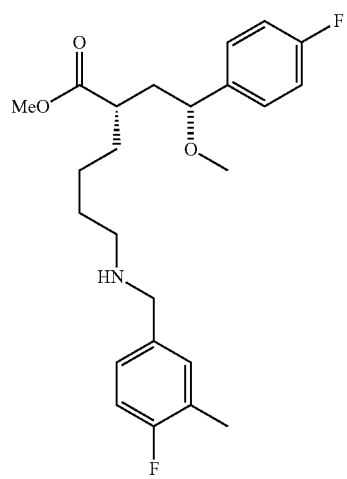

(S)-methyl 6-(4-fluoro-3-methylbenzylamino)-2-((R)-2-(4-fluorophenyl)-2-methoxyethyl)hexanoate (Intermediate G7)

To a solution of (S)-methyl 2-((R)-2-(4-fluorophenyl)-2-methoxyethyl)-6-oxohexanoate (40 mg, 0.13 mmol) in 2 mL DCE was added 4-Fluoro-3-methyl-benzylamine (21 mg, 0.15 mmol) followed by NaBH(OAc)$_3$ (39.9 mg, 1.4 mmol) and AcOH (9.3 mg, 9 µL, 0.15 mmol) at room temperature. The mixture was stirred for 8 h at the room temperature. The reaction was quenched by pouring into 10 mL 5% aqueous NaOH and diluted with ethyl acetate. The mixture was extracted with more ethyl acetate (3×20 mL) and the combined organic layers washed with brine (2×10 mL) and dried over Na$_2$SO$_4$. The solvent was removed under reduced pressure and the crude product used directly in the next step without further purification.

MS (EI) m/z 123 (M–296) base peak.

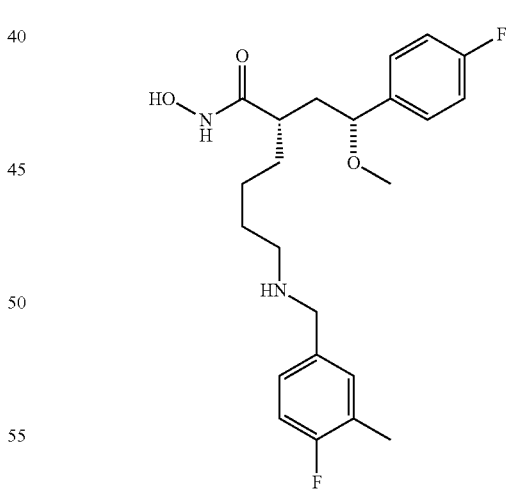

(S)-6-(4-fluoro-3-methylbenzylamino)-2-((R)-2-(4-fluorophenyl)-2-methoxyethyl)-N-hydroxyhexanamide (Compound 168136)

To a crude solution of (S)-methyl 6-(4-fluoro-3-methylbenzylamino)-2-((R)-2-(4-fluorophenyl)-2-methoxyethyl) hexanoate isolated above and dissolved in 2 mL of THF, methanol, and 50 wt % NH$_2$OH in H$_2$O (2:2:1) was added KCN (4.0 mg, 0.06 mmol). The resulting mixture stirred for 3 days at room temperature. Evaporation of solvent left the crude from which the product was isolated RP-HPLC eluting with 80% to 2% CH$_3$CN/H$_2$O with 0.025% TFA to give the title compound, 14 mg, as light brown oil.

1H NMR (CD$_3$OD): δ): 7.30 (m, 4H), 7.10 (m, 3H), 4.12 (s, 2H), 4.03 (dd, 1H, J=3.7 and 9.7), 3.17 (s, 3H), 3.00 (t, 1H, J=8.0), 2.47 (m, 1H), 1.80-1.25 (m, 8H).

LC/MS: t$_R$=4.7 min. MS (API-ES) m/z 421 (M+H$^+$).

Specific Scheme 8

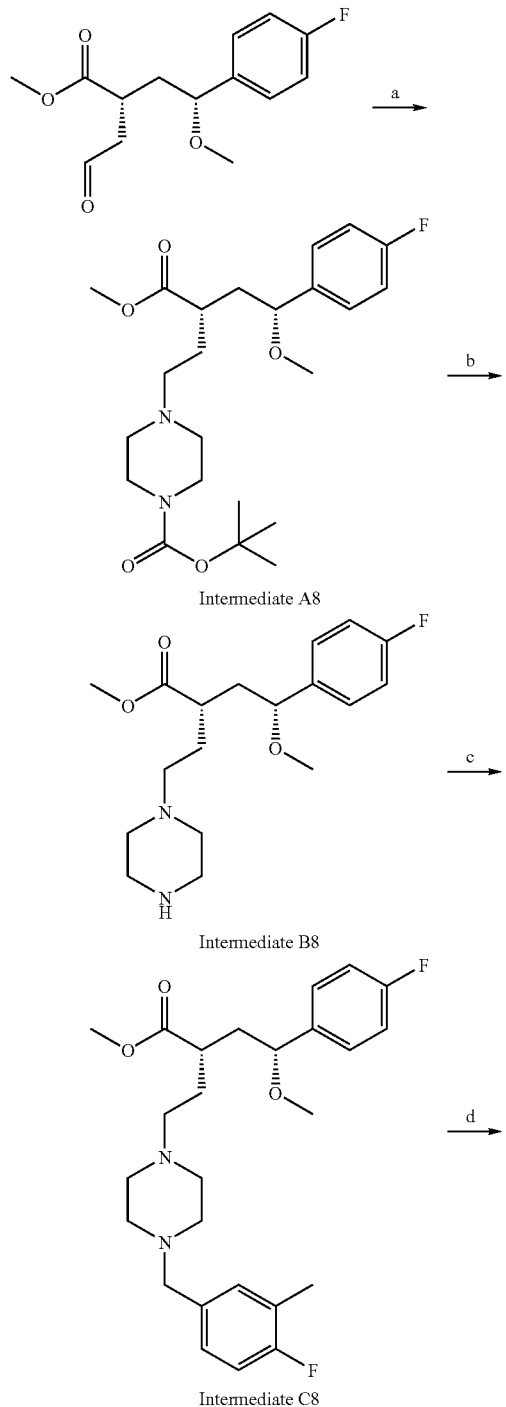

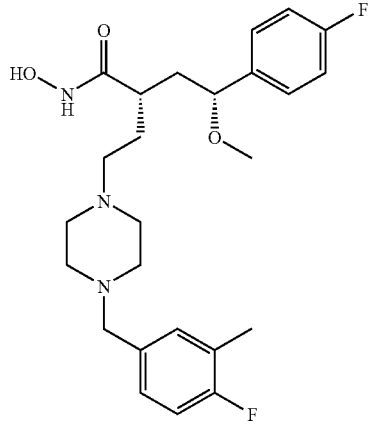

Compound 167960

Reagents and conditions: a) piperazine-1-carboxylic acid tert-butyl ester, NaBH(OAc)$_3$, DCE, 25° C., 8 h; b) TFA, DCM, 25° C., 1 h; c) 4-Fluoro-3-methyl-benzaldehyde, NaBH(OAc)$_3$, DCE, HOAc, 25° C., 8 h; d) NH$_2$—OH, KCN, H$_2$O, MeOH, THF, 25° C., 3 days.

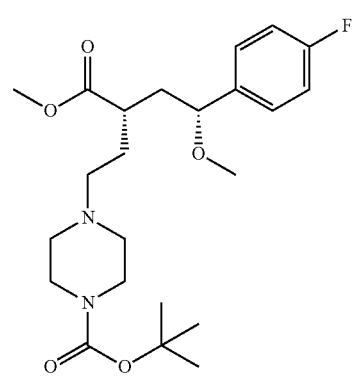

tert-Butyl 4-((3S,5R)-5-(4-fluorophenyl)-5-methoxy-3-(methoxycarbonyl)pentyl)piperazine-1-carboxylate (Intermediate A8)

To a solution of 4(R)-(4-Fluoro-phenyl)-4-methoxy-2(S)-(2-oxo-ethyl)-butyric acid methyl ester (200 mg, 0.74 mmol) and piperazine-1-carboxylic acid tert-butyl ester (166 mg, 0.89 mmol) was added NaBH(OAc)$_3$ (218 mg, 1.03 mmol) and AcOH (53.4 mg, 51 µL, 0.89 mmol) at room temperature. The mixture was stirred for 8 h at the room temperature. The reaction was quenched by pouring into 20 mL 5% aqueous NaOH and diluted with ethylacetate. The mixture was extracted with ethyl acetate (3×15 mL) and the combined organic layers washed with brine (2×10 mL) and dried over Na$_2$SO$_4$. The mixture was concentrated under reduced pressure and the product isolated by flash column chromatography eluting with 6% to 60% ethyl acetate/hexane to provide 270 mg of the title compound as an colorless oil.

LC/MS: t$_R$=6.2 min. MS (API-ES) m/z 439 (M+H$^+$).

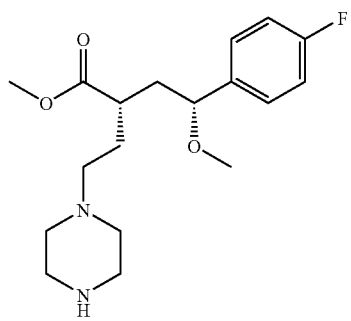

(2S,4R)-methyl 4-(4-fluorophenyl)-4-methoxy-2-(2-(piperazin-1-yl)ethyl)butanoate (Intermediate B8)

To a solution of tert-butyl 4-((3S,5R)-5-(4-fluorophenyl)-5-methoxy-3-(methoxycarbonyl)pentyl)piperazine-1-carboxylate in 200 μL DCM was slowly added 2 mL TFA and the resulting solution stirred for 30 min at 25° C. The solvent was evaporated under reduced pressure and the crude product was used directly in the next reaction without further purification.

LC/MS: $t_R$=3.7 min. MS (API-ES) m/z 339(M+H$^+$).

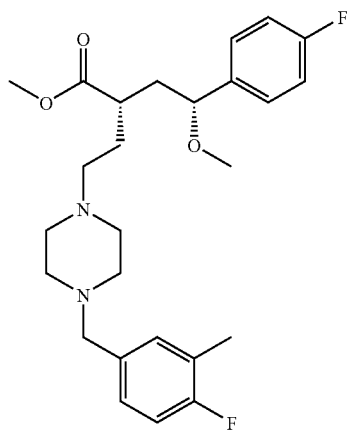

(2S,4R)-methyl 2-(2-(4-(4-fluoro-3-methylbenzyl)piperazin-1-yl)ethyl)-4-(4-fluorophenyl)-4-methoxybutanoate (Intermediate C8)

To a solution of (2S,4R)-methyl 4-(4-fluorophenyl)-4-methoxy-2-(2-(piperazin-1-yl)ethyl)butanoate (62 mg, 0.11 mmol) and 4-Fluoro-3-methyl-benzaldehyde (19.3 mg, 0.14 mmol) was added NaBH(OAc)$_3$ (32.5 mg, 0.15 mmol) and AcOH (6.6 mg, 6 μL, 0.11 mmol) at room temperature. The mixture was stirred for 8 h at the room temperature. The reaction was quenched by pouring into 20 mL 5% aqueous NaOH and diluted with ethylacetate. The mixture was extracted with more ethyl acetate (3×15 mL) and the combined organic layers washed with brine (2×10 mL) and dried over Na$_2$SO$_4$. The mixture was concentrated under reduced pressure and the crude product was used directly in the next reaction without further purification.

LC/MS: $t_R$=6.1 min. MS (API-ES) m/z 461 (M+H$^+$).

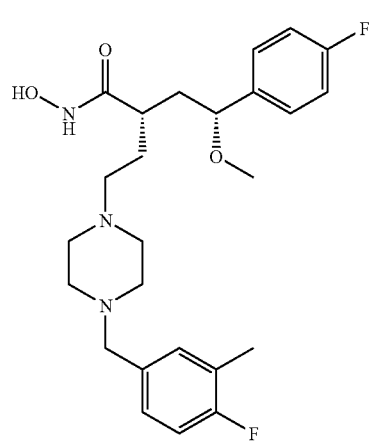

(2S,4R)-2-(2-(4-(4-fluoro-3-methylbenzyl)piperazin-1-yl)ethyl)-4-(4-fluorophenyl)-N-hydroxy-4-methoxybutanamide (Compound 167960)

To a solution of (2S,4R)-methyl 2-(2-(4-(4-fluoro-3-methylbenzyl)piperazin-1-yl)ethyl)-4-(4-fluorophenyl)-4-methoxybutanoate isolated above in 2 mL of THF, methanol, and 50 wt % NH$_2$OH in H$_2$O (2:2:1) was added KCN (4.0 mg, 0.06 mmol). The resulting mixture stirred for 3 days at room temperature. Evaporation of solvent left the crude product mixture from which the product was isolated RP-HPLC eluting with 80% to 2% CH$_3$CN/H$_2$O with 0.025% TFA to give the title compound, 14 mg, as colorless oil.

1H NMR (CD$_3$OD): δ 7.27 (m, 4H), 7.07 (m, 3H), 4.03 (dd, 1H, J=4.2 and 9.8), 3.86 (s, 2H), 3.17 (s, 3H), 3.13-2.77 (m, 9H), 2.52 (m, 1H), 2.27 (s, 3H), 2.02-1.62 (m, 4H).

LC/MS: $t_R$=4.5 min. MS (API-ES) m/z 462 (M+H$^+$).

Specific Scheme 9

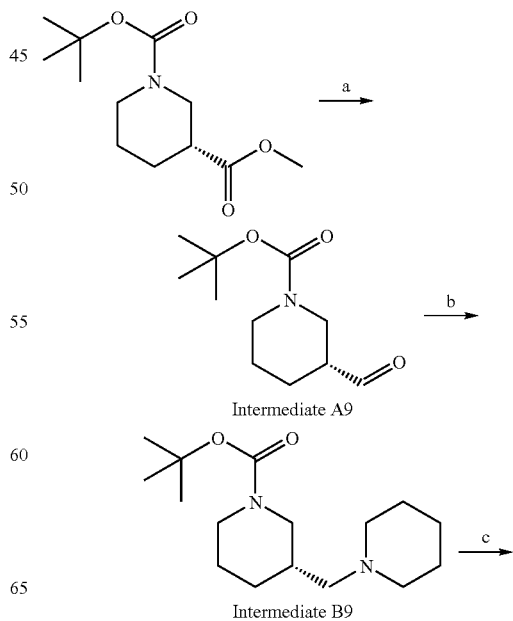

-continued

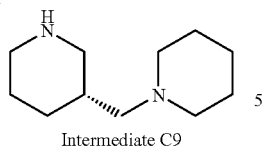

Intermediate C9

Reagents and conditions: a) DIBAL-H, DCM, -70 to 0° C., 40 min; b) piperidine, NaBH(OAc)₃, DCE, HOAc, 25° C., 8 h; d) TFA, DCM, 25° C., 1 h.

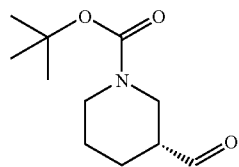

(R)-tert-butyl 3-formylpiperidine-1-carboxylate (Intermediate A9)

To a solution of (R)-1-tert-butyl 3-methyl piperidine-1,3-dicarboxylate (1.9 g, 7.3 mmol) in 60 mL DCM was slowly added DIBAL-H (22 mL, 1M in cyclohexane, 22 mmol) at −70° C. The mixture was further stirred at −70° C. for 20 min and the temperature was slowly raised to 0° C. over a period of 20 min. The reaction was quenched by pouring 4% aqueous $H_2SO_4$ (30 mL) and followed extraction with DCM (3×30 mL). The combined DCM layers were washed with 30 mL 4% aqueous $H_2SO_4$, 20 mL brine twice and dried over $Na_2SO_4$. The solvent was removed under reduced pressure and the product isolated by flash column chromatography eluting with 0% to 50% ethyl acetate/hexane gradient solvent to give the title compound, 732 mg, as colorless oil.

MS (EI) m/z 213(M⁺), 57(M−156) base peak.

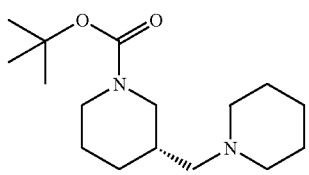

(S)-tert-butyl 3-(piperidin-1-ylmethyl)piperidine-1-carboxylate (Intermediate B9)

To a solution of (R)-tert-butyl 3-formylpiperidine-1-carboxylate (110 mg, 0.51 mmol) and piperidine (53 mg, 0.62 mmol) was added NaBH(OAc)₃ (153 mg, 0.73 mmol) and AcOH (37.2 mg, 35 µL, 0.62 mmol) at room temperature. The mixture was stirred for 8 h at the room temperature. The reaction was quenched by pouring into 20 mL 5% aqueous NaOH and diluted with ethylacetate. The mixture was extracted with ethyl acetate (3×15 mL) and the combined organic layers washed with brine (2×10 mL) and dried over $Na_2SO_4$. The mixture was concentrated under reduced pressure and the crude product was used directly in the next reaction without further purification.

MS (EI) m/z 282 (M⁺), 98(M−184) base peak.

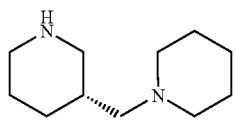

(R)-1-(piperidin-3-ylmethyl)piperidine (Intermediate C9)

To a solution of the (S)-tert-butyl 3-(piperidin-1-ylmethyl)piperidine-1-carboxylate isolated above in 200 µL DCM was slowly added 2 mL TFA and the resulting solution stirred for 30 min at 25° C. The solvent was evaporated and the crude product was used directly in the next reaction without further purification. (For example, reaction with Intermediate A5 in Specific Scheme 5)

MS (EI) m/z 182 (M⁺), 98(M-84) base peak.

Specific Scheme 10

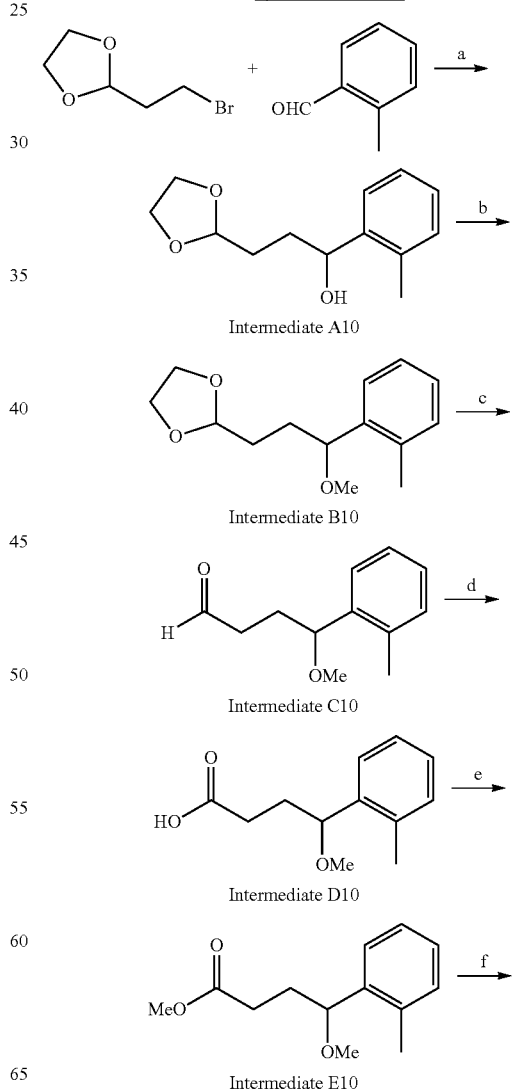

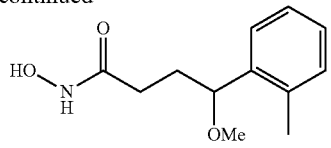

Compound 167540

Reagents and conditions: a) Mg, I₂, THF, -30-60° C., 3 h; b) MeI, NaH, THF, 25° C., 3 h; c) HCl, THF, 25° C., 12 h; d) Jones oxidation, acetone, THF, 25° C., 20 min; e) conc. H₂SO₄, MeOH, 25° C., 12 h; f) NH₂—OH, KCN, H₂O, MeOH, THF, 25° C., 24 h.

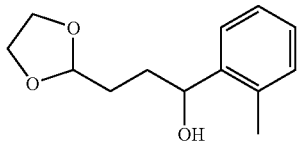

3-[1,3]-Dioxolan-2-yl-1-o-tolyl-propan-1-ol (Intermediate A10)

To a suspension of Mg turnings (134.0 mg, 5.6 mg-at.) and catalytic amount of iodine in 20 mL THF was added dropwise 2-(2-bromoethyl)-[1,3]dioxolane (500.0 mg, 2.8 mmol) with heating over a period of 30 min. After stirring the mixture for 30 min at 63° C. the reaction was cooled to −30° C. and 2-methyl-benzaldehyde (275.0 mg, 2.5 mmol) was slowly added as a solution in 5 mL THF. The temperature was maintained at −30° C. for 1 h and then slowly raised to room temperature over a period of 3 h. The excess Grignard reagent was destroyed by the careful addition of saturated aqueous NH₄Cl (40 mL). The resulting mixture was extracted with ethyl acetate (3×30 mL) and the combined organic layers washed with brine (2×20 mL). After evaporation of the solvent, the product was isolated by flash column chromatography eluting with 0 to 50% EtOAc/hexanes affording 290 mg of the title compound as a light yellow oil.

LC/MS: $t_R$=5.9 min. MS (API-ES) m/z 245 (M+H⁺+Na⁺).

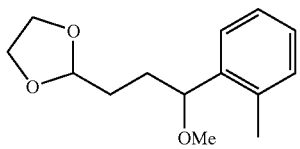

2-(3-Methoxy-3-o-tolyl-propyl)-[1,3]dioxolane (Intermediate B10)

To a suspension of NaH (468 mg of a 60% dispersion in mineral oil, 11.7 mmol) in 35 mL THF was slowly added 3-[1,3]Dioxolan-2-yl-1-o-tolyl-propan-1-ol (290.0 mg, 1.3 mmol) as a solution in 15 mL THF at room temperature followed by the dropwise addition of methyl iodide (624 L, 1.4 g, 9.6 mmol). The mixture was stirred for 3 h at room temperature before being quenched by the careful addition of saturated aqueous NH₄Cl (40 mL). The resulting mixture was extracted with ethyl acetate (3×30 mL) and the combined organic layers washed with brine (2×20 mL) and dried over sodium sulfate. The solvents were evaporated under reduced pressure and the product isolated by flash column chromatography eluting with 0% to 30% ethyl acetate/hexane to give 285 mg of the title compounds as an oil.

LC/MS: $t_R$=8.4 min. MS (API-ES) m/z 205(M+H⁺-31).

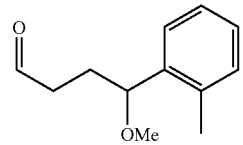

4-Methoxy-4-o-tolyl-butyraldehyde (Intermediate C10)

To a solution of 2-(3-Methoxy-3-o-tolyl-propyl)-[1,3]dioxolane (285.0 mg, 1.2 mmol) in 14 mL THF was added 7 mL 1M aqueous HCl at room temperature. After stirring the mixture for 12 h, water was added and the solution extracted with ethyl acetate (3×20 mL). The combined organic layers were washed with brine (2×10 mL) and dried over Na₂SO₄. Evaporation of solvent provided the desired product as an oil which was used directly in the next experiment without further purification.

LC/MS: $t_R$=7.6 min. MS (API-ES) m/z 162 (M+H⁺—OMe).

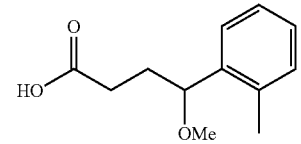

4-Methoxy-4-o-tolyl-butyric acid (Intermediate D10)

To a solution of 4-Methoxy-4-o-tolyl-butyraldehyde obtained above in 11 mL acetone was added 1.1 mL of Jones reagent dropwise at room temperature. The mixture was stirred for 30 min, diluted with water and extracted with DCM (3×30 mL). The combined DCM layers were washed with water (2×20 mL) and dried over Na₂SO₄. The solvents were evaporated under reduce pressure and the crude product was used for the next step without further purification.

LC/MS: $t_R$=6.5 min. MS (API-ES) m/z 231 (M+H⁺+Na⁺).

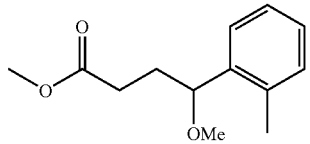

4-Methoxy-4-o-tolyl-butyric acid methyl ester (Intermediate E10)

To a solution of the 4-methoxy-4-o-tolyl-butyric acid obtained above in 6 mL methanol was added 60 µL concentrated H₂SO₄ at room temperature. After stirring for 12 h the reaction mixture was concentrated under reduced pressure. Water was added to the residue and the mixture extracted with ethyl acetate (3×20 mL). The combined organic layers were washed with brine (2×10 mL) and dried over Na$_2$SO$_4$. The product was isolated by flash column chromatography eluting with 0% to 10% ethyl acetate/hexane to give 229 mg of the title compound as an oil.

LC/MS: $t_R$=8.6 min. MS (API-ES) m/z 245 (M+H$^+$+Na$^+$).

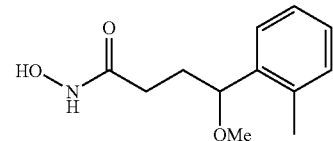

N-hydroxy-4-methoxy-4-o-tolylbutanamide (Compound 167540)

To a solution prepared by dissolving 4-methoxy-4-o-tolyl-butyric acid methyl ester (230.0 mg, 1.03 mmol) into 3 mL of a mixture of THF, methanol, and 50 wt % NH$_2$OH in H$_2$O (2:2:1) was added KCN (6.0 mg, 0.03 mmol). The reaction mixture was stirred for 3 days at room temperature and then quenched by the addition of 10 mL of 1M aqueous HCl. The mixture was extracted with ethyl acetate (3×20 mL) and the combined organic layers washed with brine (2×10 mL). The product was isolated by flash column chromatography eluting with 0% to 10% methanol/DCM to afford 184 mg of the title compound as a yellow oil.

LC/MS: $t_R$=4.5 min. MS (API-ES) m/z 246 (M+H$^+$+Na$^+$).

Specific Scheme 11

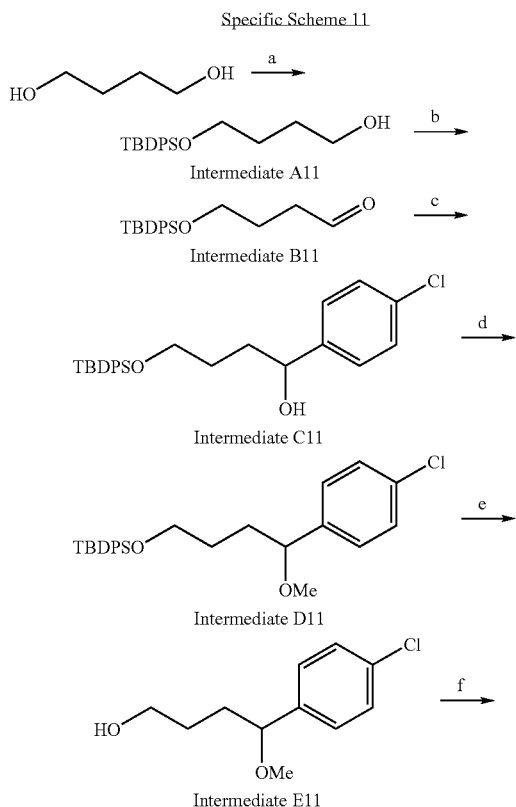

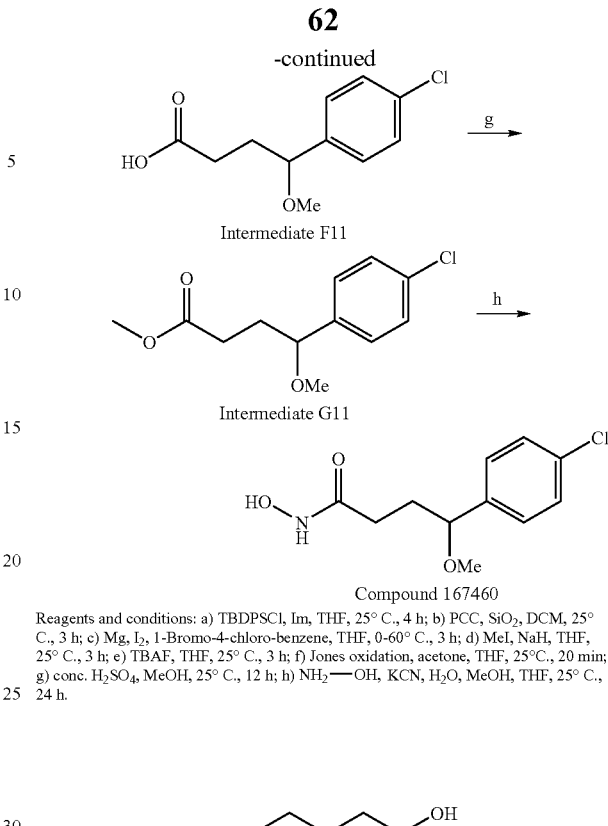

Reagents and conditions: a) TBDPSCl, Im, THF, 25° C., 4 h; b) PCC, SiO$_2$, DCM, 25° C., 3 h; c) Mg, I$_2$, 1-Bromo-4-chloro-benzene, THF, 0-60° C., 3 h; d) MeI, NaH, THF, 25° C., 3 h; e) TBAF, THF, 25° C., 3 h; f) Jones oxidation, acetone, THF, 25°C., 20 min; g) conc. H$_2$SO$_4$, MeOH, 25° C., 12 h; h) NH$_2$—OH, KCN, H$_2$O, MeOH, THF, 25° C., 24 h.

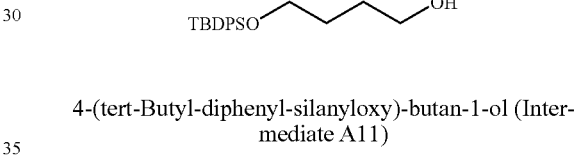

4-(tert-Butyl-diphenyl-silanyloxy)-butan-1-ol (Intermediate A11)

To a solution of 1,4-butanediol (4.0 g, 44.4 mmol) in 250 mL THF was added imidazole (3.7 g, 54.3 mmol) followed by tert-butyl(chloro)diphenylsilane (10 g, 36.4 mmol) at room temperature. The mixture was stirred for 3 h and then quenched by the addition of saturated aqueous NH$_4$Cl (200 mL) and then diluted with ethyl acetate (200 mL). The mixture was extracted with ethyl acetate (3×200 mL) and the combined organic layers washed with brine (3×60 mL) and dried over Na$_2$SO$_4$. The solvent was evaporated and the product isolated by flash column chromatography eluting with 0 to 50% EtOAc/hexanes to give 10.6 g of the title compound as a colorless oil.

LC/MS: $t_R$=11.4 min. MS (API-ES) m/z 329 (M+H$^+$).

4-(tert-Butyl-diphenyl-silanyloxy)-butyraldehyde (Intermediate B11)

To a suspension of 9.0 g silica gel and PCC (7.7 g, 35.7 mmol) in 300 mL DCM was added 4-(tert-Butyl-diphenyl-silanyloxy)-butan-1-ol (6.0 g, 18.3 mmol) in 50 mL DCM. The mixture was stirred for 3 h at room temperature and then the resulting suspension filtered thorough a pad of celite/florisil and rinsed with DCM. The solvent was evaporated and the product was isolated by flash column chromatography eluting with 0% to 30% ethyl acetate/hexane to give the title compound (4.7 g) as a light yellow oil.

LC/MS: $t_R$=12.0 min. MS (API-ES) m/z 327 (M+H$^+$).

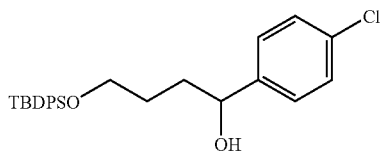
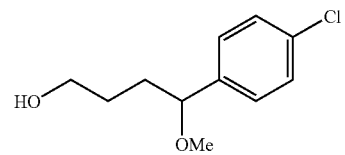

4-(tert-Butyl-diphenyl-silanyloxy)-1-(4-chloro-phenyl)-butan-1-ol (Intermediate C11)

To a suspension of Mg turnings (145 mg, 6.0 mg-at.) and catalytic amount of iodine in 20 mL THF was added dropwise 1-Bromo-4-chloro-benzene (382 mg, 2.0 mmol) with heating over a period of 30 min. After stirring for an additional 30 min at 63° C. the mixture was cooled to −30° C. and 4-(tert-Butyl-diphenyl-silanyloxy)-butyraldehyde (500 mg, 1.53 mmol) was added slowly as a solution in 5 mL THF. The temperature was maintained at −30° C. for 1 h and slowly raised to room temperature. The excess Grignard reagent was destroyed by careful addition of saturated aqueous NH$_4$Cl (20 mL). The mixture was extracted with ethyl acetate (3×30 mL) and the combined organic layers washed with brine (2×20 mL). After removal of the solvent under reduced pressure the product was isolated by flash column chromatography eluting with 0 to 50% EtOAc/hexanes to afford 330 mg of the title compound as a light yellow oil.

LC/MS: $t_R$=13.0 min. MS (API-ES) m/z 462 (M+H$^+$+Na$^+$).

4-(4-Chloro-phenyl)-4-methoxy-butan-1-ol (Intermediate E11)

To a solution of tert-butyl-[4-(4-chloro-phenyl)-4-methoxy-butoxy]-diphenyl-silane (343 mg, 0.75 mmol) in 20 mL THF was added at room temperature TBAF (7.5 mL, 7.5 mmol, 1M in THF). The mixture was stirred for 3 h and the reaction quenched by the addition of 10 mL saturated aqueous NH$_4$Cl. The mixture was extracted with ethyl acetate (3×15 mL) and the combined organic layers washed with brine (2×10 mL) and dried over Na$_2$SO$_4$. The mixture was concentrated and the product isolated by flash column chromatography eluting with 6% to 60% ethyl acetate/hexane to provide 120 mg of the title compound.

LC/MS: $t_R$=6.7 min. MS (API-ES) m/z 165 (M+H$^+$-18-31).

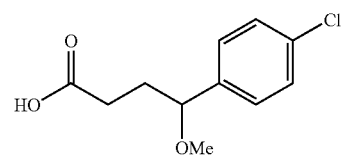

4-(4-Chloro-phenyl)-4-methoxy-butyric acid (Intermediate F11)

A solution of 4-(4-chloro-phenyl)-4-methoxy-butan-1-ol (120.0 mg, 0.56 mmol) in 6 mL acetone was added dropwise at room temperature 0.6 mL of Jones reagent. After stirring an additional 30 min water was added and the mixture extracted with DCM (3×20 mL). The combined DCM layers were washed with water (2×10 mL) and dried over Na$_2$SO$_4$. The solvent was evaporated under reduce pressure and the crude product was used for the next step without further purification.

LC/MS: $t_R$=5.4 min. MS (API-ES) m/z 251 (M+H$^+$+Na$^+$).

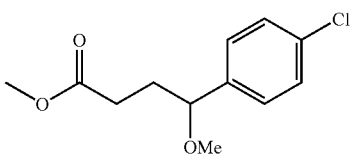

tert-Butyl-[4-(4-chloro-phenyl)-4-methoxy-butoxy]-diphenyl-silane (Intermediate D11)

To a suspension of NaH (153 mg 60% dispersed in mineral oil, 6.39 mmol) in 20 mL THF was slowly added at room temperature 4-(tert-butyl-diphenyl-silanyloxy)-1-(4-chloro-phenyl)-butan-1-ol (330 mg, 0.75 mmol) as a solution in 10 mL THF followed by the dropwise addition of methyl iodide (339 µL, 5.25 mmol). The reaction mixture was stirred for 3 h at room temperature before being quenched by the careful addition of saturated aqueous NH$_4$Cl (30 mL). The mixture was extracted with ethylacetate (3×30 mL) and the combined organic layers washed with brine (2×20 mL) and dried over sodium sulfate. After evaporation of solvent the product was isolated by flash column chromatography eluting with 0% to 30% ethyl acetate/hexane to give 343 mg of the title compound as a colorless oil.

LC/MS: $t_R$=14.8 min. MS (API-ES) m/z 475 (M+H$^+$+Na$^+$).

4-(4-Chloro-phenyl)-4-methoxy-butyric acid methyl ester (Intermediate G11)

To a solution 4-(4-chloro-phenyl)-4-methoxy-butyric acid obtained in the previous experiment in 4 mL methanol was added 20 µL concentrated H$_2$SO$_4$ at room temperature and the resulting mixture stirred for an additional 12 h. The mixture was concentrated under reduced pressure and 5 mL water was added. Extraction with ethyl acetate (3×10 mL) was followed by washing the combined organic layers with brine (2×25 mL) and drying over Na$_2$SO$_4$. The product was isolated by flash column chromatography eluting with 0% to 10% ethyl acetate/hexane to give the title compound (76.8 mg) as an oil.

LC/MS: t$_R$=6.7 min. MS (API-ES) m/z 207 (M+H$^+$-31).

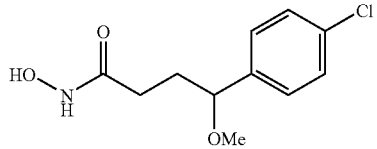

4-(4-chlorophenyl)-N-hydroxy-4-methoxybutanamide (Compound 167460)

To a solution of 4-(4-chloro-phenyl)-4-methoxy-butyric acid methyl ester (62.5 mg, 0.25 mmol) dissolved in 2 mL of THF, methanol, and 50 wt % NH$_2$OH in H$_2$O (2:2:1) mixture was added KCN (4.0 mg, 0.06) and the resulting mixture stirred for 3 days at room temperature. The reaction was quenched by the addition of 1M aqueous HCl (10 mL) and the resulting mixture extracted with ethyl acetate (3×10 mL). The combined organic layers were washed with brine (2×5 mL). The product was isolated by flash column chromatography eluting with 0% to 10% methanol/DCM to give the title compound (34 mg) as colorless oil.

1H NMR (CD$_3$OD): δ 7.36 (d, 2H, J=8.4), 7.27 (d, 2H, J=8.4), 4.15 (t, 1H, J=6.4), 3.19 (s, 3H), 2.14 (t, 2H, J=7.9), 1.94 (m, 2H).

LC/MS: t$_R$=5.0 min. MS (API-ES) m/z 243 (M+H$^+$).

ABBREVIATIONS

DCM=Dichloromethane
DCE=1,2-dichloroethane
DMF=dimethylformamide
HOBt=1-hydroxybenzotriazole
NMM=N-methylmorpholine
EDC=N-(-dimethylaminopropyl)-N'-ethylcarbodiimide
DCM=dichloromethane
TFA=trifluoroacetic acid
TBDPSCl=tert-butyl(chloro)diphenylsilane
Im=imidazole
PCC=pyridinium chlorochromate
TBAF=tetrabutylammonium fluoride
Jone's Reagent=H$_2$CrO$_4$/H$_2$SO$_4$/H$_2$O
Characterizing Data for Compounds in Table 1

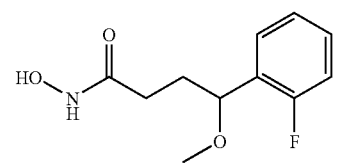

4-(2-fluorophenyl)-N-hydroxy-4-methoxybutanamide (Compound 167564) Prepared according to General Scheme 8

LC/MS: t$_R$=4.0 min. MS (API-ES) m/z 228 (M+H$^+$+Na$^+$).

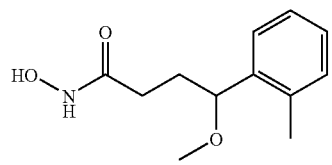

N-hydroxy-4-methoxy-4-o-tolylbutanamide (Compound 167540) Prepared according to General Scheme 8

LC/MS: t$_R$=4.5 min. MS (API-ES) m/z 246 (M+H$^+$+Na$^+$).

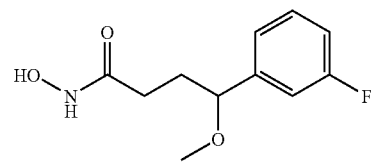

4-(3-fluorophenyl)-N-hydroxy-4-methoxybutanamide (Compound 167456)

Prepared according to General Scheme 9

LC/MS: t$_R$=4.2 min. MS (API-ES) m/z 250 (M+H$^+$+Na$^+$).

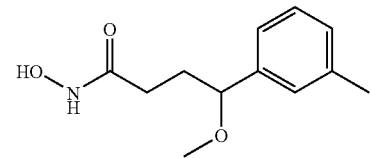

N-hydroxy-4-methoxy-4-m-tolylbutanamide (Compound 167491) Prepared according to General Scheme 9

LC/MS: t$_R$=8.6 min. MS (API-ES) m/z 246 (M+H$^+$+Na$^+$).

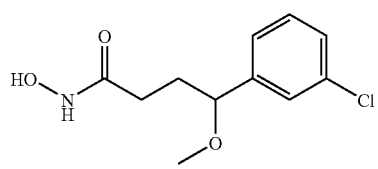

4-(3-chlorophenyl)-N-hydroxy-4-methoxybutanamide (Compound 167461) Prepared according to General Scheme 9

LC/MS: t$_R$=5.0 min. MS (API-ES) m/z 266 (M+H$^+$+Na$^+$).

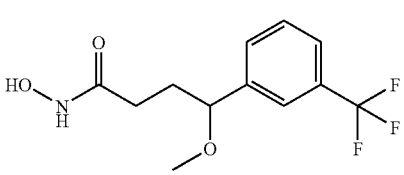

N-hydroxy-4-methoxy-4-(3-(trifluoromethyl)phenyl)bu-tanamide (Compound 167492) Prepared according to General Scheme 9.

LC/MS: t$_R$=5.6 min. MS (API-ES) m/z 278 (M+H$^+$).

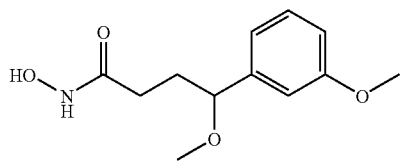

N-hydroxy-4-methoxy-4-(3-methoxyphenyl)butanamide (Compound 167458) Prepared according to General Scheme 9.

LC/MS: $t_R$=3.9 min. MS (API-ES) m/z 262 (M+H$^+$+Na$^+$).

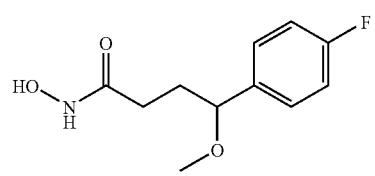

4-(4-fluorophenyl)-N-hydroxy-4-methoxybutanamide (Compound 167157) Prepared according to General Scheme 9.

LC/MS: $t_R$=3.8 min.
MS (API-ES) m/z 250 (M+H$^+$+Na$^+$).

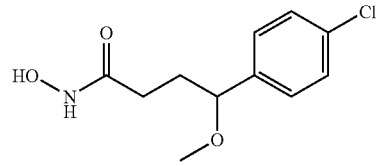

4-(4-chlorophenyl)-N-hydroxy-4-methoxybutanamide (Compound 167460) Prepared according to General Scheme 9.

LC/MS: $t_R$=5.1 min. MS (API-ES) m/z 266 (M+H$^+$+Na$^+$).

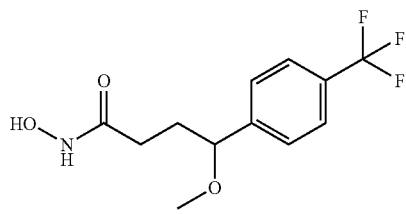

N-hydroxy-4-methoxy-4-(4-(trifluoromethyl)phenyl)butanamide (Compound 167511) Prepared according to General Scheme 9.

LC/MS: $t_R$=5.7 min. MS (API-ES) m/z 278 (M+H$^+$).

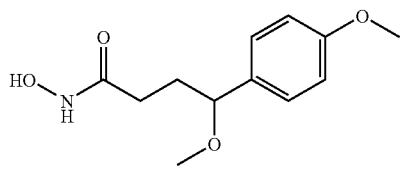

N-hydroxy-4-methoxy-4-(4-methoxyphenyl)butanamide (Compound 167457) Prepared according to General Scheme 9.

LC/MS: $t_R$=3.6 min. MS (API-ES) m/z 262 (M+H$^+$+Na$^+$).

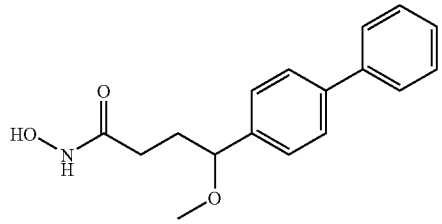

4-(biphenyl-4-yl)-N-hydroxy-4-methoxybutanamide (Compound 167506) Prepared according to General Scheme 9.

LC/MS: $t_R$=6.4 min. MS (API-ES) m/z 308 (M+H$^+$+Na$^+$).

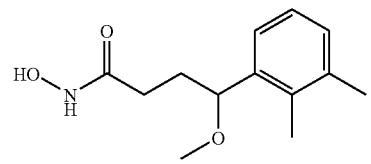

4-(2,3-dimethylphenyl)-N-hydroxy-4-methoxybutanamide (Compound 167495) Prepared according to General Scheme 9.

LC/MS: $t_R$=5.2 min. MS (API-ES) m/z 260 (M+H$^+$+Na$^+$).

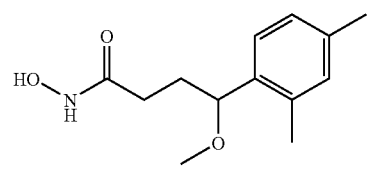

4-(2,4-dimethylphenyl)-N-hydroxy-4-methoxybutanamide (Compound 167541) Prepared according to General Scheme 8.

LC/MS: $t_R$=5.3 min. MS (API-ES) m/z 260 (M+H$^+$+Na$^+$).

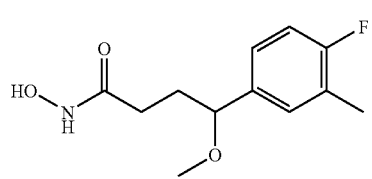

4-(4-fluoro-3-methylphenyl)-N-hydroxy-4-methoxybutanamide (Compound 167232) Prepared according to General Scheme 1.

LC/MS: $t_R$=4.9 min. MS (API-ES) m/z 264 (M+H$^+$+Na$^+$).

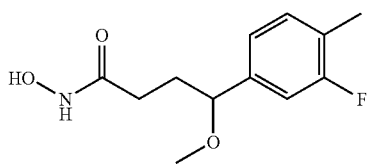

4-(3-fluoro-4-methylphenyl)-N-hydroxy-4-methoxybutanamide (Compound 167463) Prepared according to General Scheme 9.

LC/MS: $t_R$=6.5 min. MS (API-ES) m/z 264 (M+H$^+$+Na$^+$).

Characterizing Data for Compounds in Table 2

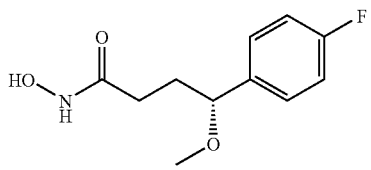

(R)-4-(4-fluorophenyl)-N-hydroxy-4-methoxybutanamide (Compound 167204) Prepared according to General Scheme 1.

LC/MS: $t_R$=4.1 min. MS (API-ES) m/z 250 (M+H$^+$+Na$^+$).

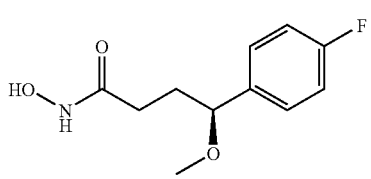

(S)-4-(4-fluorophenyl)-N-hydroxy-4-methoxybutanamide (Compound 167205) Prepared according to General Scheme 1.

LC/MS: $t_R$=4.1 min. MS (API-ES) m/z 250 (M+H$^+$+Na$^+$).

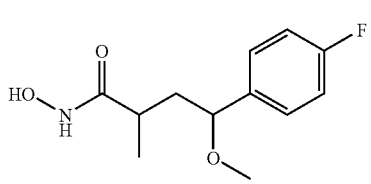

4-(4-Fluoro-phenyl)-N-hydroxy-4-methoxy-2-methyl-butyramide (Compound 167288) Prepared according to General Scheme 2.

LC/MS: $t_R$=4.5 min. MS (API-ES) m/z 278 (M+H$^+$+Na$^+$).

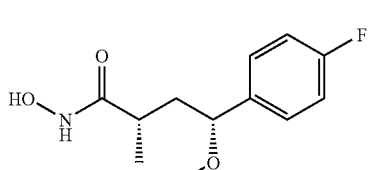

(2S,4R)-4-(4-fluorophenyl)-N-hydroxy-4-methoxy-2-methylbutanamide (Compound 167297) Prepared according to General Scheme 4.

LC/MS: $t_R$=4.5 min. MS (API-ES) m/z 264 (M+H$^+$+Na$^+$).

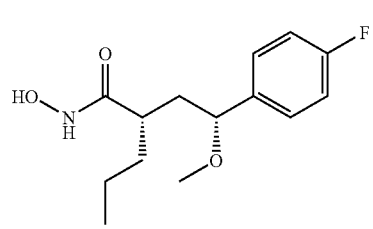

(S)-2-((R)-2-(4-fluorophenyl)-2-methoxyethyl)-N-hydroxypentanamide (Compound 167432) Prepared according to General Scheme 4.

LC/MS: $t_R$=5.9 min. MS (API-ES) m/z 292 (M+H$^+$+Na$^+$).

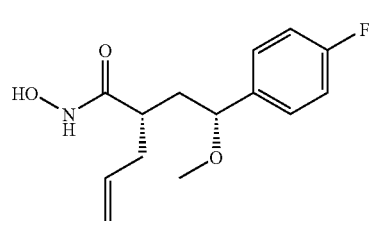

(2S)-2-((2R)-2-(4-fluorophenyl)-2-methoxyethyl)-N-hydroxypent-4-enamide (Compound 167434) Prepared according to General Scheme 4.

LC/MS: $t_R$=5.6 min. MS (API-ES) m/z 290 (M+H$^+$+Na$^+$).

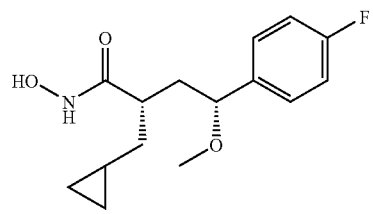

(2S,4R)-2-(cyclopropylmethyl)-4-(4-fluorophenyl)-N-hydroxy-4-methoxybutanamide (Compound 167433) Prepared according to General Scheme 4.

LC/MS: $t_R$=6.0 min. MS (API-ES) m/z 304 (M+H$^+$+Na$^+$).

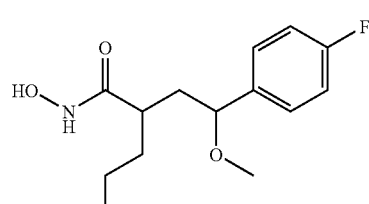

2-Benzyl-4-(4-fluorophenyl)-N-hydroxy-4-methoxy-butyramide (Compound 167287) Prepared according to General Scheme 4.

LC/MS: $t_R$=6.5 min. MS (API-ES) m/z 306 (M+H$^+$+Na$^+$).

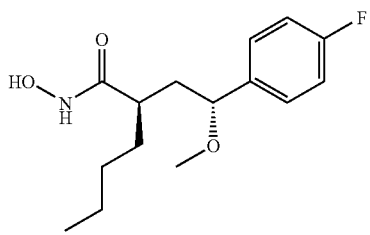

(2R)-2-((2R)-2-(4-fluorophenyl)-2-methoxyethyl)-N-hydroxyhexanamide (Compound 167353) Prepared according to General Scheme 4

LC/MS: $t_R$=6.6 min. MS (API-ES) m/z 252 (M+H$^+$—OMe).

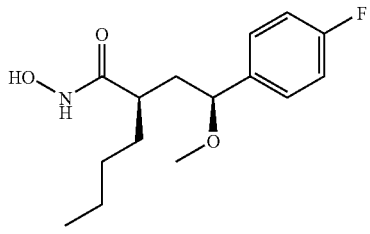

(2R)-2-((2S)-2-(4-fluorophenyl)-2-methoxyethyl)-N-hydroxyhexanamide (Compound 167389) Prepared according to General Scheme 4.

LC/MS: $t_R$=6.7 min. MS (API-ES) m/z 306 (M+H$^+$+Na$^+$).

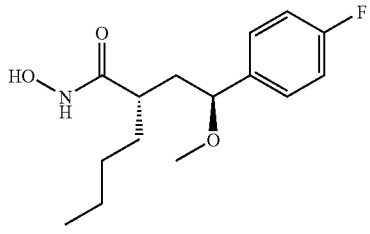

(2S)-2-((2S)-2-(4-fluorophenyl)-2-methoxyethyl)-N-hydroxyhexanamide (Compound 167390) Prepared according to General Scheme 4.

LC/MS: $t_R$=6.5 min. MS (API-ES) m/z 306 (M+H$^+$+Na$^+$).

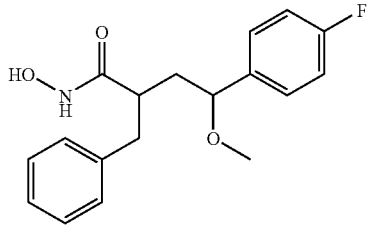

2-Benzyl-4-(4-fluorophenyl)-N-hydroxy-4-methoxy-butyramide (Compound 167286) Prepared according to General Scheme 4.

MS (API-ES) m/z 332 (M+H$^+$).

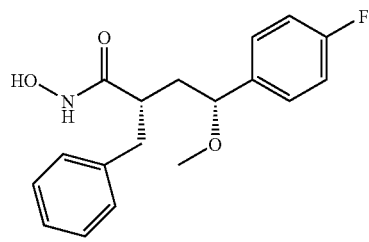

2S,4R)-2-Benzyl-4-(4-fluoro-phenyl)-N-hydroxy-methoxy-butyramide (Compound 167298) Prepared according to General Scheme 4.

LC/MS: $t_R$=6.7 min. MS (API-ES) m/z 340 (M+H$^+$+Na$^+$).

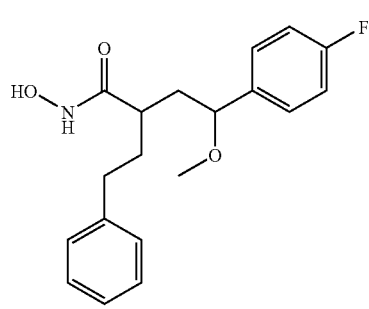

4-(4-fluorophenyl)-N-hydroxy-4-methoxy-2-phenethylbutanamide (Compound 167308) Prepared according to General Scheme 4.

LC/MS: $t_R$=6.5 min. MS (API-ES) m/z 354 (M+H$^+$+Na$^+$).

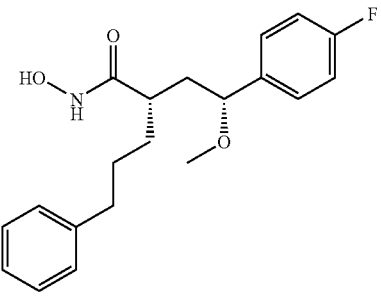

(2S)-2-((2R)-2-(4-fluorophenyl)-2-methoxyethyl)-N-hydroxy-5-phenylpentanamide (Compound 167337) Prepared according to General Scheme 4.

LC/MS: $t_R$=7.8 min. MS (API-ES) m/z 346 (M+H$^+$).

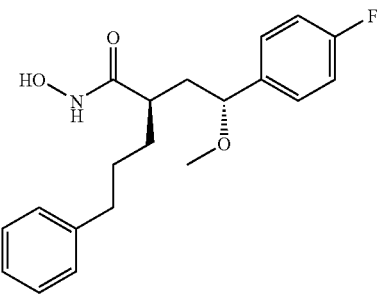

(2R)-2-((2R)-2-(4-fluorophenyl)-2-methoxyethyl)-N-hydroxy-5-phenylpentanamide (Compound 167395) Prepared according to General Scheme 4.

LC/MS: $t_R$=7.6 min. MS (API-ES) m/z 368 (M+H$^+$+Na$^+$).

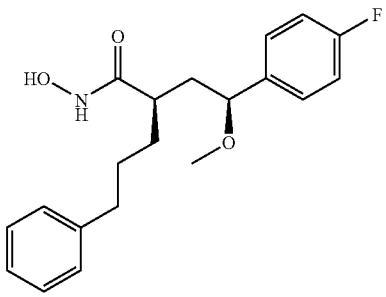

(2R)-2-((2S)-2-(4-fluorophenyl)-2-methoxyethyl)-N-hydroxy-5-phenylpentanamide (Compound 167341) Prepared according to General Scheme 4.

LC/MS: $t_R$=7.8 min. MS (API-ES) m/z 346 (M+H$^+$).

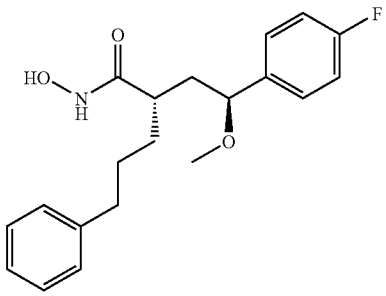

(2S)-2-(2S)-2-(4-fluorophenyl)-2-methoxyethyl)-N-hydroxy-5-phenylpentanamide (Compound 167408) Prepared according to General Scheme 4.

LC/MS: $t_R$=7.6 min. MS (API-ES) m/z 368 (M+H$^+$+Na$^+$).

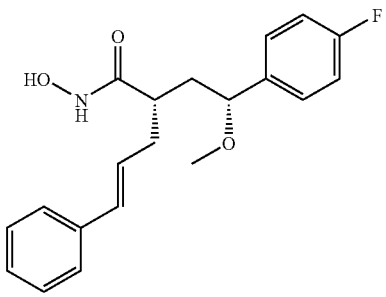

(2S,4E)-2-(2R)-2-(4-fluorophenyl)-2-methoxyethyl)-N-hydroxy-5-phenylpent-4-enamide (Compound 167354) Prepared according to General Scheme 4.

LC/MS: $t_R$=7.7 min. MS (API-ES) m/z 344 (M+H$^+$).

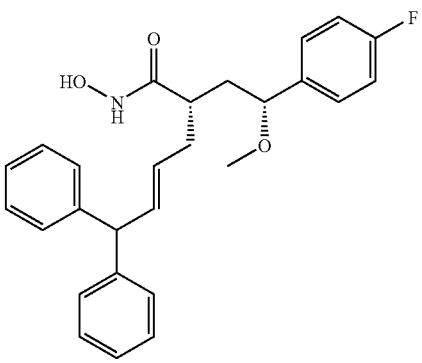

(2S,4E)-2-((2R)-2-(4-fluorophenyl)-2-methoxyethyl)-N-hydroxy-6,6-diphenylhex-4-enamide (Compound 167371) Prepared according to General Scheme 4.

LC/MS: $t_R$=9.3 min. MS (API-ES) m/z 434 (M+H$^+$).

Characterizing Data for Compounds in Table 3

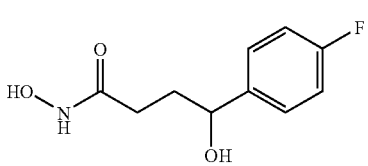

4-(4-fluorophenyl)-N,4-dihydroxybutanamide (Compound 166976) Prepared according to General Scheme 1.

LC/MS: $t_R$=1.9 min. MS (API-ES) m/z 236 (M+H$^+$+Na$^+$).

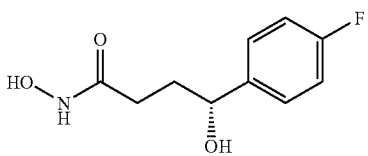

(R)-4-(4-fluorophenyl)-N,4-dihydroxybutanamide (Compound 167206) Prepared according to General Scheme 1.

LC/MS: $t_R$=1.8 min. MS (API-ES) m/z 236 (M+H$^+$+Na$^+$).

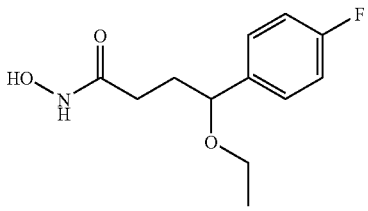

4-ethoxy-4-(4-fluorophenyl)-N-hydroxybutanamide (Compound 167173)

LC/MS: $t_R$=4.9 min. MS (API-ES) m/z 264 (M+H$^+$+Na$^+$).

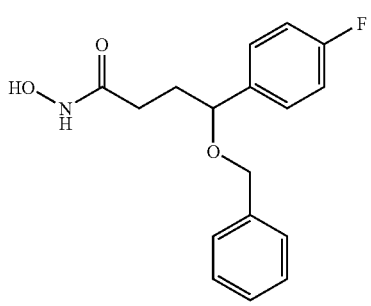

4-(benzyloxy)-4-(4-fluorophenyl)-N-hydroxybutanamide (Compound 167151)

LC/MS: $t_R$=6.8 min. MS (API-ES) m/z 304 (M+H$^+$).

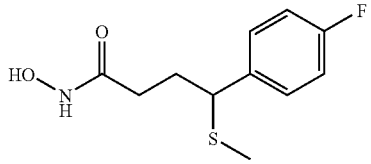

4-(4-Fluoro-phenyl)-N-hydroxy-4-methylsulfanyl-butyramide (Compound 167366) Prepared according to General Scheme 6.

LC/MS: $t_R$=5.2 min. MS (API-ES) m/z 266 (M+H$^+$+Na$^+$).
Characterizing Data for Compounds in Table 4

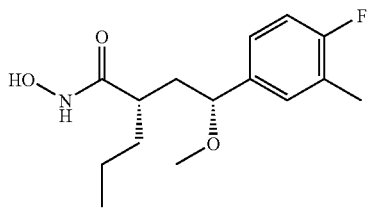

(2S)-2-((2R)-2-(4-fluoro-3-methylphenyl)-2-methoxyethyl)-N-hydroxypentanamide (Compound 167675) Prepared according to General Scheme 4.

LC/MS: $t_R$=6.6 min. MS (API-ES) m/z 252 (M—OMe).

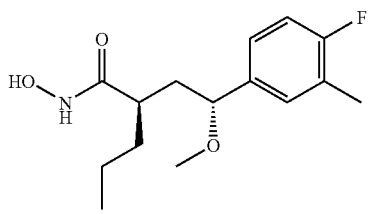

(2R)-2-((2R)-2-(4-fluoro-3-methylphenyl)-2-methoxyethyl)-N-hydroxypentanamide (Compound 167674) Prepared according to General Scheme 4.

LC/MS: $t_R$=6.4 min. MS (API-ES) m/z 252 (M$^+$—OMe)

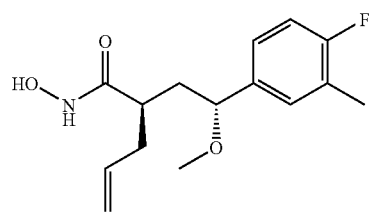

(2R)-2-((2R)-2-(4-fluoro-3-methylphenyl)-2-methoxyethyl)-N-hydroxypent-4-enamide (Compound 167672) Prepared according to General Scheme 4.

LC/MS: $t_R$=6.1 min. MS (API-ES) m/z 250 (M-OMe).
Characterizing Data for Compounds in Table 5

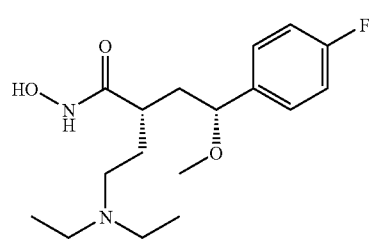

(2S,4R)-2-(2-(diethylamino)ethyl)-4-(4-fluorophenyl)-N-hydroxy-4-methoxybutanamide (COMPOUND 167995) Prepared according to General Scheme 5.

$^1$H-NMR (CD$_3$OD): δ 7.29 (dd, 2H, J=5.4 and 8.4), 7.09 (t, 2H, J=8.5), 4.06 (dd, 1H, J=4.2 and 9.3), 3.27-3.11 (m, 8H), 2.97 (m, 1H), 2.57 (m, 1H), 2.02-1.78 (m, 4H), 1.33-1.27 (m, 6H); LC/MS: $t_R$=3.1 min. MS (API-ES) m/z 327 (M+H$^+$).

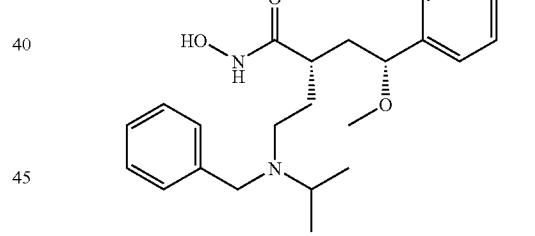

(2S,4R)-2-(2-(benzyl(isopropyl)amino)ethyl)-4-(4-fluorophenyl)-N-hydroxy-4-methoxybutanamide (Compound 167784) Prepared according to General Scheme 5.

LC/MS: $t_R$=4.9 min. MS (API-ES) m/z 403 (M+H$^+$).

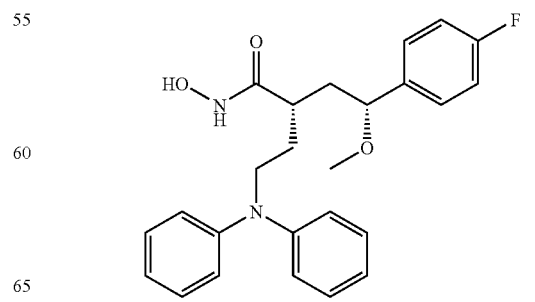

(2S,4R)-2-(2-(diphenylamino)ethyl)-4-(4-fluorophenyl)-N-hydroxy-4-methoxybutanamide (COMPOUND 167796) Prepared according to General Scheme 5.

1H NMR (CD$_3$OD): δ 7.23 (m, 6H), 7.04 (t, 2H, J=8.8), 6.93 (m, 6H), 4.02 (dd, 1H, J=3.6 and 9.87), 3.66 (t, 2H, J=8.1), 3.16 (s, 3H), 2.51 (m, 1H), 2.01-1.65 (m, 4H); LC/MS: t$_R$=9.5 min. MS (API-ES) m/z 423 (M+H$^+$).

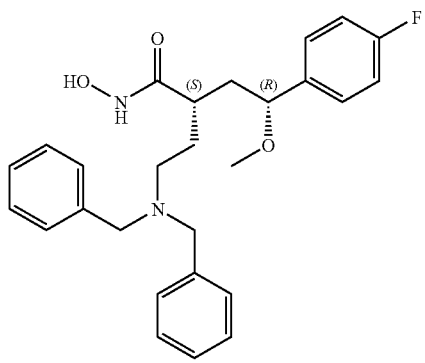

(2S,4R)-2-(2-(dibenzylamino)ethyl)-4-(4-fluorophenyl)-N-hydroxy-4-methoxybutanamide (COMPOUND 167996) Prepared according to General Scheme 5.

$^1$H-NMR (CD$_3$OD): δ 7.53 (m, 6H), 7.39 (m, 4H), 7.17 (dd, 2H, J=5.5 and 8.7), 7.08 (t, 2H, J=8.8), 4.51 (d, 1H, J=3.4), 4.39 (d, 1H, J=9.5), 4.28 (d, 1H, J=12.6), 4.10 (d, 1H, J=14.3), 3.89 (dd, 1H, J=2.6 and 10.9), 3.14 (m, 6H), 2.56 (m, 1H), 2.06 (m, 2H), 1.56-1.24 (m, 2H); LC/MS: t$_R$=6.0 min. MS (API-ES) m/z 451 (M+H$^+$).

Characterizing Data for Compounds in Table 6

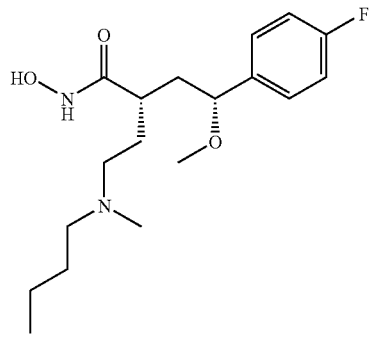

(2S,4R)-2-(2-(butyl(methyl)amino)ethyl)-4-(4-fluorophenyl)-N-hydroxy-4-methoxybutanamide (Compound 167828) Prepared according to General Scheme 5.

LC/MS: t$_R$=4.1 min. MS (API-ES) m/z 341 (M+H$^+$).

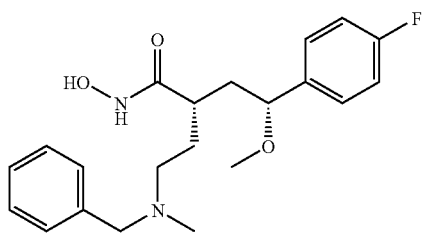

(2S,4R)-2-(2-(benzyl(methyl)amino)ethyl)-4-(4-fluorophenyl)-N-hydroxy-4-methoxybutanamide (Compound 167785) Prepared according to General Scheme 5.

LC/MS: t$_R$=4.4 min. MS (API-ES) m/z 375 (M+H$^+$).

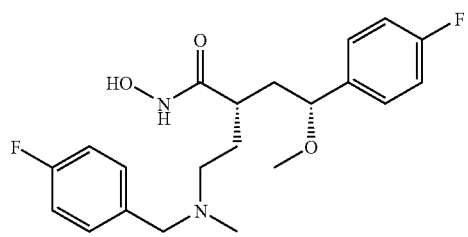

(2S,4R)-2-(2-((4-fluorobenzyl)(methyl)amino)ethyl)-4-(4-fluorophenyl)-N-hydroxy-4-methoxybutanamide (Compound 167795) Prepared according to General Scheme 5.

LC/MS: t$_R$=4.6 min. MS (API-ES) m/z 393 (M+H$^+$).

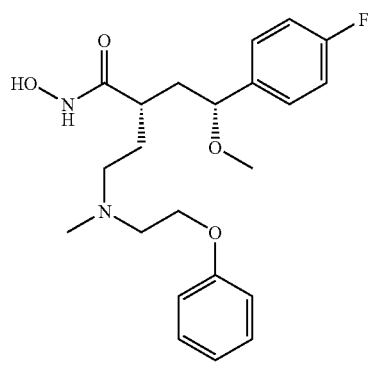

(2S,4R)-4-(4-fluorophenyl)-N-hydroxy-4-methoxy-2-(2-(methyl(2-phenoxyethyl)amino)ethyl)butanamide (COMPOUND 167890) Prepared according to General Scheme 5.

$^1$H-NMR (CD$_3$OD): δ 7.29 (m, 6H), 7.11-6.99 (m, 5H), 4.33 (t, 2H, J=4.3), 4.04 (dd, 1H, J=3.6 and 9.9), 3.73-3.52 (m, 2H), 3.24 (m, 1H), 3.17 (m, 4H), 2.95 (m, 1H), 2.11-1.80 (m, 4H); LC/MS: t$_R$=5.0 min. MS (API-ES) m/z 405 (M+H$^+$).

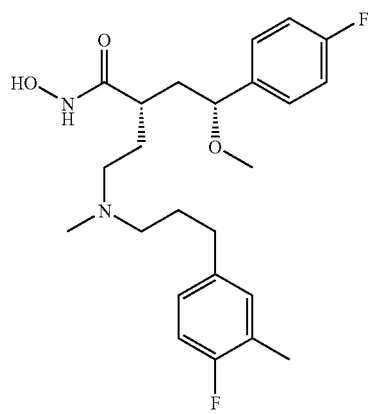

(2S,4R)-2-(2-((3-(4-fluoro-3-methylphenyl)propyl)(methyl)amino)ethyl)-4-(4-fluorophenyl)-N-hydroxy-4-methoxybutanamide (COMPOUND 167892) Prepared according to General Scheme 5.

¹H-NMR (CD₃OD): δ 7.29 (dd, 2H, J=5.5 and 8.6), 7.11-7.02 (m, 4H), 6.94 (t, 1H, J=9.0), 4.06 (dd, 1H, J=3.4 and 9.9), 3.49 (S, 1H), 3.18 (m, 4H), 3.07 (m, 2H), 2.83 (s, 3H), 2.65 (t, 2H, J=7.4), 2.55 (m, 1H), 2.23 (s, 3H), 2.03-1.77 (m, 7H); LC/MS: $t_R$=5.8 min. MS (API-ES) m/z 435 (M+H⁺).

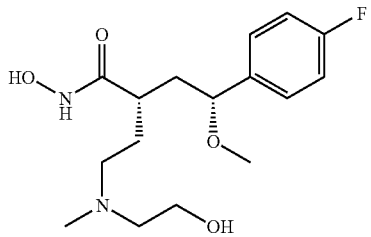

(2S,4R)-4-(4-fluorophenyl)-N-hydroxy-2-((2-hydroxyethyl)(methyl)amino)ethyl)-4-methoxybutanamide (COMPOUND 167922) Prepared according to General Scheme 5.

¹H-NMR (CD₃OD): δ 7.29 (dd, 2H, J=5.5 and 8.5), 7.09 (t, 2H, J=8.7), 4.04 (m, 2H), 3.83 (t, 2H, J=5.3), 3.74 (m, 1H), 3.49 (m, 1H), 3.25 (m, 2H), 3.18 (s, 3H), 2.87 (s, 3H), 2.57 (m, 1H), 2.15-1.84 (m, 4H); LC/MS: $t_R$=2.2 min. MS (API-ES) m/z 329 (M+H⁺).

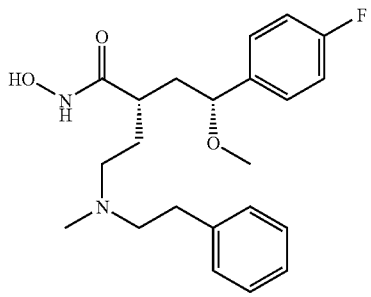

(2S,4R)-4-(4-fluorophenyl)-N-hydroxy-4-methoxy-2-(2-(methyl(phenethyl)amino)ethyl)butanamide (COMPOUND 167952) Prepared according to General Scheme 5.

¹H-NMR (CD₃OD): δ 7.37-7.26 (m, 7H), 7.08 (t, 2H, J=8.5), 4.06 (dd, 1H, J=6.6 and 7.5), 3.18 (m, 4H), 3.07-2.98 (m, 4H), 2.88 (s, 3H), 2.55 (m, 1H), 2.07-1.80 (m, 4H); LC/MS: $t_R$=5.0 min. MS (API-ES) m/z 389 (M+H⁺).

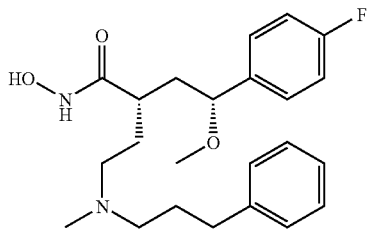

(2S,4R)-4-(4-fluorophenyl)-N-hydroxy-4-methoxy-2-(2-(methyl(3-phenylpropyl)amino)ethyl)butanamide (COMPOUND 167953) Prepared according to General Scheme 5.

¹H-NMR (CD₃OD): δ 7.32-7.18 (m, 7H), 7.08 (t, 2H, J=8.5), 4.04 (dd, 1H, J=4.3 and 9.3), 3.18 (m, 4H), 3.07 (m, 3H), 2.83 (d, 3H, J=3.2), 2.70 (t, 2H, J=7.4), 2.56 (m, 1H), 2.09-1.79 (m, 6H); LC/MS: $t_R$=5.2 min. MS (API-ES) m/z 403 (M+H⁺).

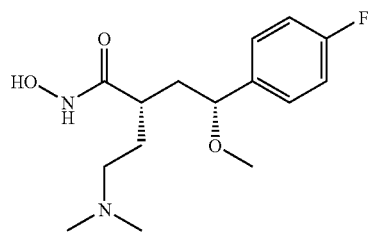

(2S,4R)-2-(2-(dimethylamino)ethyl)-4-(4-fluorophenyl)-N-hydroxy-4-methoxybutanamide (COMPOUND 167954) Prepared according to General Scheme 5.

¹H-NMR (CD₃OD): δ 7.29 (dd, 2H, J=5.5 and 8.6), 7.08 (t, 2H, J=8.8), 4.05 (dd, 1H, J=4.2 and 9.7), 3.20-3.10 (m, 4H), 2.98 (m, 1H), 2.87 (d, 6H, J=2.7), 2.57 (m, 1H), 2.02-1.80 (m, 4H); LC/MS: $t_R$=2.3 min. MS (API-ES) m/z 299 (M+H⁺).

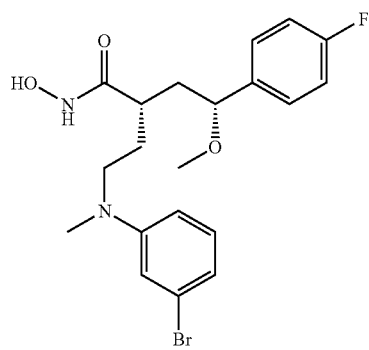

(2S,4R)-2-(2-((3-bromophenyl)(methyl)amino)ethyl)-4-(4-fluorophenyl)-N-hydroxy-4-methoxybutanamide (COMPOUND 168000) Prepared according to General Scheme 5.

¹H-NMR (CD₃OD): δ 7.27 (m, 2H), 7.08 (m, 3H), 6.86 (m, 1H), 6.79 (d, 1H, J=7.9), 6.70 (dd, 1H, J=1.4 and 8.7), 4.04 (dd, 1H, J=4.6 and 8.9), 3.24 (m, 2H), 3.17 (s, 3H), 2.91 (s, 3H), 2.48 (m, 1H), 1.86-1.56 (m, 4H); LC/MS: $t_R$=8.0 min. MS (API-ES) m/z 440 (M+H⁺).

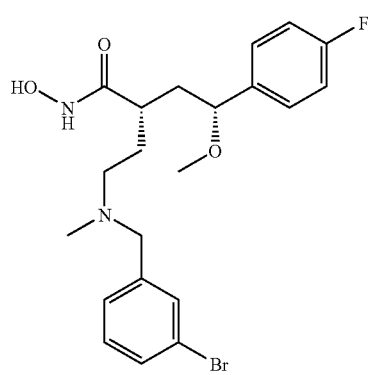

(2S,4R)-2-(2-((3-bromobenzyl)(methyl)amino)ethyl)-4-(4-fluorophenyl)-N-hydroxy-4-methoxybutanamide (COMPOUND 168001) Prepared according to General Scheme 5.

¹H-NMR (CD₃OD): δ 7.64 (m, 2H), 7.48 (m, 1H), 7.42 (m, 1H), 7.29 (m, 2H), 7.10 (t, 2H, J=8.8), 4.34 (m, 2H), 4.05 (m, 1H), 3.18 (m, 5H), 2.81 (s, 3H), 2.60 (m, 1H), 2.14-1.63 (m, 4H); LC/MS: $t_R$=5.2 min. MS (API-ES) m/z 454 (M+H⁺).

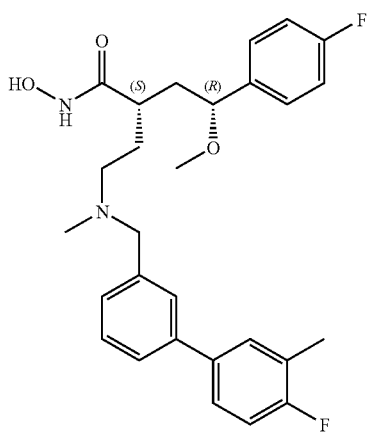

(2S,4R)-2-(2-(((4'-fluoro-3'-methylbiphenyl-3-yl)methyl)(methyl)amino)ethyl)-4-(4-fluorophenyl)-N-hydroxy-4-methoxybutanamide (COMPOUND 168003) Prepared according to General Scheme 5.

¹H-NMR (CD₃OD): δ 7.73 (s, 1H), 7.51 (m, 5H), 7.27 (m, 1H), 7.09 (m, 4H), 4.38 (s, 2H), 4.02 (m, 1H), 3.25 (m, 2H), 3.12 (s, 3H), 2.86 (s, 3H), 2.61 (m, 1H), 2.34 (s, 3H), 2.05-1.44 (m, 4H); LC/MS: t$_R$=6.5 min. MS (API-ES) m/z 483 (M+H⁺).

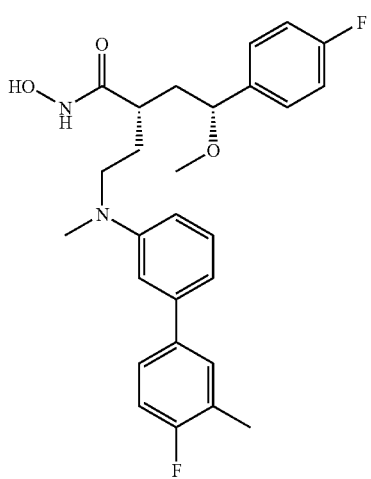

(2S,4R)-2-(2-((4'-fluoro-3'-methylbiphenyl-3-yl)(methyl)amino)ethyl)-4-(4-fluorophenyl)-N-hydroxy-4-methoxybutanamide (COMPOUND 168007) Prepared according to General Scheme. 5.

¹H-NMR (CD₃OD): δ 7.49 (m, 3H), 7.28 (m, 4H), 7.06 (m, 4H), 4.02 (dd, 1H, J=4.0 and 9.1), 3.49 (m, 2H), 3.14 (s, 3H), 2.54 (m, 1H), 2.32 (d, 3H, J=1.1), 1.93-1.63 (m, 4H); LC/MS: t$_R$=7.4 min. MS (API-ES) m/z 469 (M+H⁺).

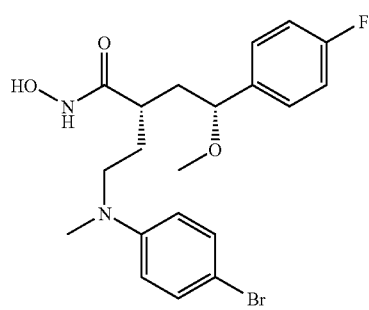

(2S,4R)-2-(2-((4-bromophenyl)(methyl)amino)ethyl)-4-(4-fluorophenyl)-N-hydroxy-4-methoxybutanamide (COMPOUND 168013) Prepared according to General Scheme 5.

¹H-NMR (CD₃OD): δ 7.33 (d, 2H, J=9.0), 7.27 (dd, 2H, J=6.1 and 8.0), 7.06 (t, 2H, J=8.8), 6.75 (d, 2H, J=8.8), 4.03 (dd, 1H, J=4.6 and 9.2), 3.37 (m, 2H), 3.16 (s, 3H), 2.94 (s, 3H), 2.49 (m, 1H), 1.87-1.55 (m, 4H); LC/MS: t$_R$=7.4 min. MS (API-ES) m/z 440 (M+H⁺).

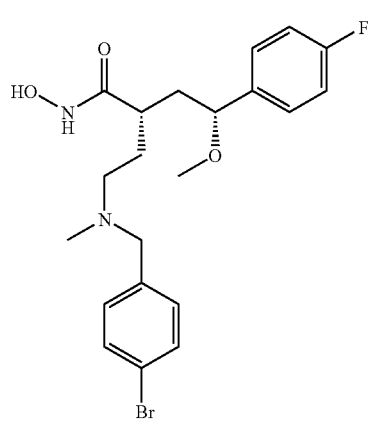

2S,4R)-2-(2-((4-bromobenzyl)(methyl)amino)ethyl)-4-(4-fluorophenyl)-N-hydroxy-4-methoxybutanamide (Compound 168015) Prepared according to General Scheme 5.

¹H-NMR (CD₃OD): δ 7.66 (d, 2H, J=8.4), 7.42 (d, 2H, J=8.4), 7.30 (dd, 2H, J=5.5 and 8.6), 7.09 (t, 2H, J=8.8), 4.30 (s, 2H), 4.22 (dd, 1H, J=3.6 and 9.5), 3.17 (m, 5H) 2.79 (m, 1H), 2.71 (m, 1H), 2.14-1.78 (m, 4H); LC/MS: t$_R$=5.2 min. MS (API-ES) m/z 454 (M+H⁺).

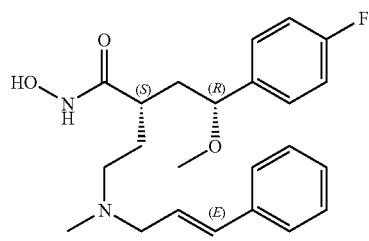

(2S,4R)-2-(2-(cinnamyl(methyl)amino)ethyl)-4-(4-fluorophenyl)-N-hydroxy-4-methoxybutanamide (COMPOUND 168017) Prepared according to General Scheme 5.

¹H-NMR (CD₃OD): δ 7.40 (d, 2H, J=7.5), 7.27 (m, 6H), 7.04 (t, 2H, J=8.7), 6.58 (d, 1H, J=16.2), 6.27 (m, 1H), 4.02 (dd, 1H, J=4.5 and 9.1), 3.22 (d, 2H, J=6.5), 3.16 (s, 3H), 2.50

(m, 3H), 2.29 (m, 3H), 1.89-1.58 (m, 4H); LC/MS: $t_R$=5.3 min. MS (API-ES) m/z 401 (M+H$^+$).

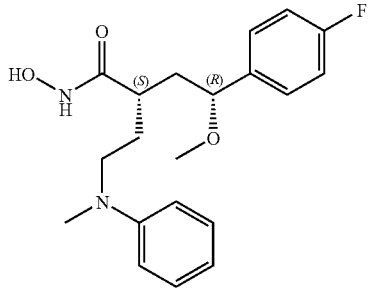

(2S,4R)-4-(4-fluorophenyl)-N-hydroxy-4-methoxy-2-(2-(methyl(phenyl)amino)ethyl)butanamide (COMPOUND 168028) Prepared according to General Scheme 5.

$^1$H-NMR (CD$_3$OD): δ 7.44 (m, 2H), 7.25 (m, 5H), 7.05 (t, 2H, J=8.8), 4.02 (dd, 1H, J=3.6 and 9.5), 3.47 (m, 2H), 3.15 (s, 3H), 3.14 (s, 3H), 2.52 (m, 1H), 1.87-1.54 (m, 4H); LC/MS: $t_R$=4.6 min. MS (API-ES) m/z 361 (M+H$^+$).

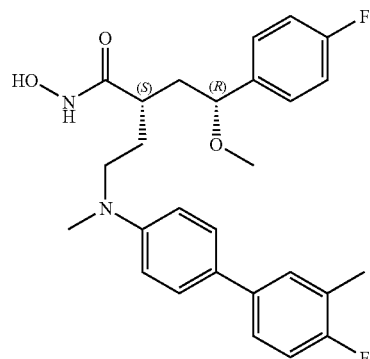

(2S,4R)-2-(2-((4'-fluoro-3'-methylbiphenyl-4-yl)(methyl) amino)ethyl)-4-(4-fluorophenyl)-N-hydroxy-4-methoxybutanamide (COMPOUND 168038) Prepared according to General Scheme 5.

$^1$H-NMR (CD$_3$OD): 7.52 (d, 2H, J=8.6), 7.41 (d, 1H, J=7.5), 7.34 (m, 1H), 7.05 (m, 5H), 4.04 (dd, 1H, J=4.2 and 9.3), 3.40 (t, 2H, J=7.7), 3.17 (s, 3H), 3.03 (s, 3H), 2.53 (m, 1H), 2.31 (s, 3H), 1.88-1.61 (m, 4H); LC/MS: $t_R$=7.7 min. MS (API-ES) m/z 469 (M+H$^+$).

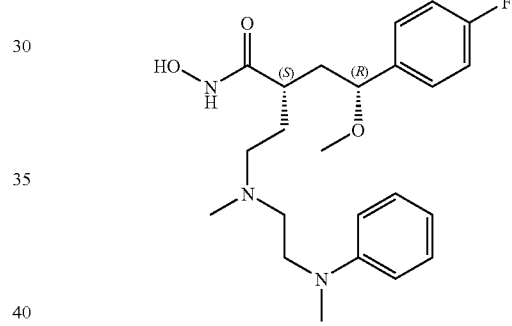

(2S,4R)-4-(4-fluorophenyl)-N-hydroxy-4-methoxy-2-(2-(methyl(2-(methyl(phenyl)amino)ethyl)amino)ethyl)butanamide (COMPOUND 168058) Prepared according to General Scheme 5.

$^1$H-NMR (CD$_3$OD): 7.24 (m, 4H), 7.08 (t, 2H, J=8.8), 6.87 (d, 2H, J=7.9), 6.78 (t, 1H, J=7.3), 4.04 (dd, 1H, J=3.9 and 9.5), 3.64 (t, 2H, J=6.7), 3.34 (m, 3H), 3.17 (s, 3H), 3.07 (m, 1H), 2.94 (s, 3H), 2.92 (s, 3H), 2.56 (m, 1H), 2.03-1.71 (m, 4H); LC/MS: $t_R$=5.2 min. MS (API-ES) m/z 418 (M+H$^+$).

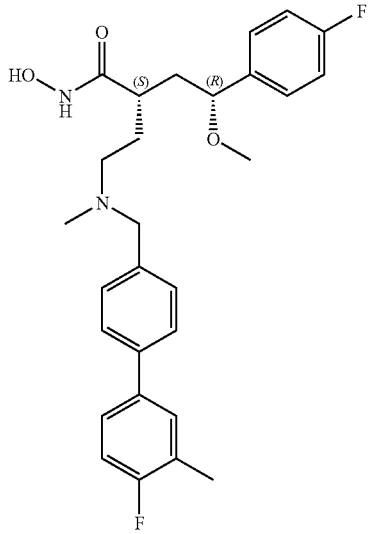

(2S,4R)-2-(2-(((4'-fluoro-3'-methylbiphenyl-4-yl)methyl) (methyl)amino)ethyl)-4-(4-fluorophenyl)-N-hydroxy-4-methoxybutanamide (COMPOUND 168037) Prepared according to General Scheme 5.

$^1$H-NMR (CD$_3$OD): δ 7.80-6.97 (m, 11H), 4.36 (s, 2H), 4.04 (m, 1H), 3.17 (m, 5H), 2.83 (s, 3H), 2.57 (m, 1H), 2.34 (s, 3H), 2.11-1.63 (m, 4H); LC/MS: $t_R$=6.6 min. MS (API-ES) m/z 483 (M+H$^+$).

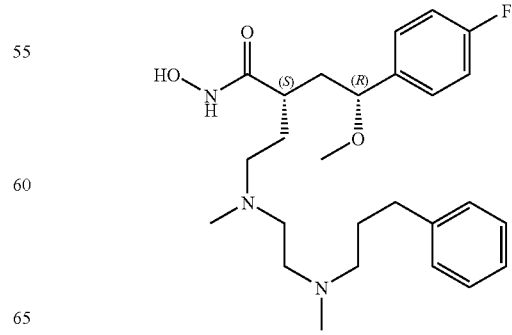

(2S,4R)-4-(4-fluorophenyl)-N-hydroxy-4-methoxy-2-(2-(methyl(2-(methyl(3-phenylpropyl)amino)ethyl)amino)ethyl)butanamide (COMPOUND 168082) Prepared according to General Scheme 5.

$^1$H-NMR (CD$_3$OD): 7.34-7.17 (m, 7H), 7.08 (t, 2H, J=8.7), 4.04 (dd, 1H, J=3.6 and 9.8), 3.17 (m, 7H), 2.92 (s, 3H), 2.85 (s, 3H), 2.72 (m, 4H), 2.60 (m, 3H), 2.06 (m, 3H), 1.81 (m, 3H); LC/MS: $t_R$=4.3 min. MS (API-ES) m/z 460 (M+H$^+$). Characterizing Data for Compounds in Table 7

(2S,4R)-4-(4-fluorophenyl)-N-hydroxy-2-(2-(3-(hydroxymethyl)piperidin-1-yl)ethyl)-4-methoxybutanamide (COMPOUND 167885) Prepared according to General Scheme 5.

$^1$H-NMR (CD$_3$OD): 7.29 (dd, 2H, J=5.2 and 8.5), 7.08 (t, 2H, J=8.8), 4.05 (dd, 1H, J=3.8 and 8.7), 3.54 (m, 3H), 3.42 (m, 1H), 3.26 (m, 1H), 3.18 (s, 3H), 2.98 (m, 1H), 2.83 (m, 1H), 2.68 (m, 1H), 2.57 (m, 1H), 2.07-1.67 (m, 9H); LC/MS: $t_R$=4.9 min. MS (API-ES) m/z 369 (M+H$^+$).

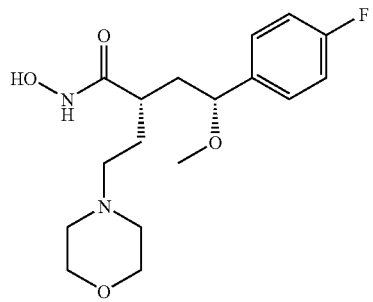

(2S,4R)-4-(4-fluorophenyl)-N-hydroxy-4-methoxy-2-(2-morpholinoethyl)butanamide (Compound 167829) Prepared according to General Scheme 5.

LC/MS: $t_R$=2.4 min. MS (API-ES) m/z 341 (M+H$^+$).

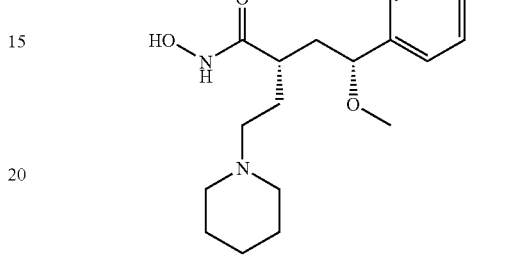

(2S,4R)-4-(4-fluorophenyl)-N-hydroxy-4-methoxy-2-(2-(piperidin-1-yl)ethyl)butanamide (COMPOUND 167889) Prepared according to General Scheme 5.

$^1$H-NMR (CD$_3$OD): 7.29 (dd, 2H, J=6.0 and 8.1), 7.08 (t, 2H, J=8.8), 4.05 (dd, 1H, J=3.9 and 9.7), 3.50 (d, 2H, J=13.3), 3.25 (m, 1H), 3.18 (s, 3H), 3.09 (m, 1H), 2.92 (m, 2H), 2.56 (m, 1H), 2.05-1.41 (m, 10H); LC/MS: $t_R$=3.0 min. MS (API-ES) m/z 339 (M+H$^+$).

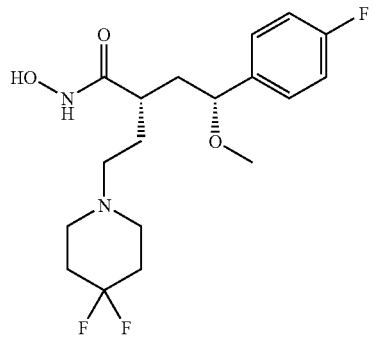

(2S,4R)-2-(2-(4,4-difluoropiperidin-1-yl)ethyl)-4-(4-fluorophenyl)-N-hydroxy-4-methoxybutanamide (COMPOUND 167884) Prepared according to General Scheme 5.

$^1$H-NMR (CD$_3$OD): 7.27 (dd, 2H, J=5.5 and 8.7), 7.06 (t, 2H, J=8.8), 4.03 (dd, 1H, J=3.8 and 9.7), 3.17 (s, 3H), 2.53 (t, 4H, J=5.4), 2.38 (dd, 2H, J=6.1 and 14.7), 1.97 (m, 4H), 1.77 (m, 2H), 1.59 (m, 1H), 1.29 (m, 1H); LC/MS: $t_R$=3.8 min. MS (API-ES) m/z 376 (M+H$^+$).

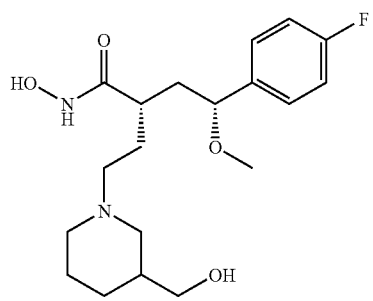

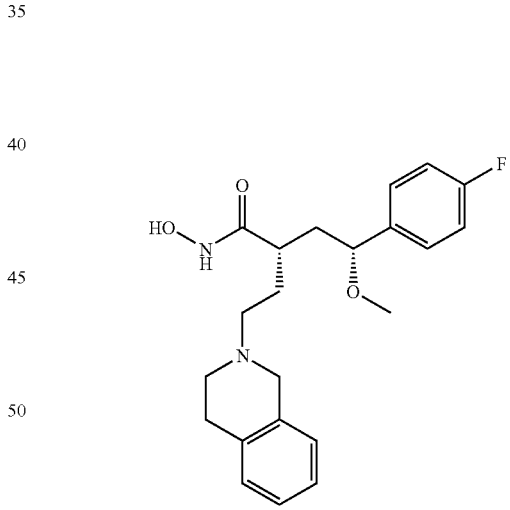

(2S,4R)-2-(2-(3,4-dihydroisoquinolin-2(1H)-yl)ethyl)-4-(4-fluorophenyl)-N-hydroxy-4-methoxybutanamide (COMPOUND 167891) Prepared according to General Scheme 5.

$^1$H-NMR (CD$_3$OD): δ 7.33-7.14 (m, 6H), 7.09 (t, 2H, J=8.8), 4.58 (d, 1H, J=16.2), 4.31 (dd, 1H, J=5.8 and 15.3), 4.06 (dd, 1H, J=4.0 and 9.3), 3.80 (m, 1H), 3.25 (m, 2H), 3.19 (m, 4H), 2.61 (m, 1H), 2.15-1.88 (m, 4H); LC/MS: $t_R$=4.5 min. MS (API-ES) m/z 387 (M+H$^+$).

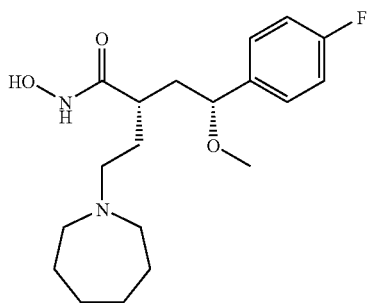

(2S,4R)-2-(2-(azepan-1-yl)ethyl)-4-(4-fluorophenyl)-N-hydroxy-4-methoxybutanamide (COMPOUND 167911) Prepared according to General Scheme 5.

$^1$H-NMR (CD$_3$OD): δ 7.32 (dd, 2H, J=5.5 and 8.5), 7.08 (t, 2H, J=8.7), 4.15 (dd, 1H, J=4.1 and 9.6), 3.57 (t, 2H, J=6.4), 3.35 (m, 2H), 3.15 (m, 5H), 2.40 (m, 1H), 1.95-1.60 (m, 12H); LC/MS: t$_R$=4.8 min. MS (API-ES) m/z 353 (M+H$^+$).

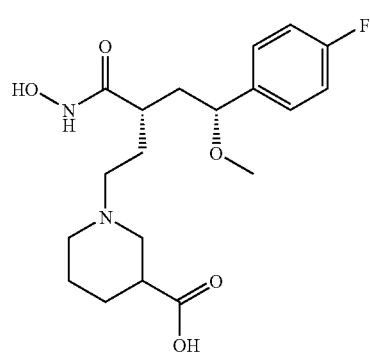

1-((3S,5R)-5-(4-fluorophenyl)-3-(hydroxycarbamoyl)-5-methoxypentyl)piperidine-3-carboxylic acid (COMPOUND 167924) Prepared according to General Scheme 5.

$^1$H-NMR (CD$_3$OD): δ 7.26 (dd, 2H, J=5.9 and 8.7), 7.05 (t, 2H, J=8.8), 4.02 (dd, 1H, J=3.7 and 9.2), 3.71 (m, 1H), 3.50 (m, 1H), 3.15 (m, 4H), 2.99 (m, 3H), 2.54 (m, 1H), 2.17 (m, 1H), 2.05-1.70 (m, 8H); LC/MS: t$_R$=2.9 min. MS (API-ES) m/z 383 (M+H$^+$).

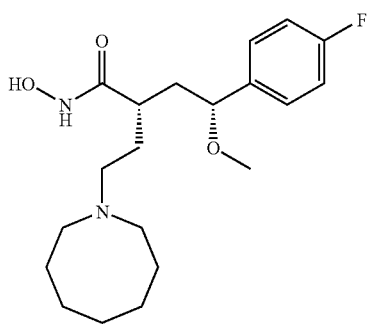

(2S,4R)-2-(2-(azocan-1-yl)ethyl)-4-(4-fluorophenyl)-N-hydroxy-4-methoxybutanamide (COMPOUND 167912) Prepared according to General Scheme 5.

LC/MS: t$_R$=4.9 min. MS (API-ES) m/z 367(M+H$^+$).

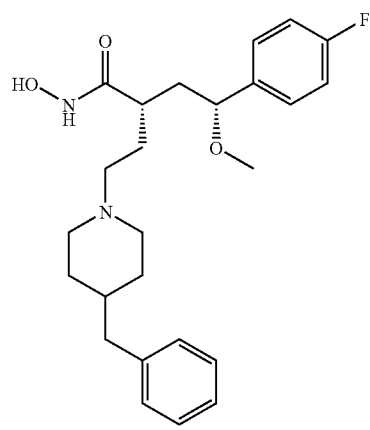

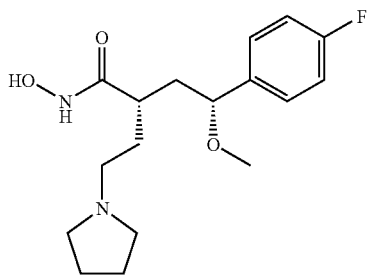

(2S,4R)-4-(4-fluorophenyl)-N-hydroxy-4-methoxy-2-(2-(pyrrolidin-1-yl)ethyl)butanamide (COMPOUND 167923) Prepared according to General Scheme 5.

$^1$H-NMR (CD$_3$OD): δ 7.29 (dd, 2H, J=5.5 and 8.6), 7.09 (t, 2H, J=8.8), 4.05 (dd, 1H, J=4.2 and 9.6), 3.63 (m, 2H), 3.25 (m, 2H), 3.24 (s, 3H), 3.07 (m, 2H), 2.57 (m, 1H), 2.15 (m, 2H), 2.03-1.79 (m, 6H); LC/MS: t$_R$=2.8 min. MS (API-ES) m/z 325 (M+H$^+$).

(2S,4R)-2-(2-(4-benzylpiperidin-1-yl)ethyl)-4-(4-fluorophenyl)-N-hydroxy-4-methoxybutanamide (COMPOUND 167940) Prepared according to General Scheme 5.

$^1$H-NMR (CD$_3$OD): δ 7.28 (m, 4H), 7.19 (m, 4H), 7.07 (t, 2H, J=8.8), 4.03 (dd, 1H, J=3.8 and 9.5), 3.52 (dd, 2H, J=1.3 and 11.3), 3.17 (s, 3H), 3.07 (m, 1H), 2.99-2.82 (m, 3H), 2.61-2.50 (m, 3H), 1.98-1.78 (m, 6H), 1.44 (dd, 2H, J=13.2 and 27.5); LC/MS: t$_R$=5.6 min. MS (API-ES) m/z 429 (M+H$^+$).

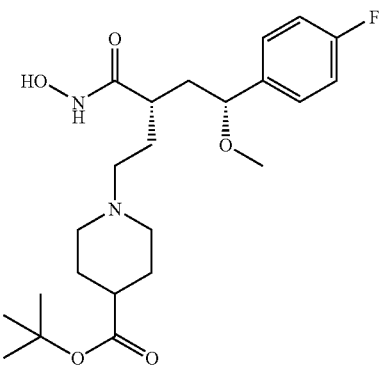

tert-butyl 4-((3S,5R)-5-(4-fluorophenyl)-3-(hydroxycarbamoyl)-5-methoxypentyl)piperazine-1-carboxylate (COMPOUND 167944) Prepared according to General Scheme 5.
$^1$H-NMR (CD$_3$OD): δ 7.28 (dd, 2H, J=5.4 and 8.4), 7.06 (t, 2H, J=8.5), 4.05 (dd, 1H, J=4.1 and 9.1), 3.57-3.37 (m, 6H), 3.17 (s, 3H), 2.38 (m, 4H), 1.93-1.56 (m, 4H), 1.45 (s, 9H); LC/MS: $t_R$=4.8 min. MS (API-ES) m/z 340 (M+H$^+$).

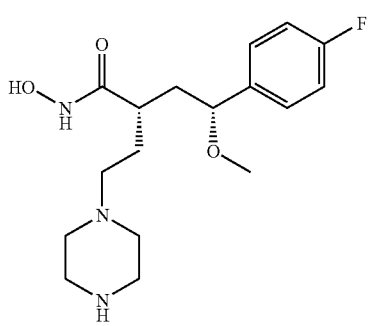

(2S,4R)-4-(4-fluorophenyl)-N-hydroxy-4-methoxy-2-(2-(piperazin-1-yl)ethyl)butanamide (COMPOUND 167955) Prepared according to General Scheme 5.
$^1$H-NMR (CD$_3$OD): δ 7.27 (dd, 2H, J=5.4 and 8.4), 7.07 (t, 2H, J=8.8), 4.04 (dd, 1H, J=4.0 and 9.1), 3.18 (s, 3H), 2.81 (m, 4H), 2.57 (m, 3H), 1.93-1.56 (m, 4H); LC/MS: $t_R$=1.5 min. MS (API-ES) m/z 340 (M+H$^+$).

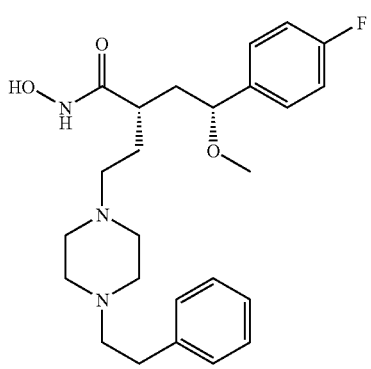

(2S,4R)-4-(4-fluorophenyl)-N-hydroxy-4-methoxy-2-(2-(4-phenethylpiperazin-1-yl)ethyl)butanamide (COMPOUND 167958) Prepared according to General Scheme 5.
$^1$H-NMR (CD$_3$OD): δ 7.28 (m, 7H), 7.07 (t, 2H, J=9.0), 4.04 (dd, 1H, J=4.2 and 9.8), 3.25 (m, 1H), 3.18 (s, 6H), 3.08 (m, 1H), 2.98 (m, 3H), 2.66 (m, 2H), 2.52 (m, 1H), 2.01-1.55 (m, 4H); LC/MS: $t_R$=4.1 min. MS (API-ES) m/z 444 (M+H$^+$).

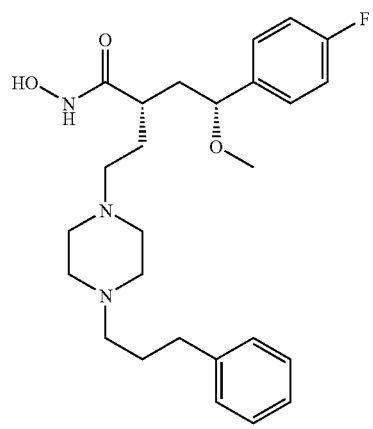

(2S,4R)-4-(4-fluorophenyl)-N-hydroxy-4-methoxy-2-(2-(4-(3-phenylpropyl)piperazin-1-yl)ethyl)butanamide (COMPOUND 167959) Prepared according to General Scheme 5.
$^1$H-NMR (CD$_3$OD): δ 7.25 (m, 7H), 7.05 (t, 2H, J=8.8), 4.02 (dd, 1H, J=4.2 and 9.8), 3.16 (m, 4H), 2.99 (m, 4H), 2.68 (m, 3H), 2.54 (m, 4H), 2.06-1.48 (m, 4H); LC/MS: $t_R$=4.4 min. MS (API-ES) m/z 458 (M+H$^+$).

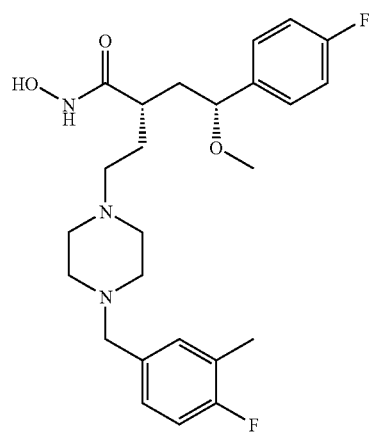

(2S,4R)-2-(2-(4-(4-fluoro-3-methylbenzyl)piperazin-1-yl)ethyl)-4-(4-fluorophenyl)-N-hydroxy-4-methoxybutanamide (COMPOUND 167960) Prepared according to General Scheme 5.
$^1$H-NMR (CD$_3$OD): δ 7.27 (m, 4H), 7.07 (m, 3H), 4.03 (dd, 1H, J=4.2 and 9.8), 3.86 (s, 2H), 3.17 (s, 3H), 3.13-2.77 (m, 9H), 2.52 (m, 1H), 2.27 (s, 3H), 2.02-1.62 (m, 4H); LC/MS: $t_R$=4.6 min. MS (API-ES) m/z 462 (M+H$^+$).

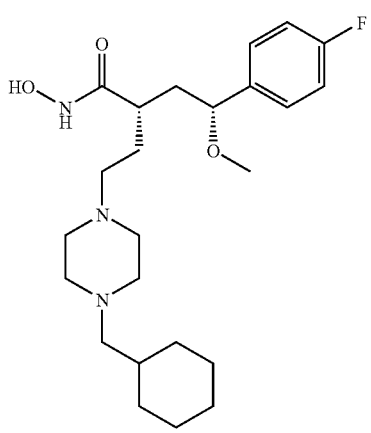

(2S,4R)-2-(2-(4-(cyclohexylmethyl)piperazin-1-yl)ethyl)-4-(4-fluorophenyl)-N-hydroxy-4-methoxybutanamide (COMPOUND 167961) Prepared according to General Scheme 5.

$^1$H-NMR (CD$_3$OD): δ 7.25 (dd, 2H, J=5.5 and 8.5), 7.04 (t, 2H, J=8.6), 4.02 (dd, 1H, J=4.1 and 9.7), 3.16 (m, 5H), 3.05-2.64 (m, 10H), 2.49 (m, 1H), 1.95-1.54 (m, 12H), 1.47-0.99 (m, 3H); LC/MS: $t_R$=4.0 min. MS (API-ES) m/z 436 (M+H$^+$).

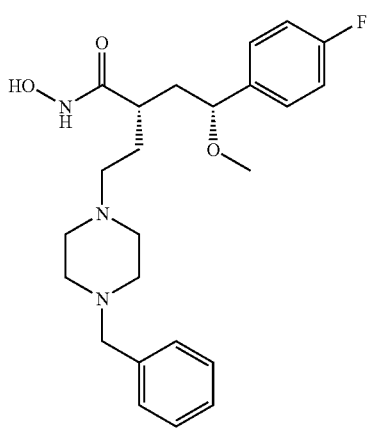

(2S,4R)-2-(2-(4-benzylpiperazin-1-yl)ethyl)-4-(4-fluorophenyl)-N-hydroxy-4-methoxybutanamide (COMPOUND 167962) Prepared according to General Scheme 5.

$^1$H-NMR (CD$_3$OD): δ 7.38 (s, 5H), 7.25 (dd, 2H, J=5.4 and 8.6), 7.05 (t, 2H, J=8.8), 4.02 (dd, 1H, J=4.1 and 9.7), 3.92 (s, 2H), 3.15 (s, 3H), 3.05-2.64 (m, 10H), 2.49 (m, 1H), 1.96-1.61 (m, 4H); LC/MS: $t_R$=3.8 min. MS (API-ES) m/z 430 (M+H$^+$).

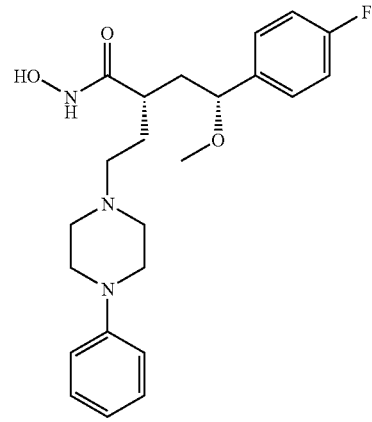

(2S,4R)-4-(4-fluorophenyl)-N-hydroxy-4-methoxy-2-(2-(4-phenylpiperazin-1-yl)ethyl)butanamide (COMPOUND 167986) Prepared according to General Scheme 5.

LC/MS: $t_R$=4.9 min. MS (API-ES) m/z 416 (M+H$^+$).

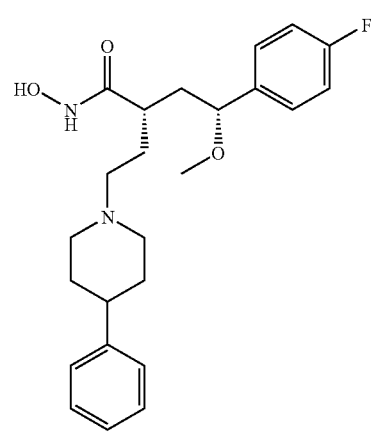

(2S,4R)-4-(4-fluorophenyl)-N-hydroxy-4-methoxy-2-(2-(4-phenylpiperidin-1-yl)ethyl)butanamide (COMPOUND 167987) Prepared according to General Scheme 5.

LC/MS: $t_R$=5.2 min. MS (API-ES) m/z 415 (M+H$^+$).

$^1$H-NMR (CD$_3$OD): 7.52 (d, 2H, J=8.6), 7.41 (d, 1H, J=7.5), 7.34 (m, 1H), 7.05 (m, 5H), 4.04 (dd, 1H, J=4.2 and 9.3), 3.40 (t, 2H, J=7.7), 3.17 (s, 3H), 3.03 (s, 3H), 2.53 (m, 1H), 2.31 (s, 3H), 1.88-1.61 (m, 4H); LC/MS: $t_R$=7.7 min. MS (API-ES) m/z 469 (M+H$^+$).

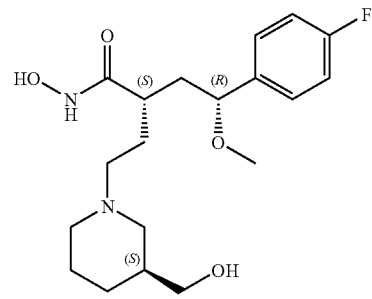

(2S,4R)-4-(4-fluorophenyl)-N-hydroxy-2-(2-((S)-3-(hydroxymethyl)piperidin-1-yl)ethyl)-4-methoxybutanamide (COMPOUND 168039) Prepared according to General Scheme 5.

¹H-NMR (CD₃OD): 7.29 (dd, 2H, J=5.4 and 8.6), 7.08 (t, 2H, J=8.8), 4.05 (dd, 1H, J=3.9 and 9.5), 3.54 (m, 3H), 3.42 (m, 1H), 3.18 (m, 4H), 2.99 (m, 1H), 2.82 (t, 1H, J=11.3), 2.69 (t, 1H, J=12.0), 2.57 (m, 1H), 2.07-1.69 (m, 8H), 1.28 (m, 1H); LC/MS: t$_R$=2.7 min. MS (API-ES) m/z 369 (M+H⁺).

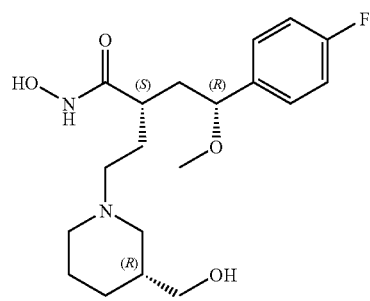

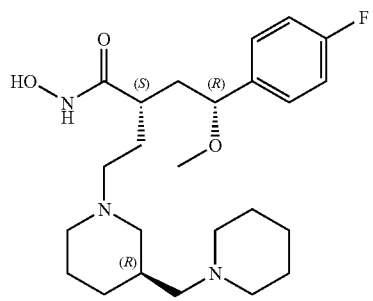

(2S,4R)-4-(4-fluorophenyl)-N-hydroxy-4-methoxy-2-(2-((R)-3-(piperidin-1-ylmethyl)piperidin-1-yl)ethyl)butanamide (COMPOUND 168044) Prepared according to General Scheme 5.

¹H-NMR (CD₃OD): 7.28 (dd, 2H, J=5.5 and 8.5), 7.07 (t, 2H, J=8.6), 4.05 (dd, 1H, J=3.9 and 9.5), 3.57 (m, 3H), 3.37 (m, 1H), 3.18 (m, 6H), 3.07-2.82 (m, 5H), 2.60 (m, 1H), 2.38 (m, 1H), 2.10-1.68 (m, 15H); LC/MS: t$_R$=2.1 min. MS (API-ES) m/z 436 (M+H⁺).

(2S,4R)-4-(4-fluorophenyl)-N-hydroxy-2-(2-((R)-3-(hydroxymethyl)piperidin-1-yl)ethyl)-4-methoxybutanamide (COMPOUND 168059) Prepared according to General Scheme 5.

¹H-NMR (CD₃OD): 7.29 (dd, 2H, J=5.4 and 8.6), 7.08 (t, 2H, J=8.8), 4.05 (dd, 1H, J=3.9 and 9.5), 3.54 (m, 3H), 3.42 (m, 1H), 3.18 (m, 4H), 2.99 (m, 1H), 2.82 (t, 1H, J=11.3), 2.69 (t, 1H, J=12.0), 2.57 (m, 1H), 2.07-1.69 (m, 8H), 1.28 (m, 1H); LC/MS: t$_R$=1.6 min. MS (API-ES) m/z 369 (M+H⁺).

Characterizing Data for Compounds in Table 8

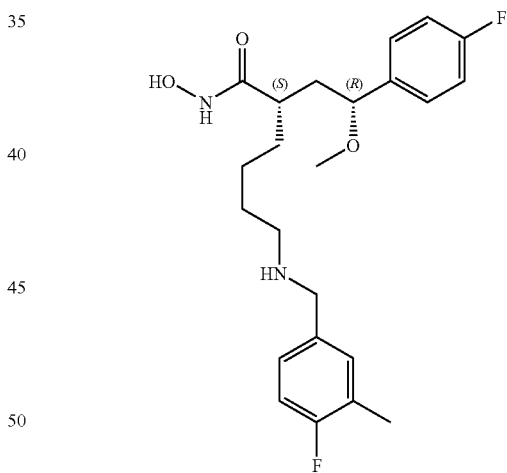

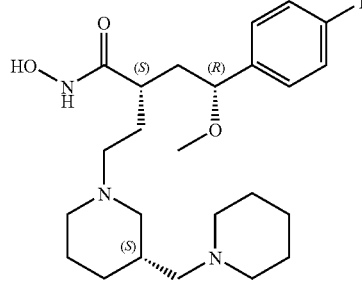

(2S,4R)-4-(4-fluorophenyl)-N-hydroxy-4-methoxy-2-(2-((S)-3-(piperidin-1-ylmethyl)piperidin-1-yl)ethyl)butanamide (COMPOUND 168045) Prepared according to General Scheme 5.

¹H-NMR (CD₃OD): 7.28 (dd, 2H, J=5.5 and 8.5), 7.07 (t, 2H, J=8.6), 4.05 (dd, 1H, J=3.9 and 9.5), 3.57 (m, 3H), 3.37 (m, 1H), 3.18 (m, 6H), 3.07-2.82 (m, 5H), 2.60 (m, 1H), 2.38 (m, 1H), 2.10-1.68 (m, 15H); LC/MS: t$_R$=2.1 min. MS (API-ES) m/z 436 (M+H⁺).

(S)-6-(4-fluoro-3-methylbenzylamino)-2-((R)-2-(4-fluorophenyl)-2-methoxyethyl)-N-hydroxyhexanamide (COMPOUND 168136) Prepared according to General Scheme 7.

¹H-NMR (CD₃OD): 7.30 (m, 4H), 7.10 (m, 3H), 4.12 (s, 2H), 4.03 (dd, 1H, J=3.7 and 9.7), 3.17 (s, 3H), 3.00 (t, 1H, J=8.0), 2.47 (m, 1H), 1.80-1.25 (m, 8H); LC/MS: t$_R$=4.7 min. MS (API-ES) m/z 421 (M+H⁺).

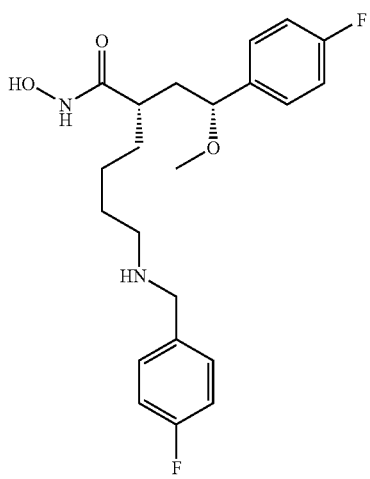

(S)-6-(4-fluorobenzylamino)-2-((R)-2-(4-fluorophenyl)-2-methoxyethyl)-N-hydroxyhexanamide (COMPOUND 168137) Prepared according to General Scheme 7.

$^1$H-NMR (CD$_3$OD): 7.50 (dd, 2H, J=5.3 and 8.5), 7.27 (dd, 2H, J=5.5 and 8.5), 7.19 (t, 2H, J=8.7), 7.07 (t, 2H, J=8.9), 4.16 (s, 2H), 4.03 (dd, 1H, J=3.7 and 9.8), 3.17 (s, 3H), 3.01 (t, 2H, J=8.1), 2.48 (m, 1H), 1.79-1.29 (m, 8H); LC/MS: t$_R$=4.3 min. MS (API-ES) m/z 407 (M+H$^+$).

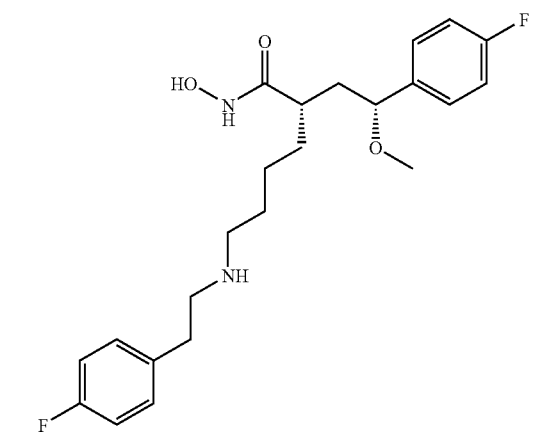

S)-6-(4-fluorophenethylamino)-2-((R)-2-(4-fluorophenyl)-2-methoxyethyl)-N-hydroxyhexanamide (PT-168221) Prepared according to General Scheme 7.

1H NMR (CD$_3$OD): δ 7.28 (m, 4H), 7.07 (m, 4H), 4.03 (dd, 1H, J=5.4 and 9.5), 3.23-3.14 (m, 5H), 2.98 (m, 4H), 2.47 (m, 1H) 1.84-1.31 (m, 8H); LC/MS: t$_R$=4.3 min. MS (API-ES) m/z 421 (M+H$^+$).

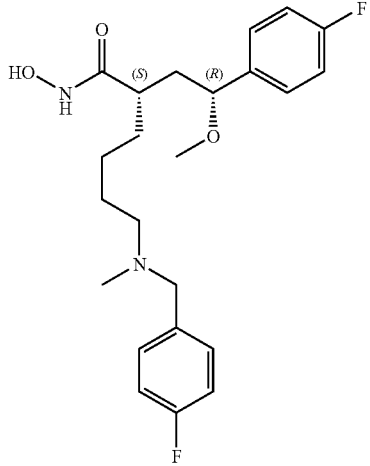

(S)-6-(4-fluorobenzyl)(methyl)amino)-2-((R)-2-(4-fluorophenyl)-2-methoxyethyl)-N-hydroxyhexanamide (COMPOUND 168138) Prepared according to General Scheme 7.

$^1$H-NMR (CD$_3$OD): 7.49 (dd, 2H, J=5.1 and 8.7); 7.24 (m, 4H), 7.03 (t, 2H, J=8.7), 4.38 (d, 1H, J=2.6), 4.17 (d, 1H, J=13.9), 3.99 (dd, 1H, J=3.8 and 9.4), 3.14 (s, 3H), 3.09 (m, 1H), 3.04 (m, 1H), 2.74 (s, 3H), 2.44 (m, 1H), 1.84-1.24 (m, 8H); LC/MS: t$_R$=4.5 min. MS (API-ES) m/z 421 (M+H$^+$).

(S)-2-((R)-2-(4-fluorophenyl)-2-methoxyethyl)-6-(3-(4-fluorophenyl)propylamino)-N-hydroxyhexanamide (PT-167222) Prepared according to General Scheme 7.

1H NMR (CD$_3$OD): δ 7.27 (m, 4H), 7.06 (m, 4H), 4.03 (dd, 1H, J=5.5 and 9.5), 3.17 (s, 3H), 2.96 (m, 4H), 2.70 (t, 2H, J=7.5), 2.47 (m, 1H), 1.95 (t, 2H, J=7.2), 1.84-1.25 (m, 8H); LC/MS: t$_R$=4.6 min. MS (API-ES) m/z 435 (M+H$^+$).

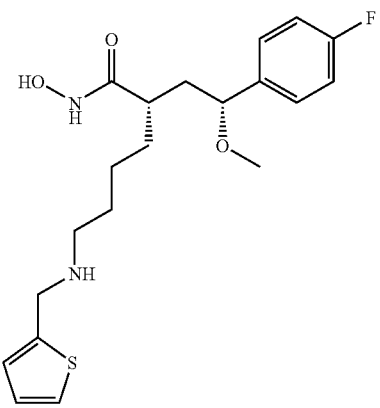

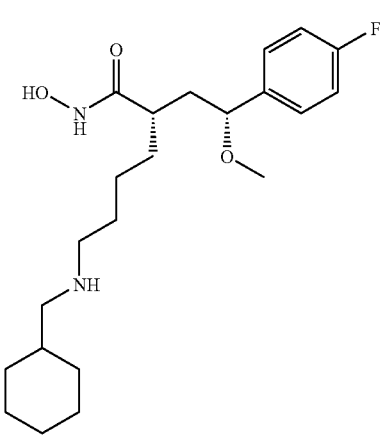

S)-2-((R)-2-(4-fluorophenyl)-2-methoxyethyl)-N-hydroxy-6-(thiophen-2-ylmethylamino)hexanamide (PT-168223) Prepared according to General Scheme 7.

1H NMR (CD$_3$OD): δ 7.57 (s, 1H), 7.28 (m, 3H), 7.09 (m, 3H), 4.42 (s, 2H), 4.03 (dd, 1H, J=5.3 and 9.4), 3.17 (s, 3H), 3.01 (m, 2H), 2.47 (m, 1H), 1.87-1.28 (m, 8H); LC/MS: t$_R$=3.9 min. MS (API-ES) m/z 395 (M+H$^+$).

(S)-6-(cyclohexylmethylamino)-2-((R)-2-(4-fluorophenyl)-2-methoxyethyl)-N-hydroxyhexanamide (PT-168227) Prepared according to General Scheme 7.

1H NMR (CD$_3$OD): δ 7.27 (dd, 2H, J=5.5 and 8.5), 7.07 (t, 2H, J=8.9), 4.03 (dd, 1H, J=4.5 and 9.6), 3.17 (s, 3H), 2.94 (t, 2H, J=7.5), 2.82 (d, 2H, J=6.3), 2.47 (m, 1H), 1.88-1.53 (m, 12H), 1.49-1.08 (m, 7H); LC/MS: t$_R$=4.3 min. MS (API-ES) m/z 395 (M+H$^+$).

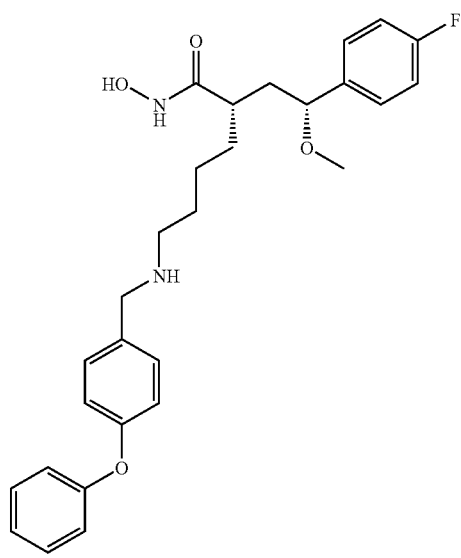

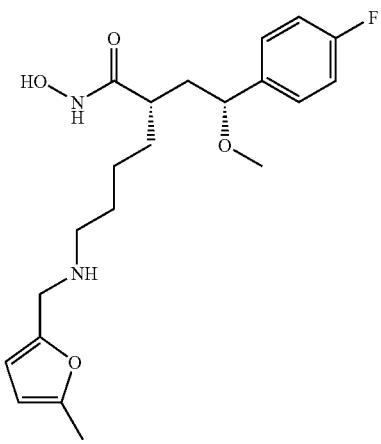

(S)-2-((R)-2-(4-fluorophenyl)-2-methoxyethyl)-N-hydroxy-6-(4-phenoxybenzylamino)hexanamide (PT-168224) Prepared according to General Scheme 7.

1H NMR (CD$_3$OD): δ 7.43 (m, 4H), 7.28 (m, 2H), 7.16 (m, 1H), 7.03 (m, 6H), 4.15 (s, 2H), 4.04 (dd, 1H, J=5.4 and 9.5), 3.17 (s, 3H), 3.00 (t, 2H, J=8.0), 2.48 (m, 1H), 1.79-1.25 (m, 8H); LC/MS: t$_R$=4.8 min. MS (API-ES) m/z 481 (M+H$^+$).

(S)-2-((R)-2-(4-fluorophenyl)-2-methoxyethyl)-N-hydroxy-6-((5-methylfuran-2-yl)methylamino)hexanamide (PT-168228) Prepared according to General Scheme 7.

LC/MS: t$_R$=4.0 min. MS (API-ES) m/z 393 (M+H$^+$).

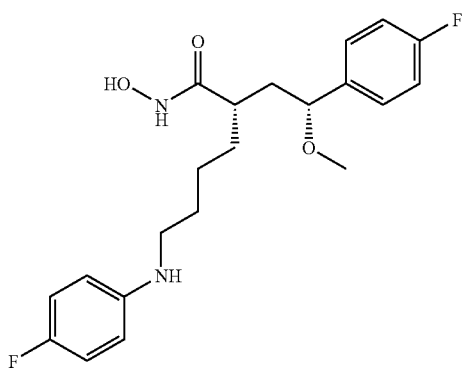
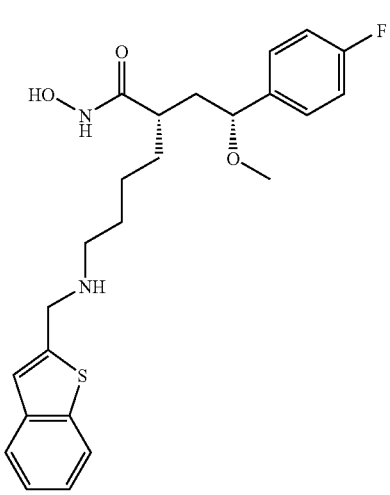

S)-2-((R)-2-(4-fluorophenyl)-2-methoxyethyl)-6-(4-fluorophenylamino)-N-hydroxyhexanamide (PT-168229) Prepared according to General Scheme 7.

1H NMR (CD$_3$OD): δ 7.39-7.21 (m, 6H), 7.06 (t, 2H, J=8.8), 4.02 (dd, 1H, J=3.2 and 9.5), 3.22 (m, 2H), 3.17 (s, 3H), 2.46 (m, 1H), 1.79-1.33 (m, 8H); LC/MS: t$_R$=4.5 min. MS (API-ES) m/z 393 (M+H$^+$).

(S)-6-(benzo[b]thiophen-2-ylmethylamino)-2-((R)-2-(4-fluorophenyl)-2-methoxyethyl)-N-hydroxyhexanamide (PT-168231) Prepared according to General Scheme 7.

1H NMR (CD$_3$OD): δ 7.89 (m, 2H), 7.54 (s, 1H), 7.42 (m, 2H), 7.27 (m, 2H), 7.07 (m, 2H), 4.52 (s, 2H), 4.01 (m, 1H), 3.17 (s, 3H), 3.07 (m, 2H), 2.47 (m, 1H), 1.88-1.26 (m, 8H); LC/MS: t$_R$=4.5 min. MS (API-ES) m/z 445 (M+H$^+$).

Characterizing Data for Compounds in Table 9

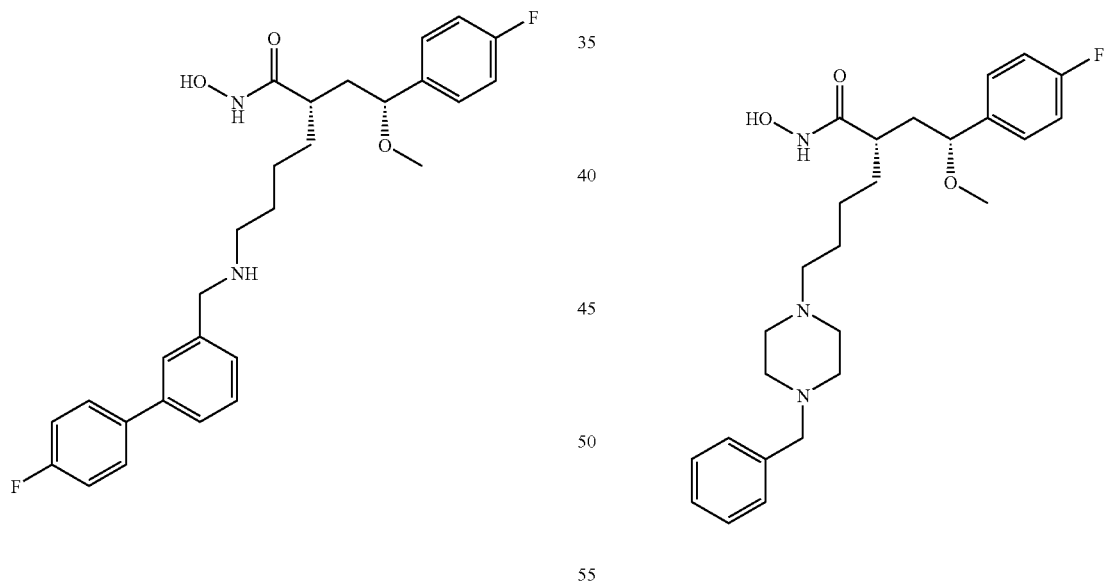

(S)-6-((4'-fluorobiphenyl-3-yl)methylamino)-2-((R)-2-(4-fluorophenyl)-2-methoxyethyl)-N-hydroxyhexanamide (PT-168230) Prepared according to General Scheme 7.

1H NMR (CD$_3$OD): δ 7.68 (m, 4H), 7.52 (m, 2H), 7.25 (m, 4H), 7.04 (t, 2H, J=8.6), 4.25 (s, 2H), 4.01 (m, 1H), 3.17 (s, 3H), 3.04 (t, 2H, J=7.4), 2.48 (m, 1H), 1.79-1.26 (m, 8H); LC/MS: t$_R$=4.9 min. MS (API-ES) m/z 482 (M+H$^+$).

(S)-6-(4-benzylpiperazin-1-yl)-2-((R)-2-(4-fluorophenyl)-2-methoxyethyl)-N-hydroxyhexanamide (PT-168226) Prepared according to General Scheme 7.

1H NMR (CD$_3$OD): δ 7.30 (m, 3H), 7.09 (m, 4H), 6.92 (m, 2H), 4.06 (m, 1H), 3.76 (m, 2H), 3.62 (m, 2H), 3.17 (m, 7H), 2.97 (m, 4H), 2.49 (m, 1H), 1.84-1.29 (m, 8H); LC/MS: t$_R$=4.5 min. MS (API-ES) m/z 458 (M+H$^+$).

What is claimed is:

1. A compound of the formula

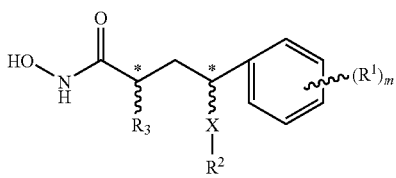

where
X is O or S;
R$^1$ is independently F, Cl, Br, I, alkyl of 1-3 carbons, or;
m is an integer having the value of 1 to 3;
R$^2$ is H or alkyl of 1 to 3 carbons,
R$^3$ is (CH$_2$)$_n$NR$^5$R$^6$;
n is an integer having the value of 1 to 6;
R$^5$ is H, alkyl of 1 to 6 carbons, phenyl where the phenyl is substituted with 0-3 R$^1$ groups, (CH$_2$)$_p$phenyl where the phenyl is substituted with 0-3 R$^1$ groups,
or R$^5$ is (CH$_2$)$_p$—N(C$_{1-3}$alkyl)phenyl,
p is an integer having the values 1 to 4;
R$^6$ is H, alkyl of 1 to 6 carbons, phenyl optionally substituted with 0-3 R$^1$ groups or with an —OPh group, or (CH$_2$)$_p$phenyl where the phenyl is substituted with 1-3 R$^1$ groups;
the asterisk indicates a carbon which is asymmetric or may be asymmetric, the wavy line represents a bond which can be of either R or S configuration, or
a pharmaceutically acceptable salt of said compound.

2. A compound in accordance with claim 1 where X is O.

3. A compound in accordance with claim 2 where R$^1$ is selected independently from the group consisting of F, Cl, and methyl.

4. A compound in accordance with claim 2 where m is an integer having the value of 1 or 2.

5. A compound in accordance with claim 1 where m is 1 and R$^1$ is F in the 4 (para) position to the side chain of the phenyl moiety.

6. A compound in accordance with claim 1 where m is 2, one R$^1$ group is in the 3 (meta) position on the phenyl ring relative to the side chain of the phenyl group, and the other R$^1$ group is in the 4 (para) position of the phenyl ring relative to the side chain of the phenyl group.

7. A compound in accordance with claim 2 where R$^3$ is (CH$_2$)$_n$NHR$^5$ or (CH$_2$)$_n$NR$^5$R$^6$.

8. A compound in accordance with claim 1 where X is S.

9. A compound of the formula

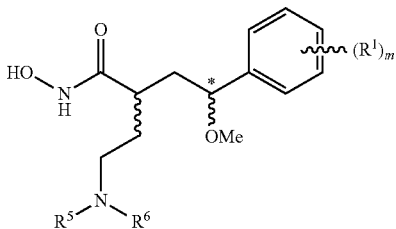

wherein R$^1$ is independently F, Cl, Br, I, alkyl of 1-3 carbons, or phenyl;
m is an integer having the value of 1 to 3;
R$^5$ is alkyl of 1 to 4 carbons, or phenyl substituted with 0 to 3 R$^1$ groups or R$^5$ is alkylphenyl where the alkyl group has 1 to 3 carbons and the phenyl group is substituted with 0 to 3 R$^1$ groups;

R$^6$ is alkyl of 1 to 4 carbons or alkylphenyl where the alkyl group has 1 to 4 carbons and the phenyl group is substituted with 1 to 3 R$^1$ groups;
the asterisk indicates a carbon which is asymmetric or may be asymmetric, the wavy line represents a bond which can be of either R or S configuration, or
a pharmaceutically acceptable salt of said compound.

10. A compound in accordance with claim 9 where the variable (R$^1$)$_m$ in the structural formula of the compound represents a fluoro atom in the 4 (para) position of the phenyl ring relative to its side chain.

11. A compound in accordance with claim 10 having the formula

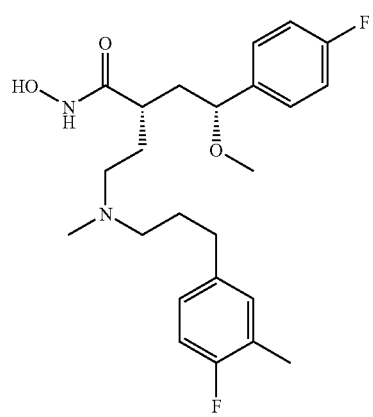

or a pharmaceutically acceptable salt of said compound.

12. A compound of the formula

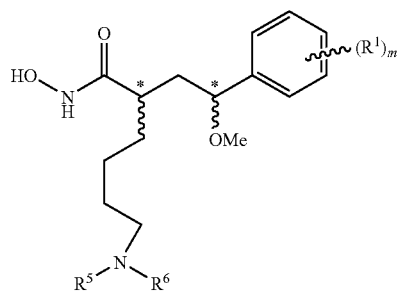

where R$^1$ is independently F, Cl, Br, I, alkyl of 1-3 carbons, or phenyl;
m is an integer having the value of 1 to 3;

R⁵ is selected from the group consisting of

[structure: cyclohexylmethyl]

[structure: 4-fluorophenyl]

[structure: 4-fluorobenzyl]

[structure: 3-methyl-4-fluorobenzyl]

[structure: 2-(4-fluorophenyl)ethyl, and]

[structure: 3-(4-fluorophenyl)propyl];

R⁶ is hydrogen or alkyl of 1 to 3 carbons, the asterisk indicates a carbon which is asymmetric or may be asymmetric, the wavy line represents a bond which can be of either R or S configuration, or a pharmaceutically acceptable salt of said compound.

13. A compound in accordance with claim 12 where the variable $(R^1)_m$ in the structural formula of the compound represents a fluoro atom in the 4 (para) position of the phenyl ring relative to its side chain.

14. A compound in accordance with claim 13 having the formula

[structure]

or a pharmaceutically acceptable salt of said compound.

15. A compound of the formula

[structure]

where $R^1$ is independently F, Cl, Br, I, alkyl of 1-3 carbons, or phenyl;

m is an integer having the value of 1 to 3;

the asterisk indicates a carbon which is asymmetric, the wavy line represents a bond which can be of either R or S configuration, or a pharmaceutically acceptable salt of said compound.

16. A pharmaceutical composition for the treatment of infection by *bacillus anthraci* in a mammal, including a human, adapted for systemic administration containing a pharmaceutically acceptable excipient and one or more compounds in accordance with claim 1.

17. A method of treating infection of a mammal, including a human being, by *bacillus anthraci* by administering to said mammal a pharmaceutical composition containing a pharmaceutically acceptable excipient and one or more compounds in accordance with claim 1.

\* \* \* \* \*

UNITED STATES PATENT AND TRADEMARK OFFICE
CERTIFICATE OF CORRECTION

PATENT NO. : 8,119,692 B2
APPLICATION NO. : 12/079722
DATED : February 21, 2012
INVENTOR(S) : Alan T. Johnson and Seongjin Kim It is certified that error appears in the above-identified patent and that said Letters Patent is hereby corrected as shown below:

At Column 2 (Abstract), Line 2 (Structure), Change " 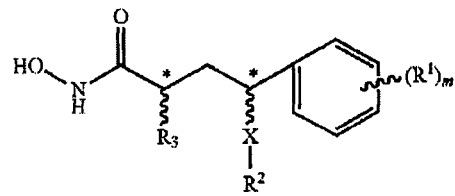 " to

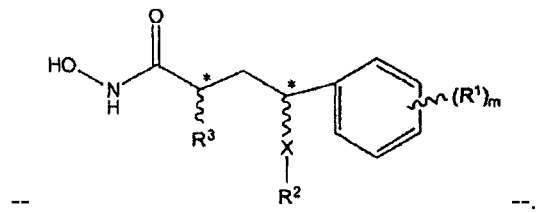

-- --.

At Column 1, Line 60, Change "Biopphys." to --Biophys.--.

At Column 3, Line 7, Change "alkylgroup" to --alkyl group--.

At Column 3, Line 11, Change "alkylgroup" to --alkyl group--.

At Column 3, Line 13, Change "heteroayl" to --heteroaryl--.

At Column 3, Line 20, Change "CH$_2$)$_p$O-phenyl" to --(CH$_2$)$_p$O-phenyl--.

At Column 4, Line 7, Change "Bu," to --Bu.--.

At Column 4, Line 10, Change "maybe" to --may be--.

At Column 4, Line 29, Change "MAP kinase enzymes" to --MAP kinase kinases enzymes--.

At Column 6, Line 19 (Table 2), Change "CH2" to --CH$_2$--.

At Column 12, Line 58 (Structure), Change "BH$_3$)" to --BH$_3$,--.

At Column 13, Line 37, Change "esther" to --ester--.

At Column 16, Line 37, Change "Formula 1" to --Formula 1.--.

At Column 17, Line 5 (Structure), Change "BH$_3$)" to --BH$_3$,--.

Signed and Sealed this
Twenty-seventh Day of November, 2012

David J. Kappos
*Director of the United States Patent and Trademark Office*

At Column 23, Line 9, Change "olephinic" to --olefinic--.

At Column 24, Line 1-2, Change "periodane)" to --periodinane)--.

At Column 24, Line 41, Change "Table 1R$^{24}$" to --Table 1 R$^2$-I--.

At Column 24, Line 42, Change "methyliodide." to --methyl iodide.--.

At Column 25, Line 35, Change "Table 1R$^2$—I" to --Table 1 R$^2$—I--.

At Column 25, Line 35-36, Change "methyliodide." to --methyl iodide.--.

At Column 33, Line 56, Change "μl" to --μL--.

At Column 38, Line 63, Change "iodine," to --iodide,--.

At Column 38, Line 64, Change "NH$^2$-OH," to --NH$_2$-OH,--.

At Column 41, Line 54, Change "(5)" to --(S)--.

At Column 42, Line 33, Change "(M+H++Na$^+$)." to --(M+H$^+$+Na$^+$).--.

At Column 45, Line 16, Change "8 h." to --8 h;--.

At Column 45, Line 39, Change "temp" to --temperature--.

At Column 46, Line 26, Change "δ7.87" to --δ 7.87--.

At Column 48, Line 61, Change "26°" to --25°--.

At Column 53, Line 6, Change "δ):" to --δ--.

At Column 58, Line 19, Change "5)" to --5).--.

At Column 62, Line 62, Change "thorough" to --through--.

At Column 71, Line 47, Change "(25)" to --(2S)--.

At Column 73, Line 44, Change "(2S)-2-(2S)-2" to --(2S)-2-((2S)-2--.

At Column 73, Line 63, Change "(2S,4E)-2-(2R)-2" to --(2S,4E)-2-((2R)-2--.

At Column 75, Line 66, Change "OMe)" to --OMe).--.

At Column 79, Line 18, Change "N-hydroxy-2-((2" to --N-hydroxy-2-(2-((2--.

At Column 81, Line 63, Change "Scheme." to --Scheme--.

At Column 89, Line 1-15 (Structure), Change " 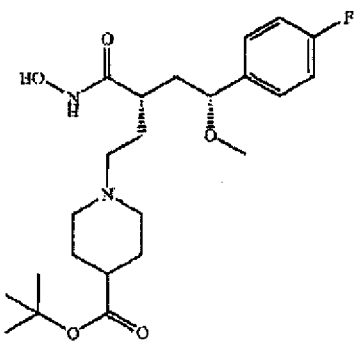 " to
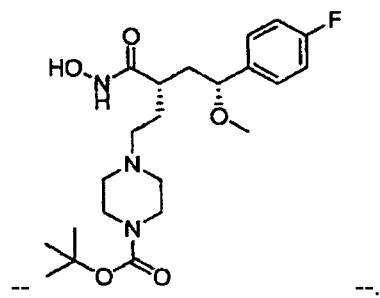
--.
At Column 95, Line 60, Change "(S)-6-(4" to --(S)-6-((4--.
At Column 95, Line 63, After "(CD$_3$OD):" insert --δ--.
At Column 96, Line 19, Change "S)-6" to --(S)-6--.
At Column 97, Line 18, Change "S)-2" to --(S)-2--.
At Column 99, Line 19, Change "S)-2" to --(S)-2--.
At Column 101, Line 5-10, In Claim 1, change " 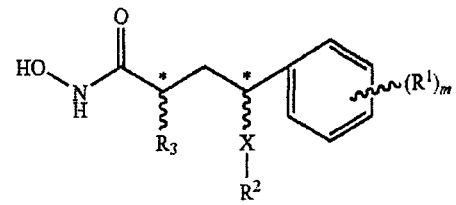 " to
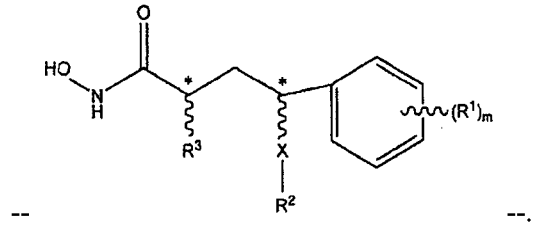
--.
At Column 101, Line 14, In Claim 1, change "or;" to --or phenyl;--.

CERTIFICATE OF CORRECTION (continued)
U.S. Pat. No. 8,119,692 B2

At Column 103, Line 5-30, (Approx.), In Claim 12, change " 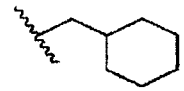 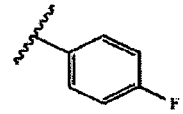 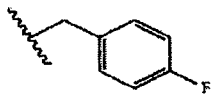  " to

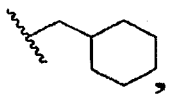

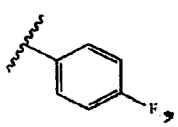

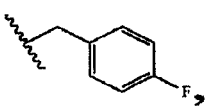

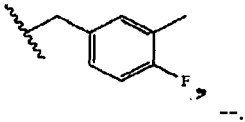

-- --.

At Column 104, Line 43, In Claim 16, change "*bacillus anthraci*" to --*bacillus anthracis*--.

At Column 104, Line 48, In Claim 17, change "*bacillus anthraci*" to --*bacillus anthracis*--.